(12) United States Patent
Fahrenkrug et al.

(10) Patent No.: US 11,477,969 B2
(45) Date of Patent: Oct. 25, 2022

(54) EFFICIENT NON-MEIOTIC ALLELE INTROGRESSION IN LIVESTOCK

(71) Applicant: Recombinetics, Inc., St. Paul, MN (US)

(72) Inventors: Scott C. Fahrenkrug, Minneapolis, MN (US); Daniel F. Carlson, Woodbury, MN (US)

(73) Assignee: Recombinetics, Inc., Eagan, MN (US)

( * ) Notice: Subject to any disclaimer, the term of this patent is extended or adjusted under 35 U.S.C. 154(b) by 861 days.

(21) Appl. No.: 16/137,246

(22) Filed: Sep. 20, 2018

(65) Prior Publication Data

US 2019/0106708 A1 Apr. 11, 2019

Related U.S. Application Data

(60) Continuation of application No. 15/802,272, filed on Nov. 2, 2017, now Pat. No. 10,959,414, which is a division of application No. 14/625,797, filed on Feb. 19, 2015, now abandoned, which is a continuation of application No. 14/263,446, filed on Apr. 28, 2014, now Pat. No. 9,528,124.

(60) Provisional application No. 61/870,401, filed on Aug. 27, 2013.

(51) Int. Cl.
*A01K 67/00* (2006.01)
*A01K 67/027* (2006.01)
*C12N 15/90* (2006.01)
*C12N 15/85* (2006.01)
*C12N 15/877* (2010.01)
*C07K 14/47* (2006.01)
*C07K 14/715* (2006.01)

(52) U.S. Cl.
CPC .......... *A01K 67/0275* (2013.01); *C07K 14/47* (2013.01); *C07K 14/715* (2013.01); *C12N 15/85* (2013.01); *C12N 15/8509* (2013.01); *C12N 15/8771* (2013.01); *C12N 15/8778* (2013.01); *C12N 15/907* (2013.01); *C12N 2750/14143* (2013.01); *C12N 2800/30* (2013.01); *C12N 2800/90* (2013.01)

(58) Field of Classification Search
None
See application file for complete search history.

(56) References Cited

U.S. PATENT DOCUMENTS

| | | | |
|---|---|---|---|
| 4,873,191 A | 10/1989 | Wagner et al. | |
| 5,142,047 A | 8/1992 | Summerton et al. | |
| 5,185,444 A | 2/1993 | Summerton et al. | |
| 5,731,178 A | 3/1998 | Sippel et al. | |
| 5,763,240 A | 6/1998 | Zarling et al. | |
| 5,948,653 A | 9/1999 | Pati et al. | |
| 6,169,172 B1 | 1/2001 | Devauchelle et al. | |
| 6,548,741 B2 | 4/2003 | DeSousa et al. | |
| 6,613,752 B2 | 9/2003 | Kay et al. | |
| 6,686,515 B1 | 2/2004 | Lassner et al. | |
| 7,144,734 B2 | 12/2006 | Court et al. | |
| 7,176,007 B2 | 2/2007 | Cox et al. | |
| 7,199,281 B2 | 4/2007 | Murray et al. | |
| 7,361,641 B2 | 4/2008 | Calos et al. | |
| 7,429,690 B2 | 9/2008 | Robl et al. | |
| 7,709,206 B2 | 5/2010 | Denise et al. | |
| 7,732,585 B2 | 6/2010 | Calos et al. | |
| 7,972,783 B2 | 7/2011 | Denise et al. | |
| 8,106,255 B2 | 1/2012 | Carroll et al. | |
| 8,518,701 B2 | 8/2013 | Fahrenkrug et al. | |
| 8,586,526 B2 | 11/2013 | Gregory et al. | |
| 8,697,359 B1 | 4/2014 | Zhang et al. | |
| 8,795,965 B2 | 8/2014 | Zhang | |
| 9,528,124 B2 | 12/2016 | Fahrenkrug et al. | |
| 10,058,078 B2 | 8/2018 | Carlson et al. | |
| 10,716,298 B2 | 7/2020 | West | |
| 10,920,242 B2 | 2/2021 | Fahrenkrug et al. | |
| 10,959,414 B2 | 3/2021 | Fahrenkrug et al. | |
| 2001/0016315 A1 | 8/2001 | Renaville et al. | |
| 2003/0232410 A1 | 12/2003 | Liljedahl et al. | |
| 2004/0038362 A1 | 2/2004 | Wei et al. | |
| 2004/0088745 A1 | 5/2004 | Robl et al. | |
| 2004/0203158 A1 | 10/2004 | Hackett et al. | |
| 2005/0003542 A1 | 1/2005 | Kay et al. | |
| 2005/0014166 A1 | 1/2005 | Trono et al. | |
| 2005/0153317 A1 | 7/2005 | Denise et al. | |
| 2010/0105140 A1 | 4/2010 | Fahrenkrug et al. | |
| 2010/0138939 A1 | 6/2010 | Bentzon et al. | |
| 2010/0146655 A1 | 6/2010 | Fahrenkrug et al. | |
| 2010/0251395 A1 | 9/2010 | Harris et al. | |
| 2011/0023140 A1 | 1/2011 | Bedell et al. | |
| 2011/0023158 A1 | 1/2011 | Bedell et al. | |
| 2011/0023159 A1 | 1/2011 | Bedell et al. | |
| 2011/0059160 A1 | 3/2011 | Essner et al. | |
| 2011/0145940 A1 | 6/2011 | Voytas et al. | |
| 2011/0197290 A1 | 8/2011 | Fahrenkrug et al. | |
| 2011/0201118 A1 | 8/2011 | Yang et al. | |
| 2011/0207221 A1 | 8/2011 | Cost et al. | |
| 2011/0262909 A1 | 10/2011 | Cargill et al. | |
| 2011/0281306 A1 | 11/2011 | Kim et al. | |
| 2011/0287545 A1 | 11/2011 | Cost et al. | |
| 2011/0301073 A1 | 12/2011 | Gregory et al. | |

(Continued)

FOREIGN PATENT DOCUMENTS

JP 2005526493 A 9/2005
JP 2009225807 A 10/2009

(Continued)

OTHER PUBLICATIONS

Ledford. Nature 583:17-18, 2020 (Year: 2020).*

(Continued)

*Primary Examiner* — Marcia S Noble
(74) *Attorney, Agent, or Firm* — Wilson Sonsini Goodrich & Rosati

(57) ABSTRACT

Methods, uses, and animals for introgression of alleles between animals, including SNPs. One embodiment involves introducing a targeted targeting endonuclease system and a HDR template into a cell with a mismatch in the binding of the targeting endonuclease and the targeted site.

20 Claims, 20 Drawing Sheets

Specification includes a Sequence Listing.

(56) References Cited

U.S. PATENT DOCUMENTS

| | | |
|---|---|---|
| 2012/0030778 A1 | 2/2012 | Weinstein et al. |
| 2012/0149115 A1 | 6/2012 | Kim et al. |
| 2012/0192298 A1 | 7/2012 | Weinstein et al. |
| 2012/0196370 A1 | 8/2012 | Urnov et al. |
| 2012/0222143 A1 | 8/2012 | Fahrenkrug et al. |
| 2013/0117870 A1 | 5/2013 | Fahrenkrug et al. |
| 2013/0198878 A1 | 8/2013 | Doyon et al. |
| 2013/0209426 A1 | 8/2013 | Bradley et al. |
| 2013/0212725 A1 | 8/2013 | Kuehn et al. |
| 2013/0217131 A1 | 8/2013 | Kim et al. |
| 2013/0298268 A1 | 11/2013 | West |
| 2013/0326645 A1 | 12/2013 | Cost et al. |
| 2014/0041066 A1 | 2/2014 | Carlson et al. |
| 2014/0120612 A1 | 5/2014 | Doyon et al. |
| 2014/0220575 A1 | 8/2014 | Hayes et al. |
| 2014/0301990 A1 | 10/2014 | Gregory et al. |
| 2015/0067898 A1 | 3/2015 | Fahrenkrug et al. |
| 2015/0071889 A1 | 3/2015 | Musunuru et al. |
| 2015/0156996 A1 | 6/2015 | Fahrenkrug et al. |
| 2016/0029604 A1 | 2/2016 | Fahrenkrug et al. |
| 2016/0081313 A1 | 3/2016 | West |
| 2016/0262360 A1 | 9/2016 | Littlejohn et al. |
| 2017/0079251 A1 | 3/2017 | Sonstegard et al. |
| 2018/0051298 A1 | 2/2018 | Fahrenkrug et al. |
| 2019/0194687 A1 | 6/2019 | Fahrenkrug et al. |
| 2019/0323031 A1 | 10/2019 | Fahrenkrug et al. |
| 2020/0296941 A1 | 9/2020 | West |

FOREIGN PATENT DOCUMENTS

| | | |
|---|---|---|
| JP | 2013518586 A | 5/2013 |
| JP | 2013529083 A | 7/2013 |
| RU | 2233334 C2 | 7/2004 |
| WO | WO-9902667 A1 | 1/1999 |
| WO | WO-0212437 A2 | 2/2002 |
| WO | WO-03057729 A2 | 7/2003 |
| WO | WO-2006116269 A2 | 11/2006 |
| WO | WO-2010079430 A1 | 7/2010 |
| WO | WO-2010143917 A2 | 12/2010 |
| WO | WO-2011002988 A1 | 1/2011 |
| WO | WO-2011011767 A1 | 1/2011 |
| WO | WO-2011017315 A2 | 2/2011 |
| WO | WO-2011019385 A1 | 2/2011 |
| WO | WO-2011072246 A2 | 6/2011 |
| WO | WO-2011078665 A1 | 6/2011 |
| WO | WO-2011146121 A1 | 11/2011 |
| WO | WO-2011154393 A1 | 12/2011 |
| WO | WO-2012012738 A1 | 1/2012 |
| WO | WO-2012094132 A1 | 7/2012 |
| WO | WO-2012116274 A2 | 8/2012 |
| WO | WO-2012152912 A1 | 11/2012 |
| WO | WO-2012168304 A2 | 12/2012 |
| WO | WO-2012168307 A2 | 12/2012 |
| WO | WO-2013088446 A1 | 6/2013 |
| WO | WO-2013191769 A1 | 12/2013 |
| WO | WO-2014041327 A1 | 3/2014 |
| WO | WO-2014093661 A2 | 6/2014 |
| WO | WO-2014153470 A2 | 9/2014 |
| WO | WO-2014165825 A2 | 10/2014 |
| WO | WO-2014189680 A1 | 11/2014 |
| WO | WO-2015030881 A1 | 3/2015 |
| WO | WO-2015060732 A1 | 4/2015 |
| WO | WO-2015168125 A1 | 11/2015 |
| WO | WO-2016049182 A1 | 3/2016 |

OTHER PUBLICATIONS

Schaefer et al. Nat Methods 14(4) 547-547, 2017. Author Manuscript pp. 1-3 (Year: 2017).*

Lee & Kim. Nature Biotechnology Advanced Online Publication. doi:10.1038/nbt.4207. 2018. pp. 1-2 (Year: 2018).*

Altschul et al. Basic local alignment search tool. J Mol Biol 215(3):403-410 (1990).

Bagle et al. Transgenic Animals and their Application in Medicine. International Journal of Medical Research & Health Sciences. 2(1):107-116 (2012).

Bryan et al., 2013, http://www.elsevierblogs.com/currentcomments/?p=962, Implications of protein fold switching, pp. 1-4.

Burrow. Variances and covariances between productive and adaptive traits and temperament in a composite breed of tropical beef cattle. Livestock Production Science 70(3):213-233 (Aug. 2001). DOI: https://doi.org/10.1016/S0301-6226(01)00178-6.

Carstea et al. Germline competence of mouse ES and iPS cell lines: Chimera technologies and genetic background. World J Stem Cells 1(1):22-29 (Dec. 31, 2009).

Davis et al. Breeding and Genetics Symposium: Breeding heat tolerant dairy cattle: the case for introgression of the "slick" prolactin receptor variant into Bos taurus dairy breeds. J Anim Sci 95:1788-1800 (2017).

Definition of the term "for." Dictionary.com. Retrieved Dec. 3, 2019 from URL: <http://dictionary.com/browse/for>. 8 pages.

EP15844824.1 Office Action dated Nov. 29, 2019.

EP15844824.1 Extended European Search Report dated Apr. 23, 2018.

Gish et al. Identification of protein coding regions by database similarity search. Nature Genetics 3:266-272 (1993).

Guo et al. Targeted genome editing in primate embryos. Cell Research 25:767-768 (2015). Published online Jun. 2, 2015.

Hammond et al. Heat tolerance in Tuli-, Senepol-, and Brahman-sired F1 Angus heifers in Florida. Journal of Animal Science 76(6):1568-1577 (Jun. 1, 1998). DOI: https://doi.org/10.2527/1998.7661568x.

Hammond et al. Heat tolerance in two tropically adapted Bos taurus breeds, Senepol and Romosinuano, compared with Brahman, Angus, and Hereford cattle in Florida. Journal of Animal Science 74(2):295-303 (Feb. 1, 1996). DOI: https://doi.org/10.2527/1996.742295x.

Hammond et al. Rectal temperature and grazing time in selected beef cattle breeds under tropical summer conditions in subtropical Florida. Tropical Agriculture (Trinidad and Tobago). (Apr. 1994). v. 71(2) p. 128-134.

Heo et al. CRISPR/Cas9 Nuclease-Mediated Gene Knock-In in Bovine-Induced Pluripotent Cells. Stem Cells and Development. 24(3):393-402 (2015). Prepublished online Sep. 11, 2014.

Higgins et al. [22] Using CLUSTAL for multiple sequence alignments. Methods Enzymol 266:383-402 (1994). DOI: https://doi.org/10.1016/S0076-6879(96)66024-8.

Houdebine. Transgenic Animal Models in Biomedical Research. Methods in Molecular Biology, vol. 360, Target Discovery and Validation Reviews and Protocols, vol. 1, Emerging Strategies for Targets and Biomarker Discovery, pp. 163-202 (2007).

Huang. Studies on Truncated Isoforms of the Prolactin Receptors. A Dissertation submitted in partial satisfaction of the requirement for the degree of Doctor of Philosophy in Biomedical Sciences, University of California Riverside. ProQuest Dissertations & Theses Global: The Sciences and Engineering Collection (Aug. 2008). 154 pages.

Katsuyama et al. An efficient strategy for TALEN-mediated genome engineering in *Drosophila*. Nucleic Acids Research 41(17):e163 (Sep. 1, 2013). Epub Jul. 22, 2013. DOI: https://doi.org/10.1093/nar/gkt638. 9 pages.

Khodarovich et al. Expression of Eukaryotic Recombinant Proteins and Deriving Them From the Milk of Transgenic Animals. Applied Biochemistry and Microbiology 49(9):711-722 (2013).

Lee et al. Developing genetically engineered mouse models using engineered nucleases: Current status, challenges, and the way forward. Drug Discovery Today: Disease Models, vol. 20, pp. 13-20, Summer 2016. DOI: https://doi.org/10.1016/j.ddmod.2017.07.003.

Lu et al., TALEN-Mediated Gene Mutagenesis in Rhesus and Cynomolgus Monkeys. Cell Stem Cell, 14.3 (Mar. 6, 2014): 323-328.

Mackinnon et al. Genetic variation and covariation for growth, parasite resistance and heat tolerance in tropical cattle. Livestock Production Science 27(2-3):105-122 (Feb. 1991). DOI: https://doi.org/10.1016/0301-6226(91)90090-D.

(56) References Cited

OTHER PUBLICATIONS

Maksimenko et al. Use of Transgenic Animals in Biotechnology: Prospects and Problems. Acta Naturae 5(1):33-46 (2013).

Maqbool et al. The substrate-binding protein in bacterial ABC transporters: dissecting roles in the evolution of substrate specificity. Biochem Soc Trans 43:1011-1017 (2015).

Mariasegaram et al. The slick hair coat locus maps to chromosome 20 in Senepol-derived cattle. Anim Genet 38(1):54-59 (Feb. 2007). doi:10.1111/j.1365-2052.2007.01560.x.

Miao et al. Recent Advances and Applications of Transgenic Animal Technology. IntechOpen (May 30, 2012). DOI: 10.5772/38040. 30 pages.

NCBI, GenBank accession No. AAA51417.1, Apr. 27, 1993.

Pandey. Functional Effects of Proline Substitutions into Sindbis Virus E2 Transmembrane Domain. Abstracts, 59th Southeast Regional Meeting of the American Chemical Society, Greenville, SC, United States, Oct. 24-27, 2007, GEN-671, Publisher: American Chemical Society, Washington D.C. One page.

Patil et al. Transgenic animals and drug development: A review. Indian Journal of Public Health Research & Development 2(1):106-109 (Jan.-Jun. 2011).

PCT/US2015/051717 International Preliminary Report on Patentability dated Mar. 28, 2017.

PCT/US2015/051717 International Search Report and Written Opinion dated Dec. 30, 2015.

Pearson et al. Improved tools for biological sequence comparison. PNAS USA 85(8):2444-2448 (1988).

Porto-Neto et al. Convergent Evolution of Slick Coat in Cattle through Truncation Mutations in the Prolactin Receptor. Frontiers in Genetics. vol. 9, Article 57 (Feb. 23, 2018). 8 pages. DOI: https://doi.org/10.3389/fgene.2018.00057.

Selsby et al. Porcine Models of Muscular Dystrophy. ILAR Journal 56(1):116-126 (2015).

Shinohara et al. Active integration: new strategies for trangenesis. Transgenic Res 16:333-339 (2007). Published online Mar. 6, 2007.

The Heliconius Genome Consortium. Butterfly genome reveals promiscuous exchange of mimicry adaptations among species. Nature 487:94-98 (Jul. 5, 2012). Published online May 16, 2012.

Thompson, et al. Clustal W: improving the sensitivity of progressive multiple sequence alignment through sequence weighting, position-specific gap penalties and weight matrix choice. Nucleic Acids Res. Nov. 11, 1994;22(22):4673-80.

Turner. Genetic variation of rectal temperature in cows and its relationship to fertility. Animal Science 35(3):401-412 (Dec. 1982). DOI: https://doi.org/10.1017/S0003356100001094.

Turner. Variation in rectal temperature of cattle in a tropical environment and its relation to growth rate. Animal Science 38(1):417-427 (Jun. 1984). DOI: https://doi.org/10.1017/S0003356100041611.

U.S. Appl. No. 14/862,900 Office Action dated Dec. 16, 2019.
U.S. Appl. No. 14/862,900 Office Action dated Feb. 7, 2017.
U.S. Appl. No. 14/862,900 Notice of Allowance dated Mar. 9, 2020.
U.S. Appl. No. 14/862,900 Office Action dated Aug. 30, 2017.
U.S. Appl. No. 15/802,272 Office Action dated Dec. 4, 2019.
U.S. Appl. No. 16/294,619 Office Action dated Dec. 6, 2019.
U.S. Appl. No. 14/862,900 Office Action dated Jul. 30, 2019.
U.S. Appl. No. 14/862,900 Office Action dated May 30, 2018.
U.S. Appl. No. 14/862,900 Office Action dated Nov. 20, 2018.

Zu et al. TALEN-mediated precise genome modification by homologous recombination in zebrafish. Nature Methods, vol. 10, pp. 329-331 (2013). Epub Feb. 24, 2013.

Agricultural Research Information System Request to Submit Manuscript for Publication. Project No. 1245-31000-104-00D, Log No. 303151, Creation Date: Feb. 24, 2014, Submitter: Tad S. Sonstegard. Title of Manuscript: The identification of a putative mutation for SLICK hair coat in Senepol cattle. 04466 Meeting abstract. 3 pages.

Endo et al. CIS1 interacts with the Y532 of the prolactin receptor and suppresses prolactin-dependent STAT5 activation. J Biochem. Jan. 2003;133(1):109-13.doi: 10.1093/jb/mvg004.

U.S. Appl. No. 16/294,619 Office Action dated Jun. 28, 2019.
U.S. Appl. No. 15/270,901 Office Action dated Feb. 22, 2018.
U.S. Appl. No. 15/270,901 Office Action dated Sep. 21, 2018.

Bignon et al. Long and short forms of the ovine prolactin receptor: cDNA cloning and genomic analysis reveal that the two forms arise by different alternative splicing mechanisms in ruminants and in rodents. Journal of Molecular Endocrinology 19:109-120 (1997).

Craven et al. Prolactin Signaling Influences the Timing Mechanism of the Hair Follicle: Analysis of Hair Growth Cycles in Prolactin Receptor Knockout Mice. Endocrinology 142(6):2533-2539 (Jun. 1, 2001).

Kildebeck et al. Engineered nuclease mediated gene targeting of the human IL2Ry gene. Molecular Therapy, vol. 20, Suppl. 1, pp. S89. Abstract No. 227. 15th Annual Meeting of the American Society of Gene and Cell Therapy, ASGCT 2012. Philadelphia, PA, United States. May 16-20, 2012.

Mali, et al. RNA-Guided Human Genome Engineering via Cas9. Science. Feb. 15, 2013; 339(6121): 823-826. Published online Jan. 3, 2013. doi: 10.1126/science.1232033.

Porteus et al. Gene targeting using zinc finger nucleases. Nature Biotechnology 23(8):967-973 (Aug. 8, 2005).

Tchelet et al. Extracellular domain of prolactin receptor from bovine mammary gland: expression in *Escherichia coli*, purification and characterization of its interaction with lactogenic hormones. Journal of Endocrinology 144:393-403 (1995).

EP14840061.7 Office Action dated Feb. 5, 2019.

Wang, et al. One-step generation of mice carrying mutations in multiple genes by CRISPR/Cas-mediated genome engineering. Cell. May 9, 2013;153(4):910-8. doi: 10.1016/j.cell.2013.04.025. Epub May 2, 2013.

Wei et al. TALEN or Cas9—Rapid, Efficient and Specific Choices for Genome Modifications. Journal of Genetics and Genomics 40:281-289 (2013).

GenBank Accession No. NM_001039726. Version No. NM_001039726.2. Bos taurus prolactin receptor (PRLR), transcript variant 2, mRNA. Feb. 9, 2014. 3 pages. Retrieved Apr. 28, 2020 at URL: https://www.ncbi.nlm.nih.gov/nuccore/402692615?sat=18&satkey=28628326.

Hammer et al. The curli nucleator protein, CsgB, contains an amyloidogenic domain that directs CsgA polymerization. Proc Natl Acad Sci U S A. Jul. 24, 2007; 104(30): 12494-12499. Published online Jul. 16, 2007. doi: 10.1073/pnas.0703310104.

U.S. Appl. No. 15/802,272 Office Action dated Jun. 15, 2020.
U.S. Appl. No. 16/294,619 Office Action dated Sep. 4, 2020.

Alexander et al., A Limousin Specific Myostatin Allele Affects Longissimus Muscle Area and Fatty Acid Profiles n A Wagyu-Limousin F2 Population, Journal of Animal Science, 87 (Dec. 5, 2014): 1576-1581.

Bedell, et al. In vivo genome editing using a high-efficiency TALEN. Nature. 491.7422 (2012): 114-118.

Blake et al., Function and Genetics of Dystrophin and Dystrophin-Related Proteins in Muscle. Physiol Rev, 82 (2002): 291-329.

Breeding for Polledness, SBTS TechTalk, (Nov. 2013): 4 Pages.

Carbery et al., Targeted Genome Modification in Mice Using Zinc-Finger Nucleases. Genetics Society of America, 186 (2010): 451-459.

Carlson et al., 328 Versatile Transcription Activator-Like Effector Nuclease (TALEN)-Mediated Engineering of Dssabaw Miniature Swine. Reproduction, Fertility and Development, 25.1 (Dec. 4, 2012): 312. Abstract Only.

Carlson et al., Adding and Subtracting Livestock Genes With Transposons and Nucleases. Transgenic Research, 21.4 (Aug. 2011): 901-902.

Carlson et al., Editing Livestock Genomes With Site-Specific Nucleases. Reproduction, Fertility and Development, 26 (2014): 74-82.

Carlson et al., Efficient TALEN-Mediated Gene Knockout in Livestock. Proceeding of the National Academy of Sciences, 109.43 (Oct. 23, 2012): 17382-17387.

Carlson et al., Strategies for Selection Marker-Free Swine Transgenesis Using the Sleeping Beauty Transposon System. Transgenic Research, Jan. 9, 2011, 13 Pages.

Carlson et al., Targeting DNA with Fingers and TALENs. Molecular Therapy—Nucleic Acid, 1 (2012): 1-5.

(56) References Cited

OTHER PUBLICATIONS

Casas et al., Quantitative Trait Loci Affecting Growth and Carcass Composition of Cattle Segregating Alternate forms of Myostatin. Journal of Animal Science, 78 (2000): 560-569.
Cermak, et al. Efficient design and assembly of custom TALEN and other TAL effector-based constructs for DNA targeting. Nucleic Acids Res. 39.12 (Jul. 2011): e82. doi: 10.1093/nar/gkr218. Epub Apr. 14, 2011.
Chen et al., High-Frequency Genome Editing Using ssDNA Oligonucleotides With Zinc-Finger Nucleases. Nature Methods Advance Online Publication Published Online Jul. 17, 2011. 32 pages. DOI: 10.1038/NMETH.1653.
Christian, et al. Targeting DNA double-strand breaks with TAL effector nucleases. Genetics.186 (2010): 757-761.
Cibelli, et al. Cloned transgenic calves produced from nonquiescent fetal fibroblasts. Science, 280 (1998):1256-1258.
Clark et al., A TALE of Two Nucleases: Gene Targeting for the Masses? Minireview, 8.3 (2011): 147-149.
Clark et al., Enzymatic Engineering of the Porcine Genome with Transposons and Recombinases. BMC Motechnology, 7.42 (Jul. 17, 2007): 1-17.
Clark et al., Isolation, DNA Sequence, and Regulation of *Saccharomyces cerevisiae* Gene That Encode DNA Strand Transfer Protein alpha. Molecular and Cellular Biology, 11.5 (May 1991): 2576-2582.
Cox, Historical Overview: Searching for Replication Help in all of the Rec Places Proceedings of the National Academy of Science, 98.15 (Jul. 17, 2001): 8173-8180.
Cui et al., RecA-mediated, Targeted Mutagenesis in Zebrafish Marine Biotechnology, 5 (2003): 174-184.
Dong et al., Heritable Targeted Inactivation of Myostatin Gene in Yellow Catfish (*Pelteobagrus Fulvidraco*) Using Engineered Zinc Finger Nucleases. PLoS One, 6.12 (Dec. 2011): p. e28897.
Doyon, et al., Heritable targeted gene disruption in zebrafish using designed zinc-finger nucleases. Nat Biotechnol. 26.6 (Jun. 2008): 702-8. doi: 10.1038/nbt1409. Epub May 25, 2008.
Doyon et al., Transient Cold Shock Enhances Zinc-Finger Nuclease-Mediated Gene Disruption. Nature Methods 7.6 (Jun. 2010): 459-461.
Fahrenkrug et al., 95 Production of Gene-Edited Pigs, Cattle, and Lambs by Embryo Injection of TALENS or 1 FNs. Reproduction, Fertility and Development, 26.1 (Dec. 5, 2013): 161. Abstract Only.
Farzadfard et al., Tunable and Multifunctional Eukaryotic Transcription Factors Based on CRISPR/Cas, ACS Synthetic Biology, 2 (2013): 604-613.
Geurts et al., Knockout Rats Produced Using Designed Zinc Finger Nucleases, Science, 325 (Jul. 24, 2009), p. 433.
Geurts et al., Knockout Rats via Embryo Microinjection of Zinc-Finger Nucleases. Science, 325 (Jul. 24, 2009): 433.
Grobet et al., A Deletion in the Bovine Myostatin Gene Causes the Double-Muscled Phenotype in Cattle, Nature Genetics, 17 (Sep. 17, 1997), p. 71.
Hauschild et al., Efficient Generation of a Biallelic Knockout in Pigs Using Zinc-Fingers Nucleases. Proceedings of the National Academy of Sciences, 108 (2011): 12013-12017.
High., Gene therapy: the moving finger. Nature, 435 (2005): 577-579.
Hsieh et al., Formation of Joint DNA Molecules by Two Eukaryotic Strand Exchange Proteins Does not Require Melting of a DNA Duplex. The Journal of Biological Chemistry, 264.9 (Mar. 25, 1989): 5089-5097.
Huang et al., Heritable Gene Targeting in Zebrafish Using Customized TALENs. Nature Biotechnology, 29.8 (Aug. 2011): 699-700.
Jinek et al. RNA-programmed genome editing in human cells, elife 2 (2013): e00471.
Kambadur et al., Mutations in Myostain (GDF8) in Double-Muscled Belgian Blue and Piedmontese Cattle. Genome Res., 7 (1997): 910-915.
Kawakami, Tol2: a versitile gene transfer vector in vertebrates. Genome Biology, 8(suppl 1) article s7, S7.1-S7.10 (2007).
Kim et al., Targeted Genome Editing in Human Cells with Zinc Finger Nucleases Constructed via Modular Assembly. Genome Research, 19 (2009): 1279-1288.
Lee et al, Targeted Chromosomal Deletions in Human Cells Using Zinc Finger Nucleases. Genome Research, 20 (Dec. 1, 2009): 81-89.
Li et al. In vivo genome editing restores haemostasis in a mouse model of haemophilia. Nature 475.7355 (2011): 217-221, plus Supplemental Material.
Li et al. TAL Nucleases (TALNs): Hybrid Proteins Composed of TAL Effectors and FokI DNA-Cleavage Domain, gucleic Acids Research, 39.1 (Aug. 10, 2010): 359-372.
Liao et al., Use of RecA Fusion Proteins to Induce Genomic Modifications in Zebrafish. Nucleic Acids Research, (2011): 14 Pages.
Lillico et al., Live Pigs Produced From Genome Edited Zygotes, Scientific Reports, (Oct. 10, 2013): 4 pages.
Lo. Transformation by iontophoretic microinjection of DNA: multiple integrations without tandem insertions. Mol. Cell. Biol., 3.10 (1983): 1803-1814.
Ma et al., High Efficiency In Vivo Genome Engineering with a Simplified 15-RVD GoldyTALEN Design. PLOS One, 8.5 (May 2013): 1-8.
Maeshima et al., RAD51 Homologues in Xenopus laevis: Two Distinct Genes are Highly Expressed in Ovary and Testis. Gene, 160 (1995): 195-200.
Mali et al., RNA-Guided Human Genome Engineering via Cas9. Science, 339 (Feb. 15, 2013): 823-826.
Mashimo et al., Generation of Knockout Rats with X-linked Severe Combined Immunodeficiency (X-SCID) Using Zinc-Finger Nucleases. PLoS One, 5.1, Jan. 2010.
Medugorac et al., Bovine Polledness—Autosomal Dominant Trait with Allelic Heterogeneity. PLoS One, 7 .6 (Jun. 2012): 1-11.
Meng et al., Targeted gene inactivation in zebrafish using engineered zinc finger nucleases. Nat. Biotechnol., 26.6 (Jun. 2008): 695-701.
Meyer et al., Modeling Disease Mutations by Gene Targeting in One-Cell Mouse Embryos. Proceeding of the gational Academy of Science, 109.24 (Jun. 12, 2012): 9354-9359.
Miller et al. A TALE nuclease architecture for efficient genome editing. Nat Biotechnol. 29.2 (Feb. 2011): 143-8. doi: 10.1038/nbt.1755. Epub Dec. 22, 2010.
Miskey et al., The Ancient Mariner Sails Again: Transposition of the Human Hsmar1 Element by a Reconstructed Transposase and Activites of the SETMAR Protein on Transposon Ends. Molecular and Cellular Biology, 27.12 (Jun. 2007): 4589-4600.
Miskey et al., The Frog Prince: a reconstructed transposon from Rana pipiens with high tanspositional activity in vertebrate cells. Nucleic Acids Res. 31.23 (2003): 6873-6881.
Moore et al., Purification and Characterization of a Protein from Human Cells Which Promotes Homologous Pairing of DNA. The Journal of Biological Chemistry, 265.19 (Jul. 5, 1990): 11108-11117.
Mussolino et al., A Novel TALE Nuclease Scaffold Enables High Genome Editing Activity in Combination With Low Toxicity. Nucleic Acids Research, 39.21 (Jul. 5, 2011): 9283-9293.
Orban et al., Tissue and Site-Specific DNA Recombination in Transgenic Mice. Proceedings of the National Acedemy of Science, 89 (Aug. 1992): 6861-6865.
Palgrave et al., Species-Specific Variation in RELA Underlies Differences in NF-KB Activity: A Potential Role in African Swine Fever Pathogenesis. Journal of Virology, 85.12 (Jun. 2011): 6008-6014.
Pavlopoulos et al., The DNA transposon Minos as a tool for transgenesis and functional genomic analysis in vertebrates and invertebrates. Genome biology 8.1 (suppl 1) article S2 (2007): S2.1-S2.7.
PCT/US14/35854 International Search Report and Written Opinion dated Nov. 17, 2014.
Porteus, et al., Gene targeting using zinc finger nucleases—Semantic Scholar. Nature Biotech., 23.8 (2005): 967-973.
Proudfoot et al., Genome Edited Sheep and Cattle, Transgenic Research, 24 (Sep. 10, 2015): 147-153.

(56) References Cited

OTHER PUBLICATIONS

Purchas et al., Composition and Quality Differences Between The Longissimus and Infraspinatus Muscles for Several Groups of Pasture-Finished Cattle. Meat Science, 80 (Jan. 21, 2008): 470-479.
Ramirez., Unexpected failure rates for modular assembly of engineered zinc fingers. Nature Methods, 5.5 (2008): 374-375.
Sander et al., Engineering Zinc Finger Nucleases for Targeted Mutagenesis of Zebrafish, Methods in Cell Thology, 104 Chapter 3 (2011): 51-58.
Specht., Polled Holstein History, Department of Dairy and Animal Science (2008): 32 pages.
Tan et al., Efficient Nonmeiotic Allele Introgression in Livestock Using Custom Endonucleases. Proceeding of the 1ational Academy of Sciences, (Aug. 13, 2013): 6 pages.
Tan et al., Efficient Non-Meiotic Allele Introgression in Livestock Using TAL Effector Nucleases and The CRISPR—cas9 System. Transgenic Research, 23 (2014): 187-210. Abstract Only.
Tan et al., Gene Targeting of The Swine Myostain Gene Using rAAV and TALENs. Transgenic Research 21 (2012): 901-925. Absrtact Only.
Tan, et al. Precision editing of large animal genomes. Adv Genet. 2012;80:37-97. doi: 10.1016/B978-0-12-404742-6.00002-8.
Tan, Genome Engineering in Large Animals for Agricultural and Biomedical Applications, A Dissertation Submitted to the Faculty of University of Minnesota (Aug. 2013).
Tesson et al, Knockout Rats Generated by Embryo Microinjection of TALENs. Nature Biotechnology, 29.8 (Aug. 2011): 695-696.
Thompson, et al. Germ line transmission and expression of a corrected HPRT gene produced by gene targeting in embryonic stem cells. Cell, 56 (1989):313-321.
U.S. Appl. No. 13/404,662 Office Action dated Apr. 3, 2015.
U.S. Appl. No. 13/594,694 Office Action dated Apr. 15, 2015.
Van Der Putten, et al. Efficient insertion of genes into the mouse germ line via retroviral vectors. Proc. Natl. Acad. Sci. USA, 82 (1985): 6148-1652.
Watanabe et al, Knockout of Exogenous EGFP Gene in Porcine Somatic Cells Using Zinc-Finger Nucleases. Biochemical and Biophysical Research Communications, 402 (2010): 14-18.
Whyte et al, Cell Biology Symposium: Zinc Finger Nucleases to Create Custom-Designed Modifications in The Swine (*Sus scrota*) Genmoe. National Swine Resource and Research Center and Division of Animal Science, Jan. 20, 2015.
Beurdeley et al. Compact designer TALENs for efficient genome engineering. Nat Commun 4:1762 (2013), 8 pages.
Brooks., Molecular Mechanisms of Prolactin and It's Receptor. Endocrine Reviews, 33.4 (Aug. 2012): 504-525.
Cong, et al. Multiplex genome engineering using CRISPR/Cas systems. Science. 339.6121 (Feb. 15, 2013): 819-23. doi: 10.1126/science.1231143. Epub Jan. 3, 2013.
EP14840061.7 Office Action dated Apr. 19, 2018.
EP14840061.7 Extended European Search Report dated May 10, 2017.
Gaj, et al. ZFN, TALEN, and CRISPR/Cas-based methods for genome engineering. Trends Biotechnol. Jul. 2013;31(7):397-405. doi: 10.1016/j.tibtech.2013.04.004. Epub May 9, 2013.
Goa et al., Genome Biology 18 (2017): 1-15.
Huson et al., Genome-wide Association Study and Ancestral Origins of the Slick-Hair Coat in Tropically Adapted Cattle. Genetics, 5 (Apr. 2014): 1-12.
Kildeback and Porteus, Molecular Therapy, 20 (Supplement 1):S89, Abstract No. 227, May 2012.
Lavitrano et al., Efficient Production by Sperm-Mediated Gene Transfer of Human Decay Accelerating Factor (hDAF) Transgenic Pigs for Xenotransplantation, Proceedings of the National Academy of Science, 99.22 (Oct. 29, 2002): 14230-14235.
Lavitrano et al., Sperm-Mediated Gene Transfer, Reproduction, Fertility and Development, 18 (2006): 19-23.
Li et al. Precise correction of the dystrophin gene in duchenne muscular dystrophy patient induced pluripotent stem cells by TALEN and CRISPR-Cas9. Stem Cell Reports 4 (2015): 143-154.
Littlejohn et al., Functionally reciprocal mutations of the prolactin signalling pathway define hairy and slick cattle. Nature Comm. 5 (2014): 5861-5869.
Maeder et al., Genome-editing Technologies for Gene and Cell Therapy. Mol Ther. 24.3 (2016): 430-446.
Mali et al., RNA-Guided Human Genome Engineering via Cas9. Science Magizine, (Jan. 3, 2013): 5 Pages.
Nishiyama et al., A Glycine-Rich RNA-Binding Protein Mediating Cold-Inducible Suppression of Mammalian Cell Growth. Journal of Cell Biology, 37.4 (May 19, 1997): 899-908.
Olson et al. Evidence of a major gene influencing hair length and heat tolerance in Bos taurus cattle. J Animal Sci, 81 (2003): 80-90.
Olson et al. Harmful recessive effects on fertility detected by absence of homozygous haplotypes, J Dairy Sci., 2011,94(12):6153-6161.
PCT/US2014/035854 International Preliminary Report on Patentability dated Mar. 1, 2016.
Pezet et al., Tyrosine Docking Sites of the Rat Prolactin Receptor Required for Association and Activation of 3tat5. Journal of Biological Chemistry, 272.40 Oct. 3, 1997): 25043-25050.
Printout from https://en.wikipedia.org/wiki/lntrogression printed out dated Jun. 18, 2018, pp. 1-5.
EP14840061.7 Partial Supplementary European Search Report dated Feb. 3, 2017.
Thomsen et al. A missense mutation in the bovine SLC35A3 gene, encoding a UDP-N-acetylglucosamine transporter, causes complex vertebral malformation, Genome Res., Jun. 2018;16(1):97-105.
U.S. Appl. No. 14/263,446 Non-Final Office Action dated Mar. 31, 2016.
U.S. Appl. No. 14/263,446 Notice of Allowance dated Aug. 18, 2016.
U.S. Appl. No. 14/625,797 Non-Final Office Action dated May 10, 2017.
U.S. Appl. No. 15/802,272 Notice of Allowance dated Dec. 22, 2020.
Branda et al., Talking About a Revolution: The Impact of Site-Specific Recombinases on Genetic Analyses in Mice. Developmental Cell, 6.1 (Jan. 2004): 7-28.
Cogoni et al., Gene Silencing in Neurospora crassa Requires a Protein Homologous to RNA-Dependent RNA Polymerase. Nature 399 (May 13, 1999): 166-169.
Cogoni et al., Transgene Silencing of the al-1 Gene in Vegetative Cells of Neurospora in Mediated by a Cytoplasmic Effector and Does Not Depend on DNA-DNA interactions or DNA Methylation. The EMBO Journal. 15.12 (1996): 3153-3163.
Co-pending U.S. Appl. No. 16/282,232, filed Feb. 21, 2019.
Dieffenbach, et al. PCR Primer: A Laboratory Manual, ed. Cold Spring Harbor Laboratory Press, 1995.
Dupuy et al., Mammalian Germ-Line Transgenesis by Transposition Proceeding of the National Academy of Sciences, 99.7 (2002): 4495-4499.
Fire et al. Potent and specific genetic interference by double-stranded RNA in Caenorhabditis elegans. Nature 391 (1998): 806-811.
Guatelli et al. Isothermal, in vitro amplification of nucleic acids by a multienzyme reaction modeled after retroviral replication. PNAS USA 87(5):1874-1878 (1990).
International search report with written opinion dated Dec. 19, 2016 for PCT/US2016/052693.
Kennerdell et al., Use of dsRNA-Mediated Genetic Interference to Demonstrate that frizzled and frizzled 2 Act in the Wingless Pathway. Cell, 95 (Dec. 23, 1998): 1017-1026.
Kiwaki et al., Correction of Ornithine Transcarbamylase Deficiency in Adult spfash Mice and in OTC-Deficient Human Hepatocytes with Recombinant Adenoviruses Bearing the CAG Promoter. Human Gene Therapy, 7 (May 1, 1996): 821-830.
Lewis. PCR's Competitors are alive and well and moving rapidly towards commercialization. Genetic Engineering News, 12.1 (1992): 2 pages.

(56) References Cited

OTHER PUBLICATIONS

Mcintyre et al., Design and Cloning Strategies for Constructing shRNA Expression Vectors. BMC Biotechnology, 6.1 (Jan. 5, 2006): 8 Pages.
Misquitta et al, Targeted Disruption of Gene Function in *Drosophila* by RNA Interference (RNA-i): A Role for Nautilus in Embryonic Somatic Muscle Formation. Proceedings of the National Academy of Science, 96 (Feb. 1999): 1451-1456.
PCT/US2016/052693 International Preliminary Report on Patentability dated Mar. 27, 2018.
Dikmen et al. The SLICK hair locus derived from Senepol cattle confers thermotolerance to intensively managed lactating Holstein cows. J. Dairy Sci. 97:5508-5520.
Sonstegard et al., The identification of a putative mutation for SLICK hair coat in Senepol cattle. Abstract from 2014 JAM Joint Annual Meeting (Jul. 20-24, 2014, Kansas City, Missouri). J Anim Sci vol. 92, E-Suppl 2 / J Dairy Sci vol. 97, E-Suppl 1, p. 86.
Romano et al., Quelling: transient inactivation of gene expression in Neurospora crassa by transformation with homologous sequences. Mol. Microbiol., 6.22 (1992): 3343-3353.
EP16849434.2 Extended European Search Report dated Jan. 25, 2019.
U.S. Appl. No. 15/270,901 Non-Final Office Action dated Feb. 22, 2018.
Visscher et al., Breeding Objectives for Pasture Based Dairy Production Systems. Livestock Production Science, 40 (1994): 123-137.
Wakayama, et al. Full-term development of mice from enucleated oocytes injected with cumulus cell nuclei. Nature, 394 (1998): 369-374.
Weiss. Hot prospect for new gene amplifier. Science, 254 (1991): 1292-1293.
Wilmut, et al. Viable offspring derived from fetal and adult mammalian cells. Nature, 385 (1997): 810-813.
Xu et al., CMV-β-Actin Promoter Directs Higher Expression from an Adeno-Associated Viral Vector in the Liver than the Cytomegalovirus or Elongation Factor 1α Promoter and Results in Therapeutic Levels of Human Factor X in Mice, Hum Gene Ther., 12 (2001): 563-573.
Addgene's webpage for Daniel Carlson Lab Plasmids. Retrieved Mar. 4, 2021 at URL: https://www.addgene.org/Daniel_Carlson/. One page.
Enhancing Genetic Merit of Ruminants through Genome Selection and Analysis (Research Project #423740), 2013 Annual Report, Animal Genomics and Improvement Laboratory, Beltsville, MD. Dated Jun. 25, 2013. Available at: https://www.ars.usda.gov/research/project/?accnNo=423740&fy=2013.
GenBank Accession No. L02549. Version No. L02549.1. Bos taurus (clone bPRLR 107 and 203) prolactin receptor (PRLR) mRNA, complete cds. Oct. 30, 1994. 2 pages. Retrieved Apr. 12, 2021 at URL: https://www.ncbi.nlm.nih.gov/nucleotide/L02549.1?report=genbank&log$=nucltop&blast_rank=2 &RID=YS91ASFE016.
Gupta et al. Expanding the genetic editing tool kit: ZFNs, TALENs, and CRISPR-Cas9. J Clin Invest 2014;124(10):4154-4161.
Ormandy et al. Null mutation of the prolactin receptor gene produces multiple reproductive defects in the mouse. Genes & Development 11:167-178 (1997).
Prolactin receptor long form precursor [Bos taurus], NCBI Reference Sequence: NP_001034815.1. Feb. 9, 2014. Retrieved Mar. 3, 2021 from URL: https://www.ncbi.nlm.nih.gov/protein/89886439?sat=18&satkey=28628326. 2 pages.
Smit et al. Mosaicism of Solid Gold supports the causality of a noncoding A-to-G transition in the determinism of the callipyge phenotype. Genetics. Jan. 2003;163(1):453-6.
U.S. Appl. No. 16/282,232 Office Action dated Oct. 15, 2021.
U.S. Appl. No. 16/294,619 Office Action dated May 26, 2021.
Winter et al. Association of a lysine-232/alanine polymorphism in a bovine gene encoding acyl-CoA:diacylglycerol acyltransferase (DGAT1) with variation at a quantitative trait locus for milk fat content. Proc Natl Acad Sci U S A. Jul. 9, 2002;99(14):9300-5.

\* cited by examiner a
```
              CCGTCCTTTGCCAacCtT                  AGCAACCGTGGGCCCCAA
Wt-NL  TCCGTCCTTTGCCAacCtTGGCCGACCAGCCCTTAGCAACCGTGGGCCCCAA
DF-HDR TCCGTCCTTTGCCGAcTtCGGCCGACCAGCCCTTAGCAACCGTGGGCCCCAA
                           Eagl
``` b c

FIG. 17

EFFICIENT NON-MEIOTIC ALLELE INTROGRESSION IN LIVESTOCK

CROSS REFERENCE TO RELATED APPLICATIONS

This application is a Continuation U.S. patent application Ser. No. 15/802,272, filed Nov. 2, 2017, which is a Divisional of U.S. patent application Ser. No. 14/625,797, filed on Feb. 19, 2017, which is a Continuation of U.S. patent application Ser. No. 14/263,446, filed Apr. 28, 2014, which issued as U.S. Pat. No. 9,528,124 on Dec. 27, 2016, which claims priority to U.S. Provisional Application No. 61/870,401 filed Aug. 27, 2013, which are hereby incorporated by reference herein.

STATEMENT OF GOVERNMENT SUPPORT

Aspects of the work described herein were supported by grant 1R43RR033149-01A1 from the National Institutes of Health and Biotechnology Risk Assessment Program competitive grant number 2012-33522-19766 from the USDA—National Institute of Food and Agriculture. The United States Government may have certain rights in these inventions.

SEQUENCE LISTING

The instant application contains a Sequence Listing which has been submitted in ASCII format via EFS-Web and is hereby incorporated by reference in its entirety. Said ASCII copy, created Dec. 12, 2018, is named 53545_715_302_SL.txt and is 24,387 bytes in size.

TECHNICAL FIELD

The Technical Field is directed to materials and methods of making genomically modified cells and animals, and research tools for the same.

BACKGROUND

Since the first transgenic pig was created, more than 180 trials have been recorded to genetically engineer livestock in a variety of ways. Animal genetic engineering has traditionally been accomplished by random insertions of expression cassettes which suffered from low efficiency and unpredictable expression, or homologous recombination (efficiency lower than 1 in $10^4$) with linked selection markers.

SUMMARY

Three recent targeted endonuclease technologies, zinc finger nucleases (ZFNs), TAL effector nucleases (TALENs) and clustered regularly interspaced short palindromic repeats/CRISPR associated endonuclease cas9 (CRISPR/Cas9) have been utilized to disrupt gene-function by introducing insertions and/or deletions (indels) into genomes of species mediated by non-homologous end-joining (NHEJ). Particularly, TALEN-induced gene disruption has been demonstrated in various species ranging from model organisms to crops farm animals and humans. However, indels introduced by NHEJ are variable in size and sequence which makes screening for functionally disrupted clones arduous and does not enable precise alterations. TALEN or CRISPR/Cas9 mediated homology-directed repair (HDR) has supported the introduction of defined nucleotide changes in lower eukaryotic models including yeast, zebrafish and, very recently, mice. These are models that allow for long-passage cells or primordial germ cells to be modified to make transgenic animals.

Demonstrated herein are precise, high frequency editing of a variety of genes in about fifteen different working examples in pig, goat, and cattle genomes. In some embodiments, the gene-edits are indistinguishable from alleles that exist within a species or Glade and represent the first demonstration of marker-free, non-meiotic allele introgression. High-efficiency and precise gene-editing was achieved in certain commercially important loci in the genomes of livestock that are useful for agriculture, for research tools, or for biomedical purposes.

These processes have expanded the livestock gene-editing toolbox to include TALEN and CRISPR/Cas9 stimulated homology-directed repair (HDR) using plasmid, rAAV and oligonucleotide templates. One of the examples shows that the bovine POLLED allele was introgressed into homed Holstein fibroblasts. This example demonstrates that various breeds of dairy cattle can be created that do not have horns. And this change can be made without disturbing other genes, or other parts of the genome, of the animals. Single nucleotide alterations or small indels (a term meaning a replacement, insertion and/or deletion) were introduced into about fourteen other genes in pig, goat and cattle fibroblasts using TALEN mRNA and oligonucleotide transfection with efficiencies of 10-50% in populations. Several of the chosen edits mimicked naturally occurring performance enhancing or disease resistance alleles including, for the first time, alteration of single base pairs (bp). Up to 70% of fibroblasts colonies propagated without selection harbored the intended edits of which over one half were homozygous. These efficiencies are so high that these changes can be made without reporters and/or without selection markers. Edited fibroblasts were used to generate pigs with knockout alleles in the DAZL and APC genes to model infertility and colon cancer, respectively. These methods demonstrate meiosis-free intra- and inter-specific introgression of select alleles in livestock cells, large mammals, and livestock for research, agricultural and biomedical applications.

The following patent applications are hereby incorporated herein by reference for all purposes; in case of conflict, the instant specification is controlling: US 2010/0146655, US 2010/0105140, US 2011/0059160, US 2011/0197290, and US 2013/0117870.

BRIEF DESCRIPTIONS OF THE DRAWINGS

Figure 6:
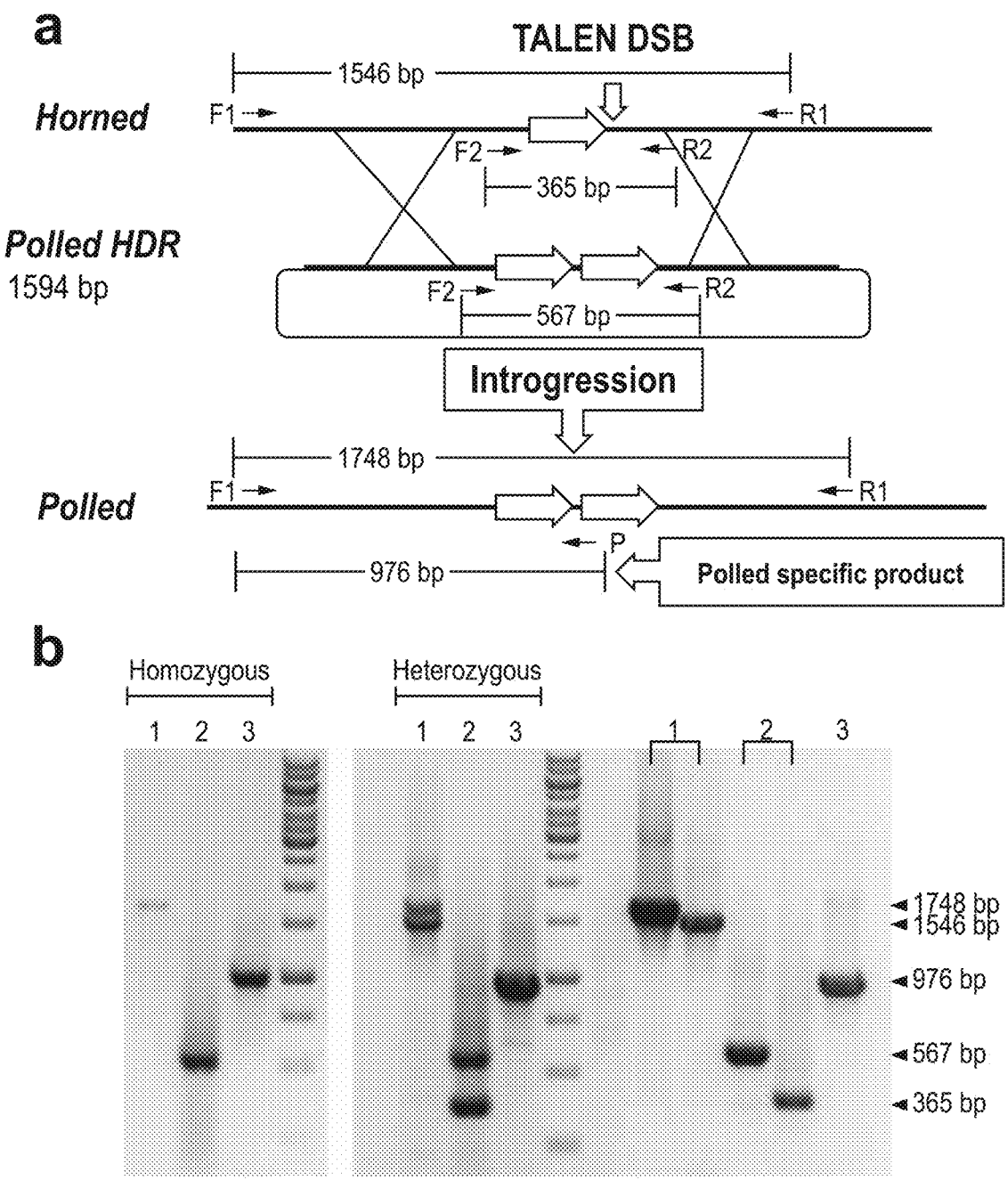

FIG. 6. TALEN-mediated introgression of POLLED. Panel a) A schematic of the strategy to introgress the Polled allele into Holstein (HORNED) cells. The POLLED allele, bottom, is a tandem repeat of 212 bp (horizontal arrow) with a 10 bp deletion (not shown). TALENs were developed to specifically target the HORNED allele (vertical arrow) which could be repaired by homologous recombination using the POLLED HDR plasmid. Panel b) Representative images of colonies with homozygous or heterozygous introgression of POLLED. Three primer sets were used for positive classification of candidate colonies: F1+R1, F2+R2 and F1+P (POLLED specific). Identity of the PCR products was confirmed by sequencing F1+R1 amplicons.

Figure 7:
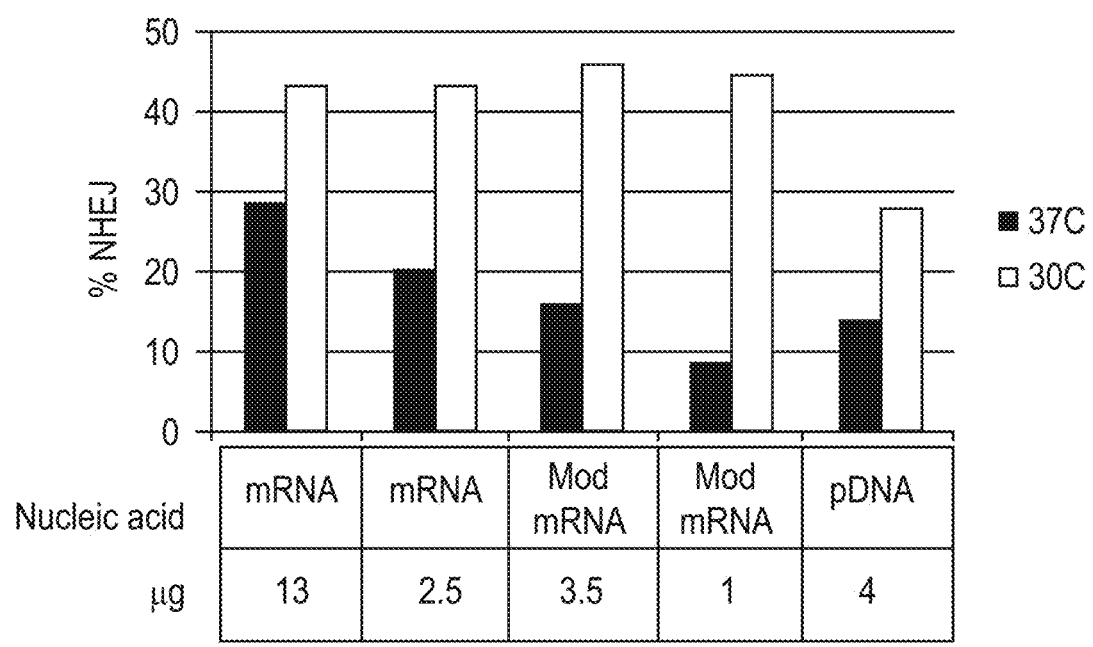

FIG. 7 is a plot of experimental data generated for evaluation of transfected mRNA as a source of TALENs. TALENs were introduced into fibroblasts encoded by either unmodified mRNA, modified mRNA (mod mRNA) or plasmid DNA (pDNA). Two quantities of each TALEN preparation were transfected into cells subsequently cultured 3 days at 30° C. or 37° C. prior to analysis of indels, reported as % NHEJ.

Figure 8A:
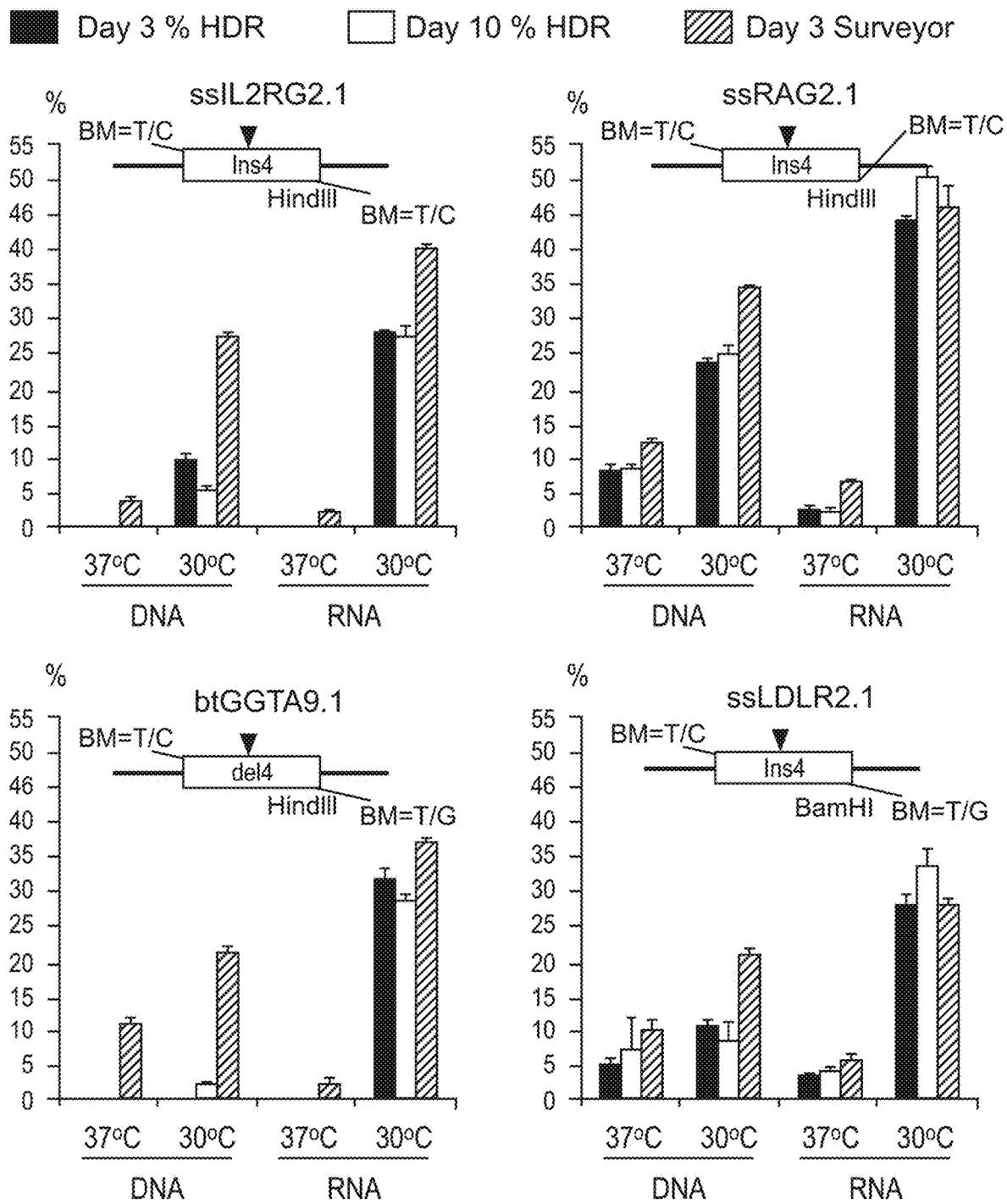

FIG. 8A is a plot showing that an mRNA source of TALENs stimulated efficient and consistent HDR using an oligo donor. Each chart displays results of targeting a specific locus in fibroblasts (e.g., ssIL2RG; "ss" for Sus scrofa and "bt" for Bos taurus) using oligo donor templates and TALENs delivered as plasmid DNA or mRNA. (Insets) Diagrams of the oligo templates, in which the shaded boxes represent the TALEN-binding site and the spacers are shown in white. Each oligo contains either a 4-bp insertion (ins4) or deletion (del4) that introduces a novel restriction site for RFLP analysis. Presumptive BMs replace the conserved −1 thymidine (relative to the TALEN-binding site) with the indicated nucleotide. Fibroblasts were transfected with either TALEN-encoding plasmids (3 µg) or mRNA (1 µg) along with 3 µM of their cognate oligo-homologous template. Cells were then incubated at 37° C. or 30° C. for 3 d before expansion at 37° C. until day 10. TALEN activity was measured by the Surveyor assay at day 3 (Day3 Surveyor), and HDR was measured at days 3 and 10 by RFLP analysis (Day3% HDR and Day10% HDR). Each bar displays the average and SEM from three replicates.

Figure 8B:
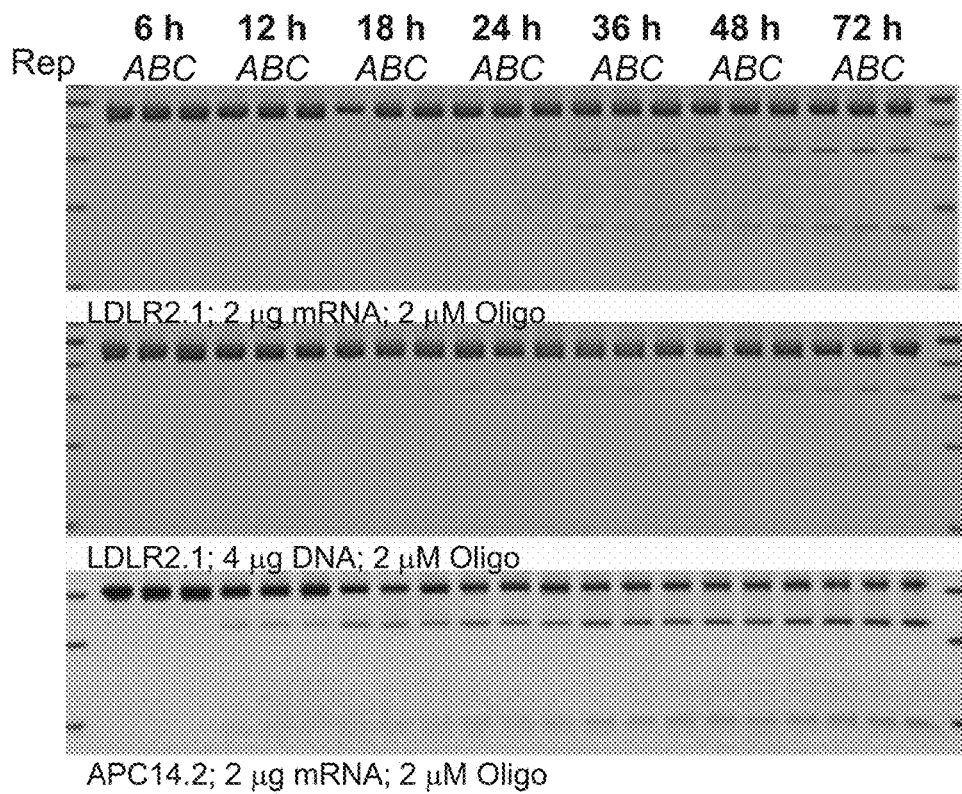
Figure 8B:
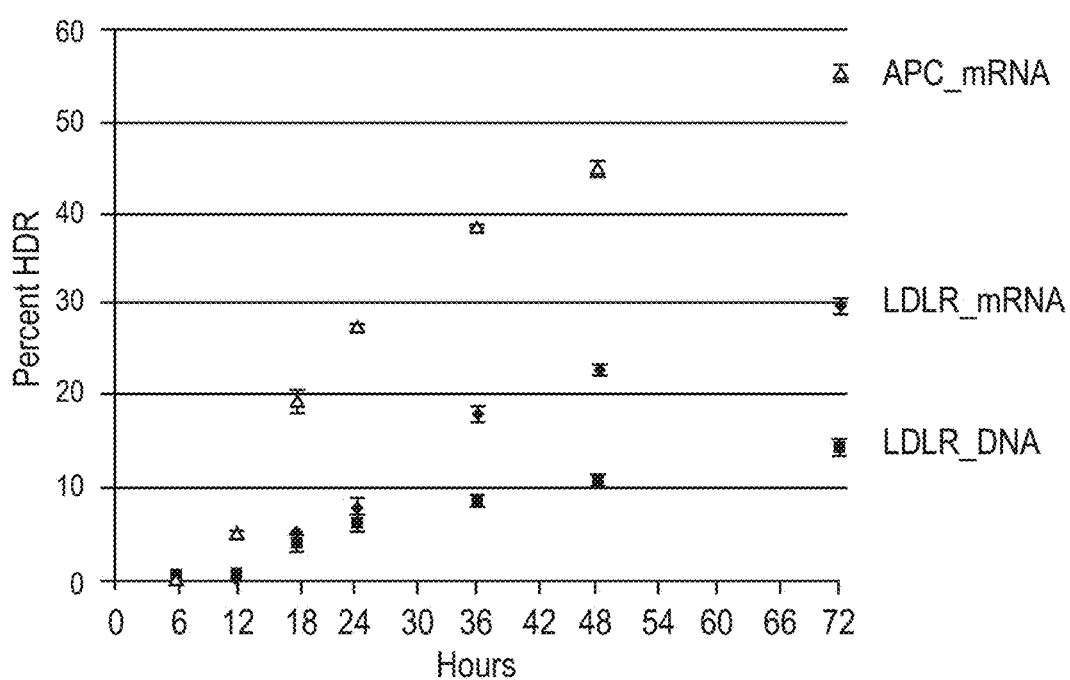

FIG. 8B is a plot of experimental data generated to evaluate kinetics of TALEN induced HDR with oligonucleotide templates. Cells were transfected with either TALEN-encoding mRNA or plasmid DNA and oligos with 4 base pair insertions targeting LDLR or APC genes. Panel a) RFLP analysis on cell populations at indicated time points. Panel b) Results from panel a, were quantified by densitometry and the averages were plotted as a function of time with SEM (n=3). HDR signal first appears 12 hours post-transfection and accumulates over time.

Figure 9:
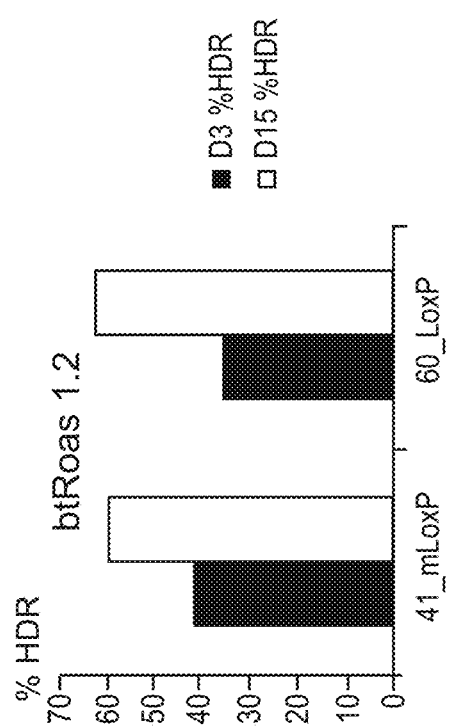
Figure 9:
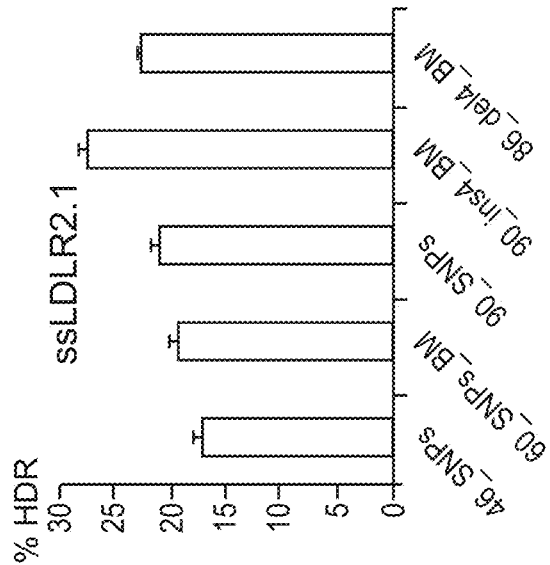

FIG. 9 is a plot of experimental data generated to evaluate influence of mutation type on the frequency of HDR. Panel a) The wildtype ssLDR (SEQ ID NO:1) and sequence of five oligos used to target ssLDR: (from top to bottom: SEQ ID NOS: 2, 3, 4, 5, and 6). TALEN binding sites are indicated in boxed text and the novel BamHI site is underlined. SNPs including BMs and insertions are circled. Panel b) Cells were transfected with LDLR2.1 TALEN mRNA (1 µg) and oligos (2 µM final). HDR at day 3 was determined by RFLP analysis and the average with SEM (n=3) was plotted. Panel c) Cattle cells were transfected with btRosal. 2 TALEN mRNA and either 41_mloxP or 60_loxP oligos (2 µM final). The numbers 41 and 60 refer to the number of homologous bases. Each oligo contains a 34 bp loxP site, either a modified (mloxP) or wild type (loxP) version, in the center of the spacer.

Figure 10:
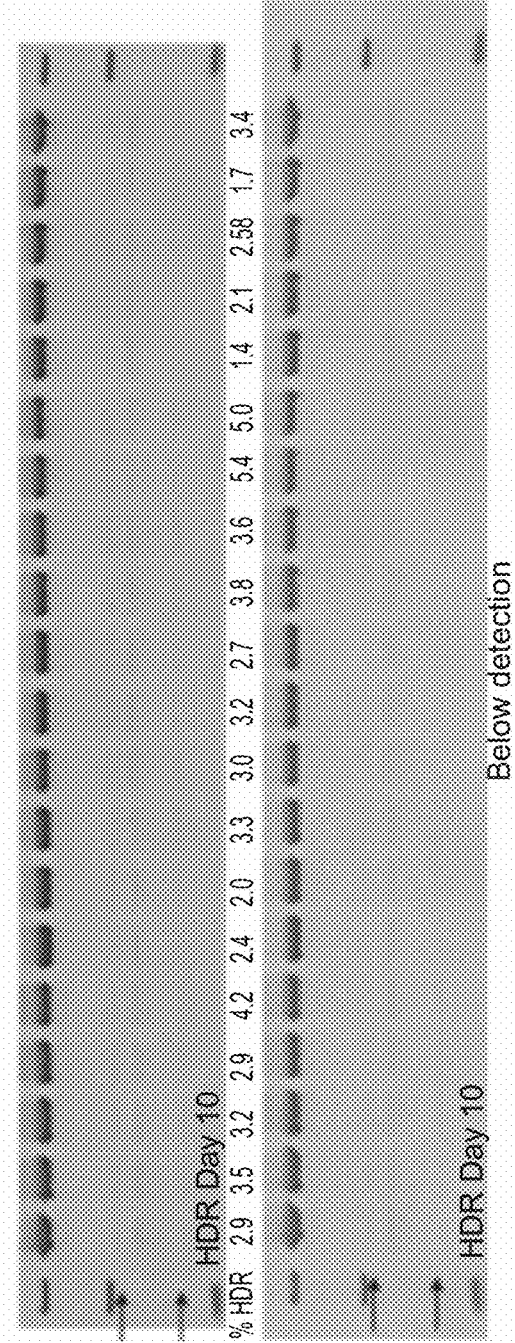

FIG. 10 CRISPR/Cas9 mediated HDR to introgress the p65 S531P mutation from warthogs into conventional swine. Panel a) The S531P missense mutation is caused by a T-C transition at nucleotide 1591 of porcinep65. The S-P HDR template includes the causative TC transition mutation (oversized text) which introduces a novel XmaI site and enables RFLP screening. Panel b) Cells were transfected with S-P-HDR oligos (2 µM), two quantities of plasmid encoding hCas9 (0.5 µg or 2.0 µg); and five quantities of the G2A transcription plasmid (0.05 to 1.0 µg). Cells from each transfection were split 60:40 for culture at 30 and 37° C. respectively for 3 days before prolonged culture at 37° C. until day 10. Surveyor assay revealed activity ranging from 16-30%. Panels c and d) RFLP analysis of cells sampled at days 3 and 10. Expected cleavage products of 191 and 118 bp are indicated by black arrows. The two gRNA sequences are P65_G1S (SEQ ID NO:7) and P65_G2A (SEQ ID NO:8). The wild type porcine p65 is SEQ ID NO:9, shown in alignment with the homology directed repair (HDR) template S-P-HDR (SEQ ID NO:10). The left TALEN sequence and right TALEN sequence to bind p65 DNA are SEQ ID NOs: 11 and 12, respectively.

Figure 11:
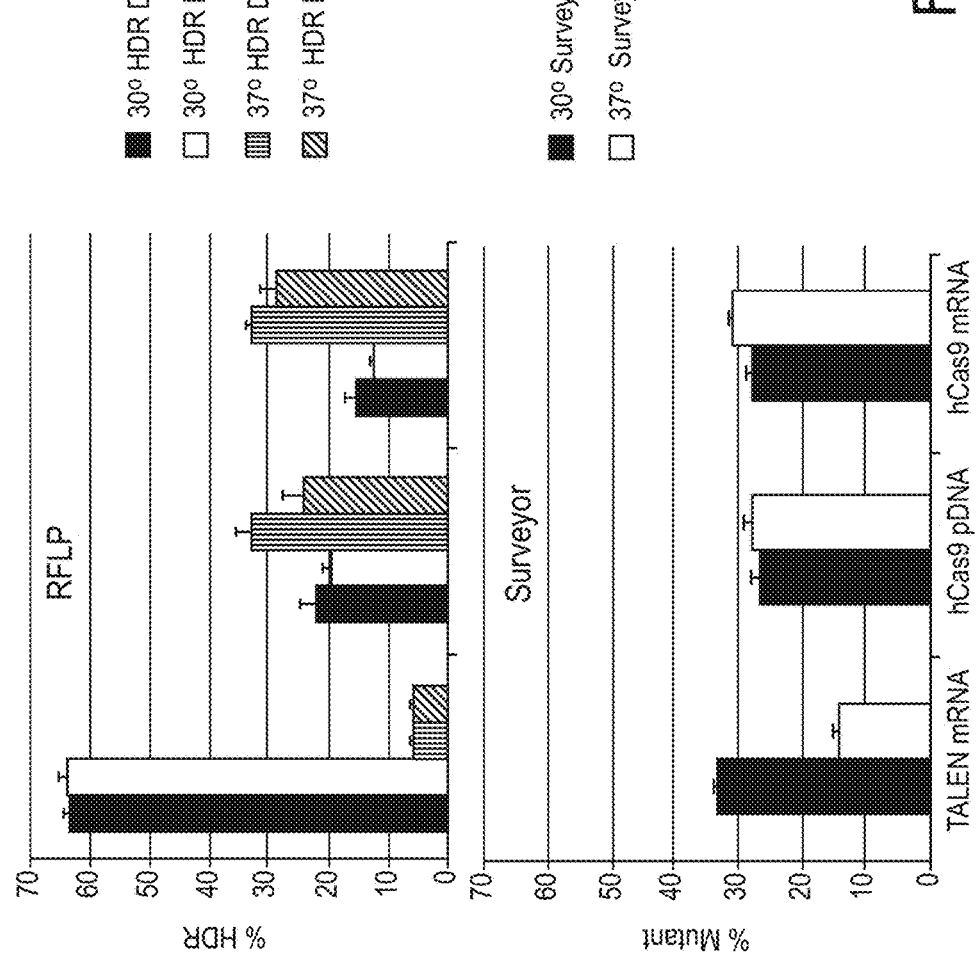
Figure 12:
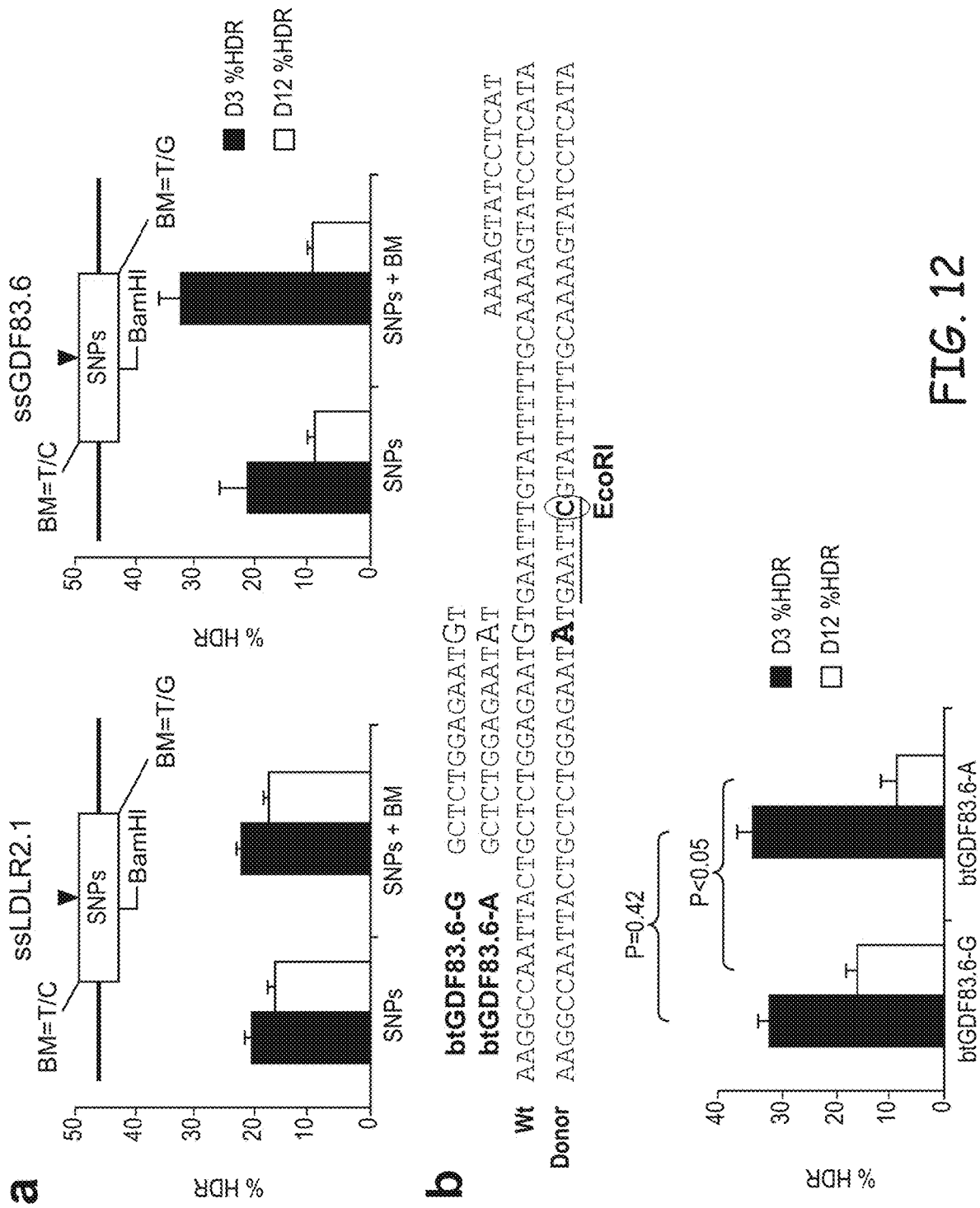

FIG. 11 shows experimental data for comparison of TALENs and CRISPR/Cas9 mediated HDR. Panel a) APC14.2 TALENs (SEQ ID NOS:13 and 14) and the gRNA sequence APC14.2 G1a (SEQ ID NO:15) are shown relative to the wild type APC sequence (SEQ ID NO:16). Below, the HDR oligo (SEQ ID NO:17) is shown which delivers a 4 bp insertion (boxed text) resulting in a novel HindIII site. Cells were transfected with HDR template, and TALEN mRNA, plasmid DNA encoding hCas9 and the gRNA expression plasmid; or mRNA encoding hCas9 plus the gRNA expression plasmid, cultured at either 30 or 37° C. for 3 days before expansion at 37° C. until day 10. Panel b) Charts displaying RFLP and Surveyor assay results FIG. 12 shows experimental data for SNP introgression using oligo donors. Panel a) is a plot of maintenance of HDR alleles with or without blocking mutations (BMs) for pig LDLR and GDF8. Each oligo had the same SNPs/restriction 313 site plus or minus BMs. Average homologous recombination and SEM (n=3) is shown. Panel b) shows results for introgression of myostatin C313Y into Wagyu fibroblasts. The C313Y missense mutation is caused by a G-A transition (indicated by oversized text) at nucleotide 938 of bovine myostatin. The HDR template (labeled donor, SEQ ID NO:18), also includes a T to C transition (circled) to introduce a novel EcoRI site for RFLP screening. Two left TALENs were designed against the locus, btGDF83.6-G (SEQ ID NO:19), targeting the wild type alelle (Wt) (SEQ ID NO:20), and btGDF83.6-A (SEQ ID NO:21), targeting the mutant allele (C313Y); both share a common right TALEN (SEQ ID NO:22). Transfection, culture and measurement were conducted as above. The average and SEM for btGDF83.6-G (n=30) and btGDF83.6-A (n=5) represent twelve and three biological replicates, respectively. A two-sided student's t-test was used to compare averages between groups; the p values are indicated.

Figure 13:
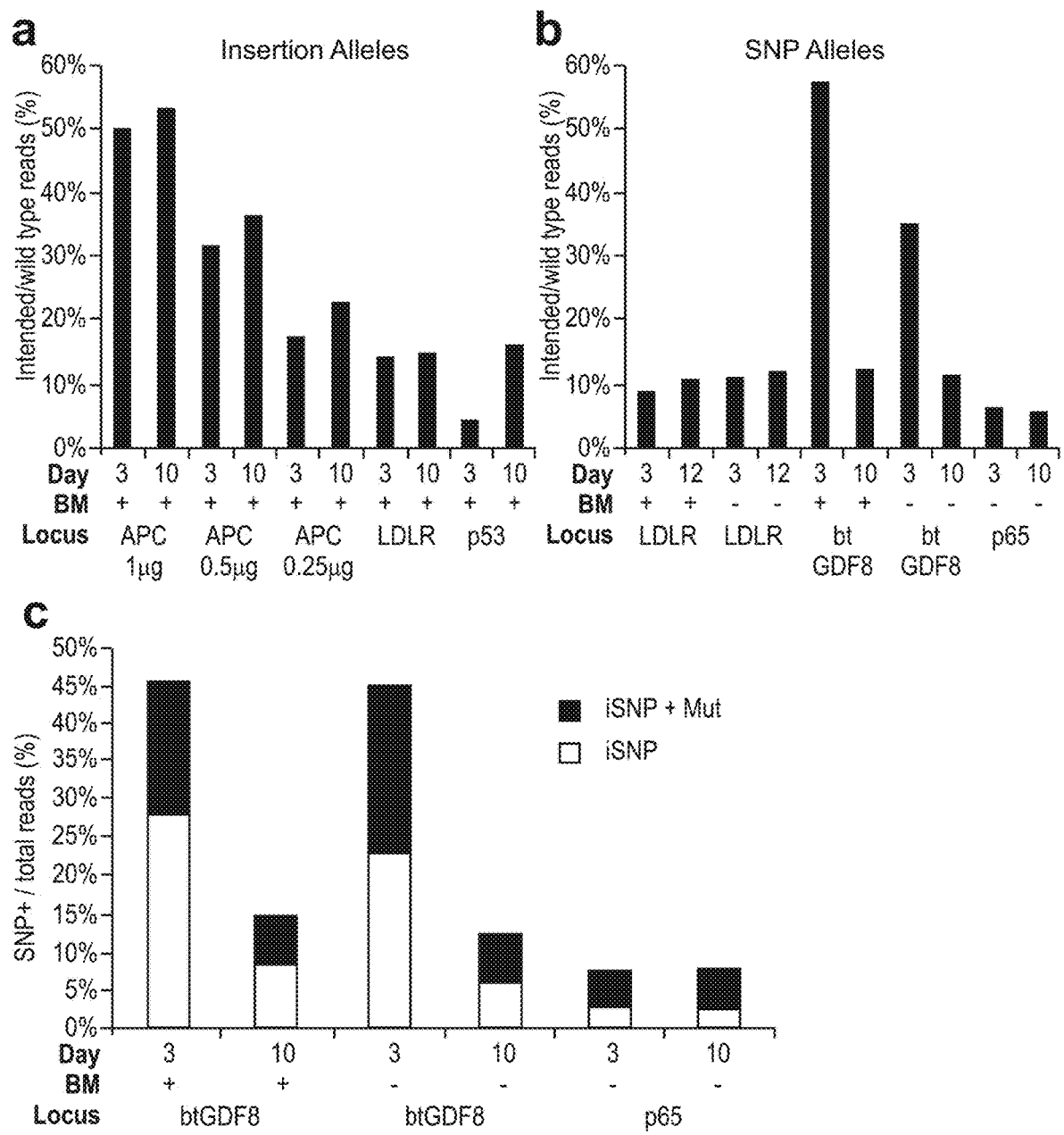

FIG. 13 is a plot that shows results for sequence analysis of TALEN stimulated HDR alleles. The count of perfect, intended HR reads versus the wild type reads is plotted for insertion (panel a) and SNP alleles (panel b). The target locus, time point and whether or not BMs were included in the oligo are indicated. Panel c). Reads from btGDF8 and p65 sorted for incorporation of the target SNP and classified as intended (iSNP) versus those with an additional mutation (iSNP+Mut) and plotted against the total number of reads.

Figure 14:
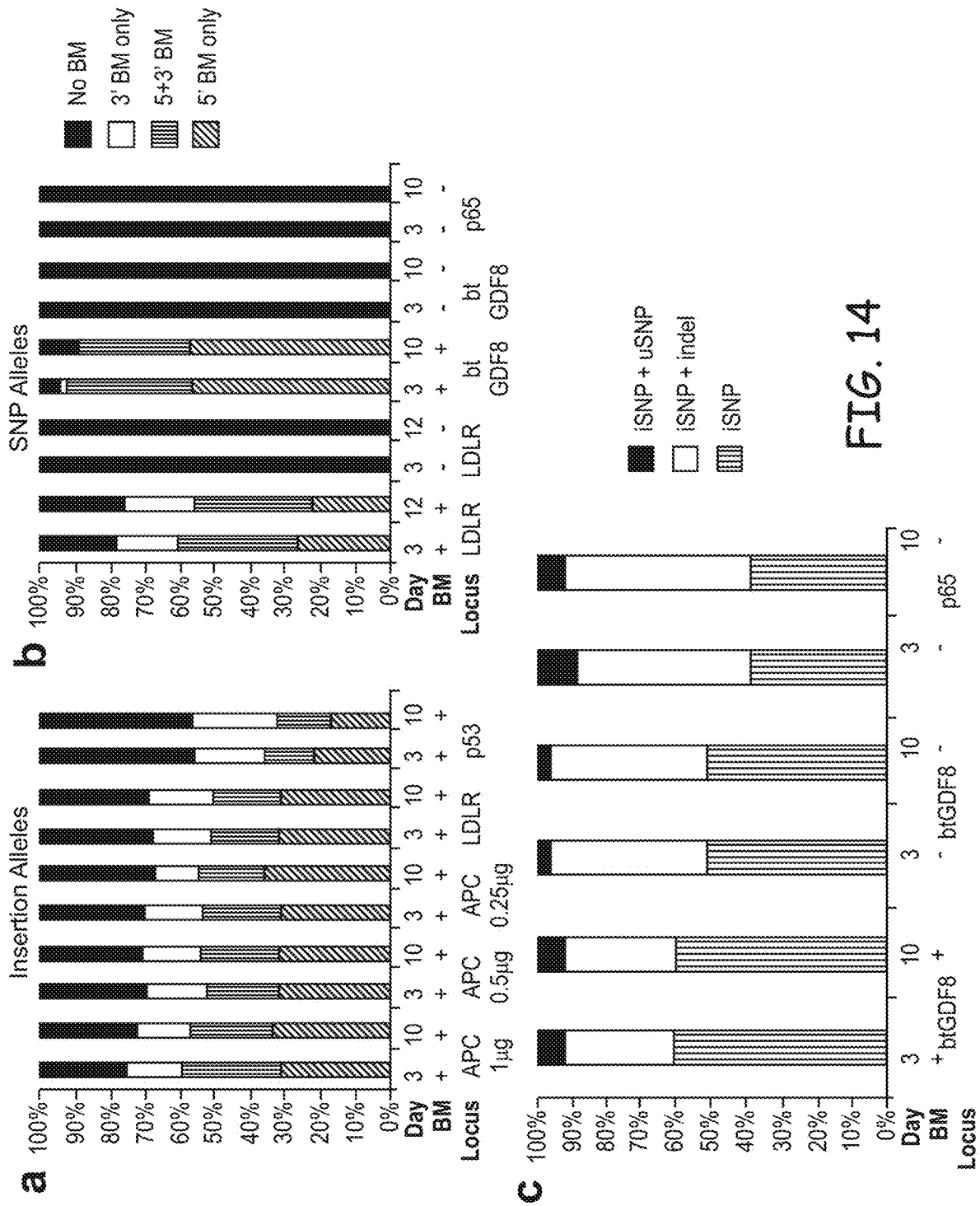

FIG. 14 shows results of sequence analysis of HDR alleles. Sequencing reads containing the correct insertion (Panel a) or SNP allele (Panel b) were analyzed for incorporation of BM. The target locus, time point and whether or not BMs were included in the oligo are indicated below each graph. Panel c). The data of FIG. 13 panel c was further classified by mutation type and compared. Some reads contained only the iSNP, others had a concomitant indel (iSNP+indel), or a concomitant unintended SNP (iSNP+ uSNP).

Figure 15:
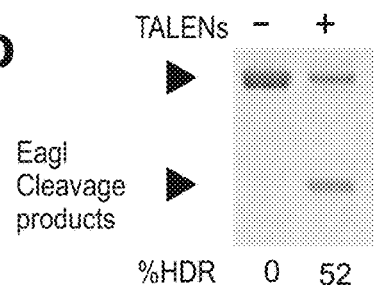
Figure 15:
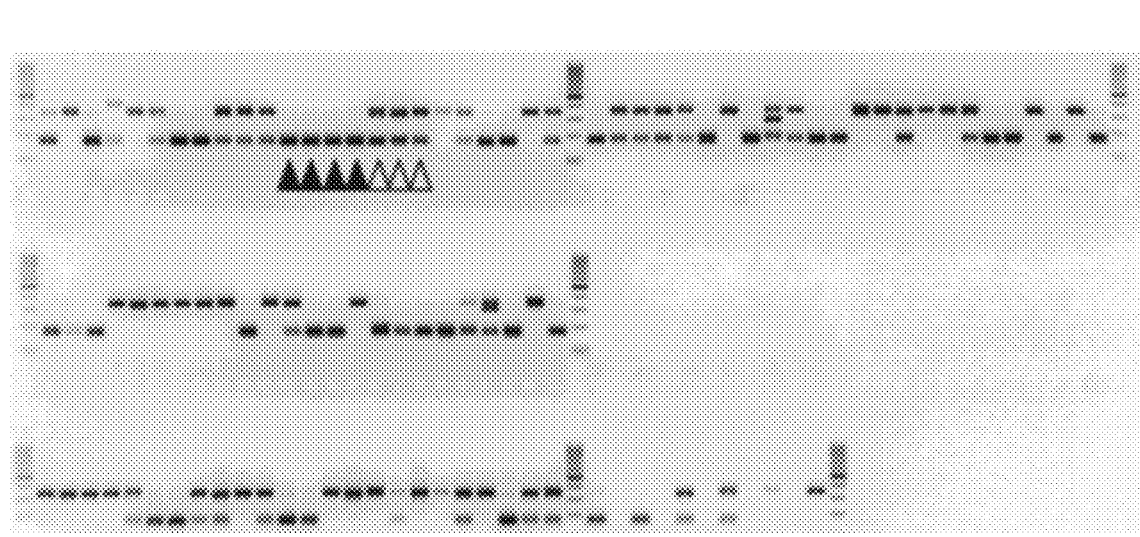

FIG. 15 shows experimental data for multiple SNPs placed in the TALEN DNA-binding site to stabilize HDR alleles in the EIF4GI gene. Panel a) shows a portion of wild type EIF4GI Wt-NL (SEQ ID NO:23) and a pair of TALENs (SEQ ID NOS: 24 and 25) designed to cut the wild type EIF4GI to stimulate homologous recombination. Also aligned to the Wt sequence is the core sequence (SEQ ID NO:26) of the donor oligo, DF-HDR, used to introduce three SNPs (underlined oversized letters) into the genome. The third SNP creates a novel EagI restriction site that was used for RFLP analysis. Pig fibroblasts were transfected with EIF4GI14.1 TALEN mRNA (2 µg) and DF-HDR (2 µM) and then cultured at 30° C. for 3 days prior to analysis and colony propagation. Panel b) shows RFLP analysis on population three days post transfection. Expected product sizes of 344, 177 and 167 bp are indicated by filled triangles. Panel c) shows RFLP assay on isolated cellular clones. Day 3 cells were used to derive monoclonal colonies through dilution cloning. An example of colonies with heterozygous (open triangles) or homozygous (filled triangles) HDR alleles are indicated.

Figure 16:
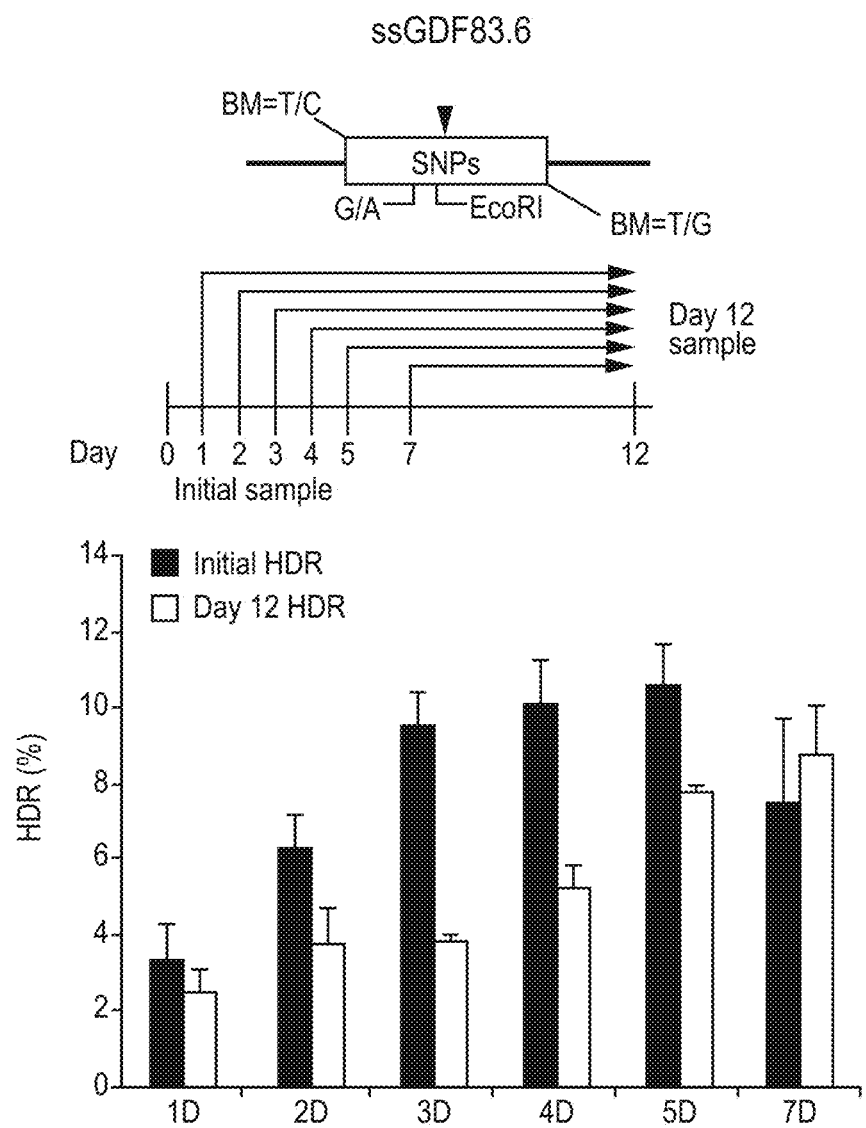

FIG. 16 is a plot of data for hypothermic treatment maintenance of SNP HDR alleles. Pig fibroblasts were transfected with TALEN mRNA (1 µg) and oligos (3 µM). Cells from two independent transfections were pooled for each replicate and evenly distributed into six wells of a 6-well plate and cultured at 30° C. Samples were collected from these populations for RFLP analysis on days 1-7 (minus day 6, 1D to 7D along X-axis) post-transfection and the remaining cells were transferred to 37° C. Samples for each condition were collected again at day 12 for RFLP analysis. The average HDR and SEM (n=3) is shown at the initial collection and once again at day 12.

Figure 17:
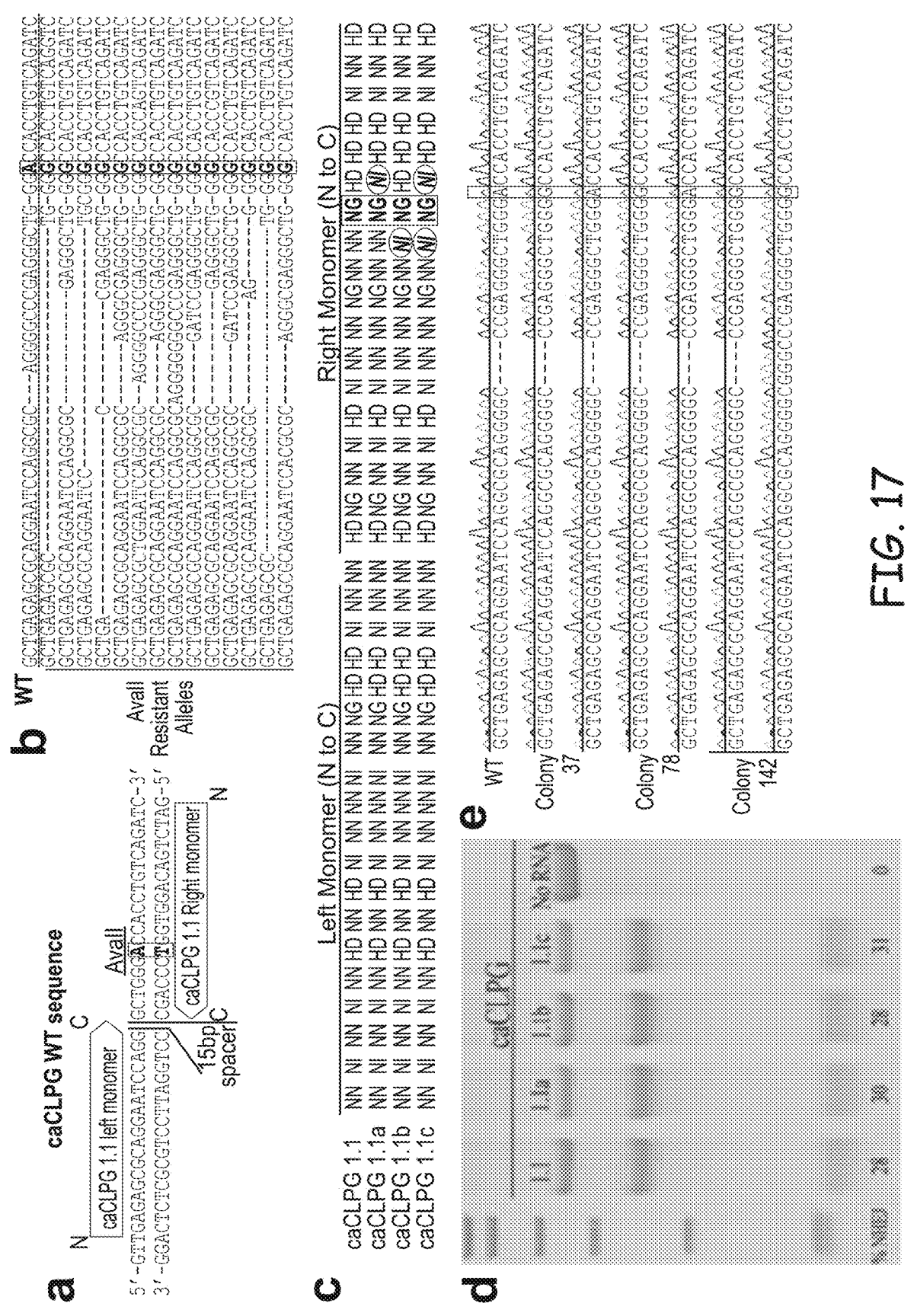

FIG. 17 shows experimental results for TALENs made with intentional RVD mismatches to improve frequency of correct alleles when introducing a SNP. Panel a) shows a TALEN pair (caCLPG 1.1, SEQ ID NOS: 27-29, top to bottom, left to right) designed to target the caCLPG region. Oligo driven HDR was utilized to introduce the desired Adenine to Guanine SNP (the targeted Adenine is boxed). The desired SNP allowed genotyping by a loss of an AvaiI restriction site. Each TALEN monomer is indicated in shading above their respective binding locations. Panel b) A caCLPG wildtpe sequence is shown (SEQ ID NO:31). Each allele of single-cell derived colonies that were resistant to AvaiI were sequenced (fourteen sequences with SEQ ID NOS: 3245, from top to bottom). All of the alleles that contained the SNP of interest (boxed) also contained deletions (marked with dashes in the AvaII Resistant Allele sequences) or insertions (marked with dashes in the WT sequence). In panel c), intentional mismatches (italicized circled text) were introduced into the RVD sequence (represented as protein sequences SEQ ID NOS:46 to 53, top to bottom). The desired SNP (boxed) was in the right monomer of the TALEN. Panel d) shows TALEN activity as measured via a Cell assay. The percent of non-homologous end joining (% NHEJ) is indicated for each was measured. Panel e) shows both an alignment of a caCLPG wildtpe sequence is shown (SEQ ID NO:60) with sequenced alleles of AvaiI-resistant single-cell derived colonies produced with caCLPG 1.1c (six sequences, with SEQ ID NOS: 54 to 59, top to bottom). The desired SNP is boxed. Colony 37 and 78 were heterozygous for the desired SNP and showed no additional indels. Colony 142 was homozygous for the desired SNP, but contained a 4 bp insertion on one allele.

Figure 18:
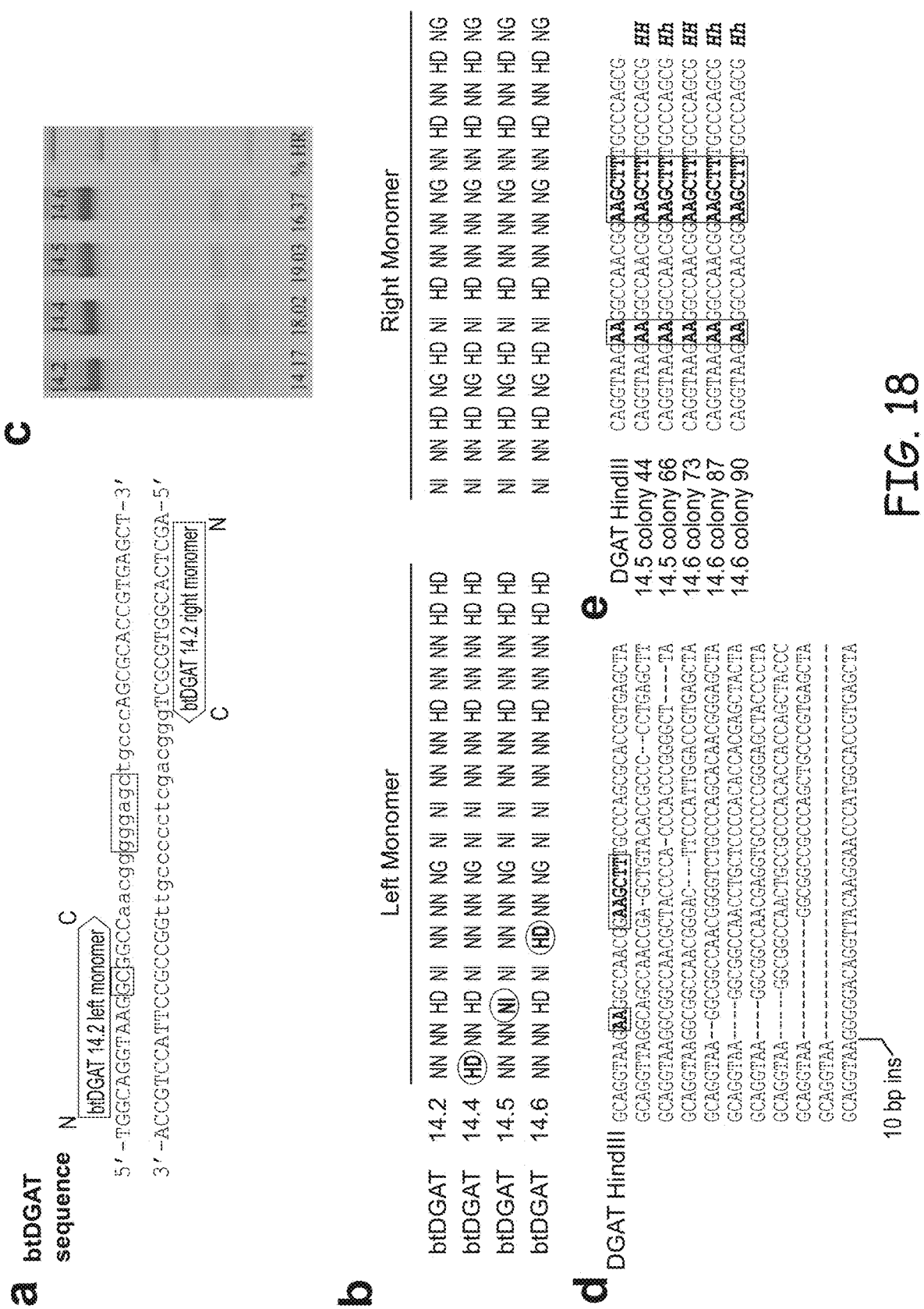

FIG. 18 shows results for experiments to introgress a SNP with and without a mismatch in the targeting endonuclease. Panel a) shows a schematic of the bovine DGAT sequence around K323A (SEQ ID NOs: 61 and 62). The grey arrows represent the TALEN monomers where they bind to the DGAT sequence. The left arm consists of 16 RVDs, the right arm consists of 15 RVDs, and the spacer is 16 base pairs long. The GC and gga gct, boxed, are the targeted base pairs. The DGAT oligo converts the GC to an AA to create the desired DGAT mutant. As a marker for HDR, the boxed GGGAGC is converted to AAGCTT that creates a novel HindIII restriction site. Since this change is in the spacer, it should not affect TALEN binding as to not interfere with the intentional mismatch results. Panel b) DGAT TALEN RVD sequences (from top to bottom: SEQ ID NOs:63 to 70). btDGAT 14.2 contains no intentional mismatches in the RVDs. btDGAT 14.4, 14.5, and 14.6 each contain one intentional RVD mismatch at either position 1, 3, or 5 of the left TALEN monomer (circled). Panel c) Bovine fibroblasts were transfected with 1 ug of talen and 0.4 nmoles of oligo. Three days after transfection cells were lysed, the DGAT sequence was amplified by PCR, digested with HindIII and ran on an acrylamide gel. The percent efficiency of HDR was determined by densitometry (HR). Panel d) Sequence analysis of colonies produce with the original 14.2 TALENs. Of twelve colonies, none that were positive for the HindIII RFLP contained the desired mutation due to indels overlapping the site. (From top to bottom, SEQ ID NOs: 71 to 79, 81). Panel e) Colonies derived from TALENs 14.5 and 14.6 produced the correct DGAT mutation and HindIII restriction site. These two TALEN pairs produced a total of two homozygous (HH) and three heterozygous (Hh) colonies. TALEN 14.4 did not produce any colonies with the correct DGAT mutation (data not shown), from top to bottom, SEQ ID NOs: 82 to 87.

Figure 19:
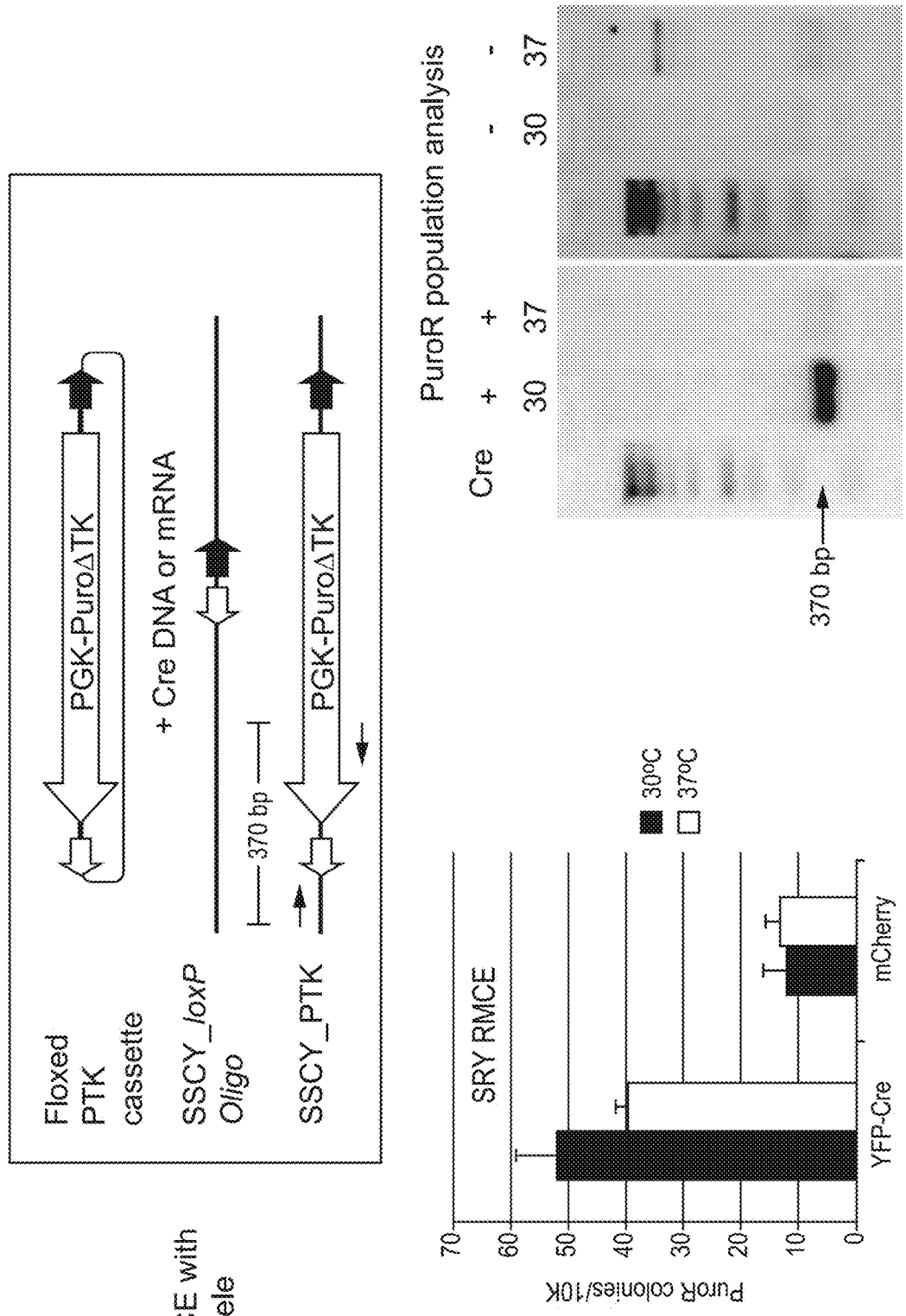

FIG. 19 sets forth the process of TALEN-HDR/RMCE. The floxed cassette is transfected along with TALENs compatible with the oligo, the loxP oligo and a source of Cre recombinase. The bar graph shows the number of puromycin resistant colonies produced by this method when YFC-Cre versus mCherry was included in the transfection. To confirm targeting to the SRY locus, PCR was conducted across the predicted junction (shown) will result in a 370 bp product. This product is apparent only when Cre is included.

DETAILED DESCRIPTION

Gene editing tools such as targeting endonucleases are useful for making genetically modified animals. Using these tools to change a native allele at only one base is difficult or impossible using conventional processes. New techniques are described herein for making these edits at a single base, or a plurality of single-base edits. These processes are useful for introgression of an allele that differs only by a single nucleotide polymorphism (SNP) or a plurality of SNPs. The ability to introgress SNPs from one breed or species into another is believed to create important new opportunities. The term SNP refers to a difference of one base at the same relative site when two alleles are aligned and compared; herein, the term is also used in some contexts to mean a single base change.

Figure 1:
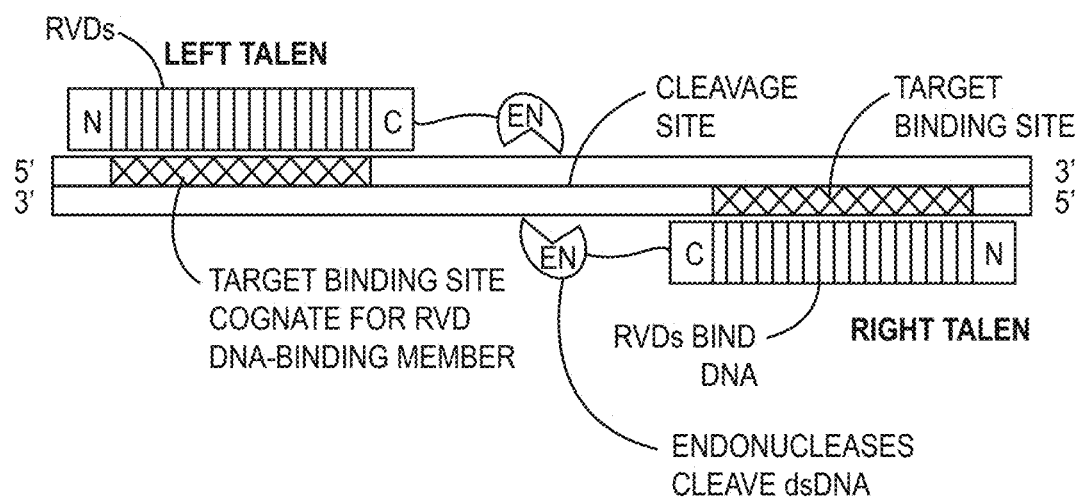
FIG. 1 illustrates a general process of using a TAL-effector endonuclease (TALEN).

FIG. 1 illustrates a general process of using a TAL-effector endonuclease (TALEN). A TALEN pair is depicted;

other processes use a single TALEN. A target site is chosen in a dsDNA. A left and a right TALEN are made with TAL-effector repeat sequences that include Repeat Variable Diresidues (RVDs) chosen to match the targeted site. The RVDs are designed to match their cognate sequences. An endonuclease, such as FoId, is attached with a spacer to the TAL-effector portion. A left TALEN and a right TALEN are designed in light of the homologous base pairing of dsDNA. The TALENs are introduced into the cell and specifically bind at the intended target sites. They are typically targeted to a gene, although the actual binding site may be at a promoter, intron, exon, or other site as appropriate to disrupt the gene or change its sequence for other purposes. The TALENs make a double strand break in the DNA, which is then repaired by DNA repair machinery in the cell. When a DNA with substantial homology to DNA around the site of the break is present, the cellular machinery can use that DNA as a template to guide the repair process; this process is homology directed repair and the guide is a HDR template. In the absence of a template, the cell might repair itself successfully or create an indel.

Figure 2:
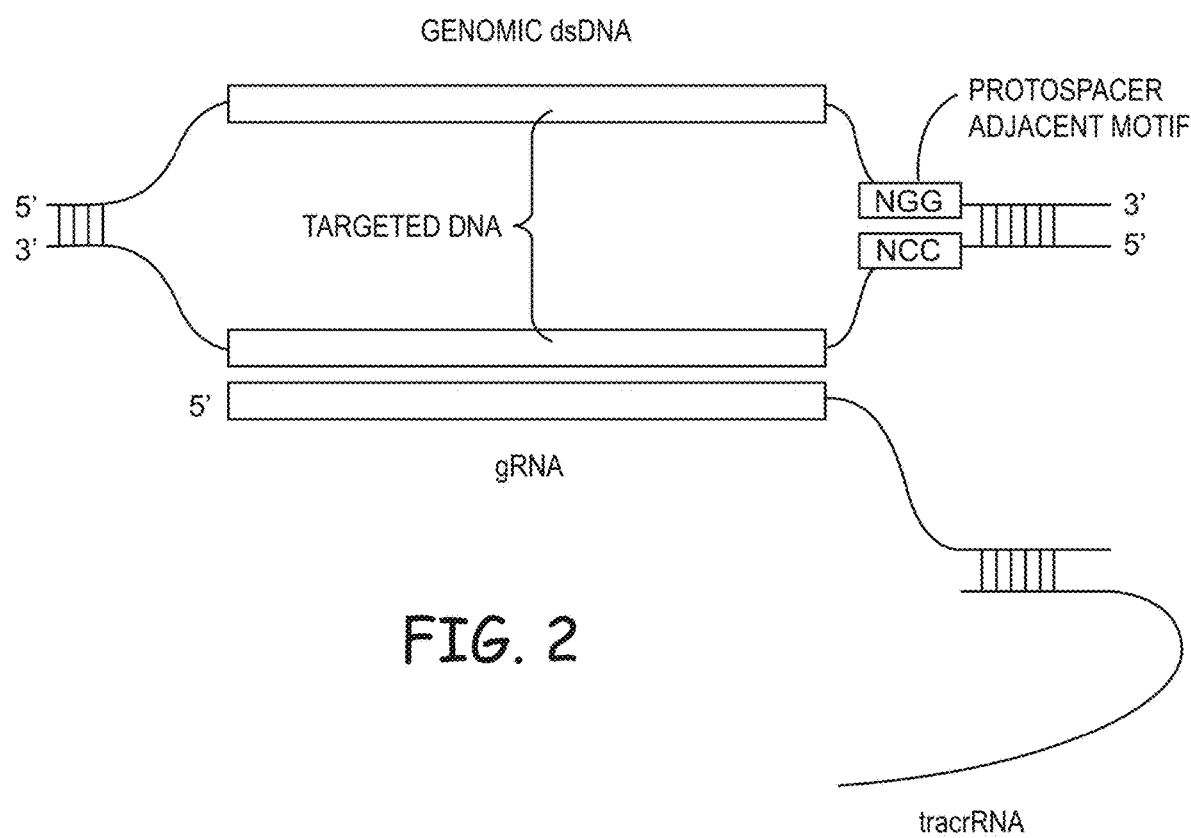
FIG. 2 illustrates a general process of using a Cas9/CRISPR endonuclease (an RNA-guided endonuclease).

FIG. 2 illustrates a general process of using a Cas9/CRISPR endonuclease. A target DNA is chosen that is near the protospacer adjacent motif. A tracrRNA and spacer RNA can be combined into a "single-guide RNA" molecule that complexes both with Cas9 and a target sequence, in which it introduces a double stranded sequence-specific break. Vectors to express Cas9 with a gRNA-tracrRNA are known and readily available. As with TALENs, cellular repair machinery might repair the dsDNA break perfectly or with an indel. If a suitable HDR template is present, the template can guide the repair and create changes in the native DNA.

Figure 3:
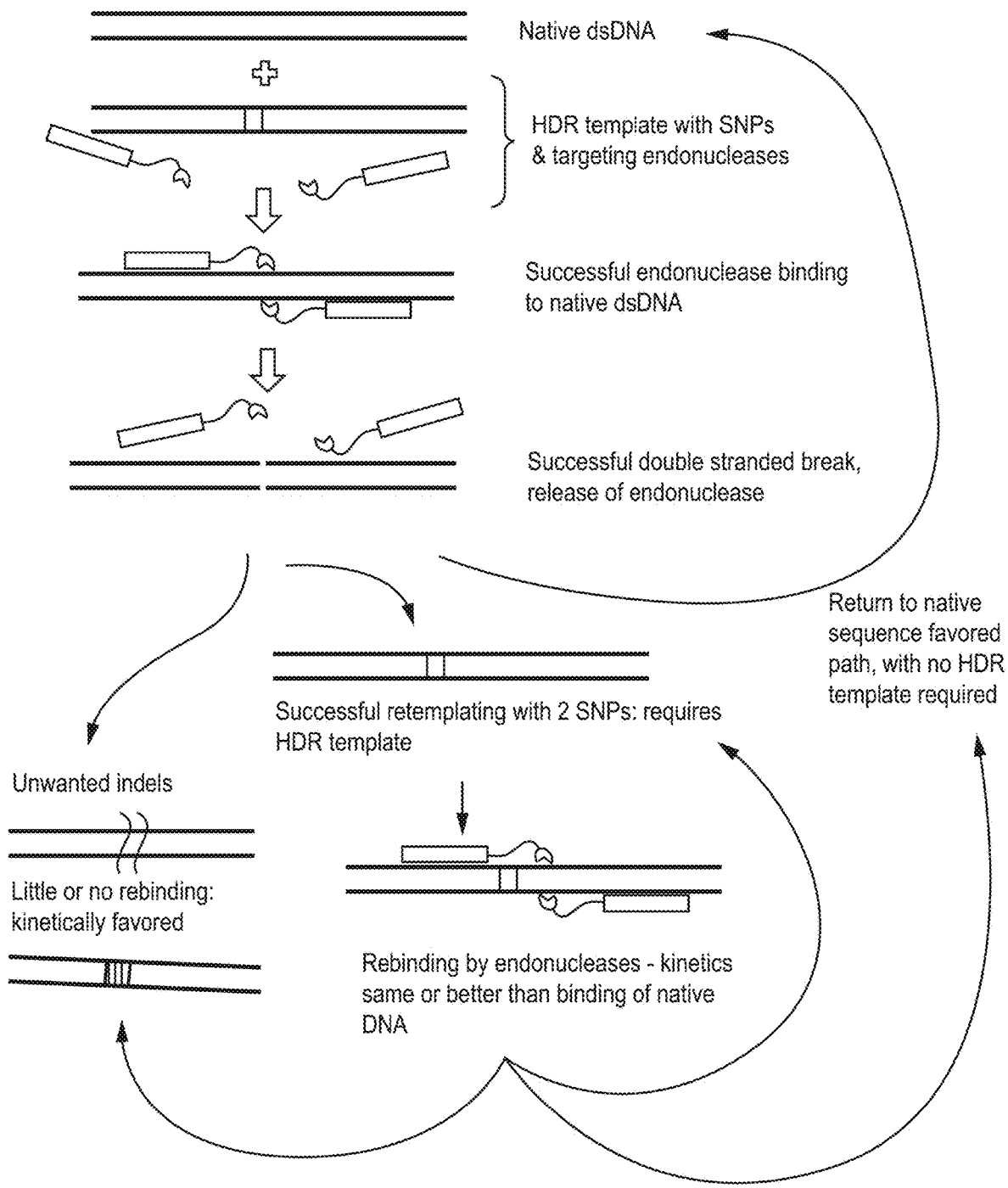
FIG. 3 illustrates the theory of operation for TALENs that explains why they are generally ineffective for making SNP changes; similar processes apply to other targeted endonucleases.

FIG. 3 illustrates a theory of operation for targeted endonucleases that explains why they are generally ineffective for making SNP changes; similar processes apply to RNA-guided endonucleases. A native double stranded DNA (dsDNA) is illustrated that is being exposed to a TALENs pair and a homology directed repair (HDR) template. The TALENs have to bind at the targeted gene. Then they can cut the native DNA and be released. After being cut, the native DNA might be imperfectly repaired so that it has an indel. Even indels of a few bases can be enough to greatly reduce rebinding of the repaired DNA by the TALENs. Another possibility is that the repair process will return the cut DNA to its native sequence. Or there might be a successful HDR-driven change in the sequence so it is the same as the HDR template. The altered DNA is, however, subject to being rebound and recut by the TALENs. In fact, the cut DNA is already uncoiled and available for cutting whereas native DNA might not be as available. The kinetics of editing require participation by the HDR template whereas repair of a break by non homologus end joining (NHEJ) does not. Therefore it is believed that the kinetics of modification drive the editing process to unwanted outcomes when SNPs or other small changes to the native gene are desired.

Figure 4:
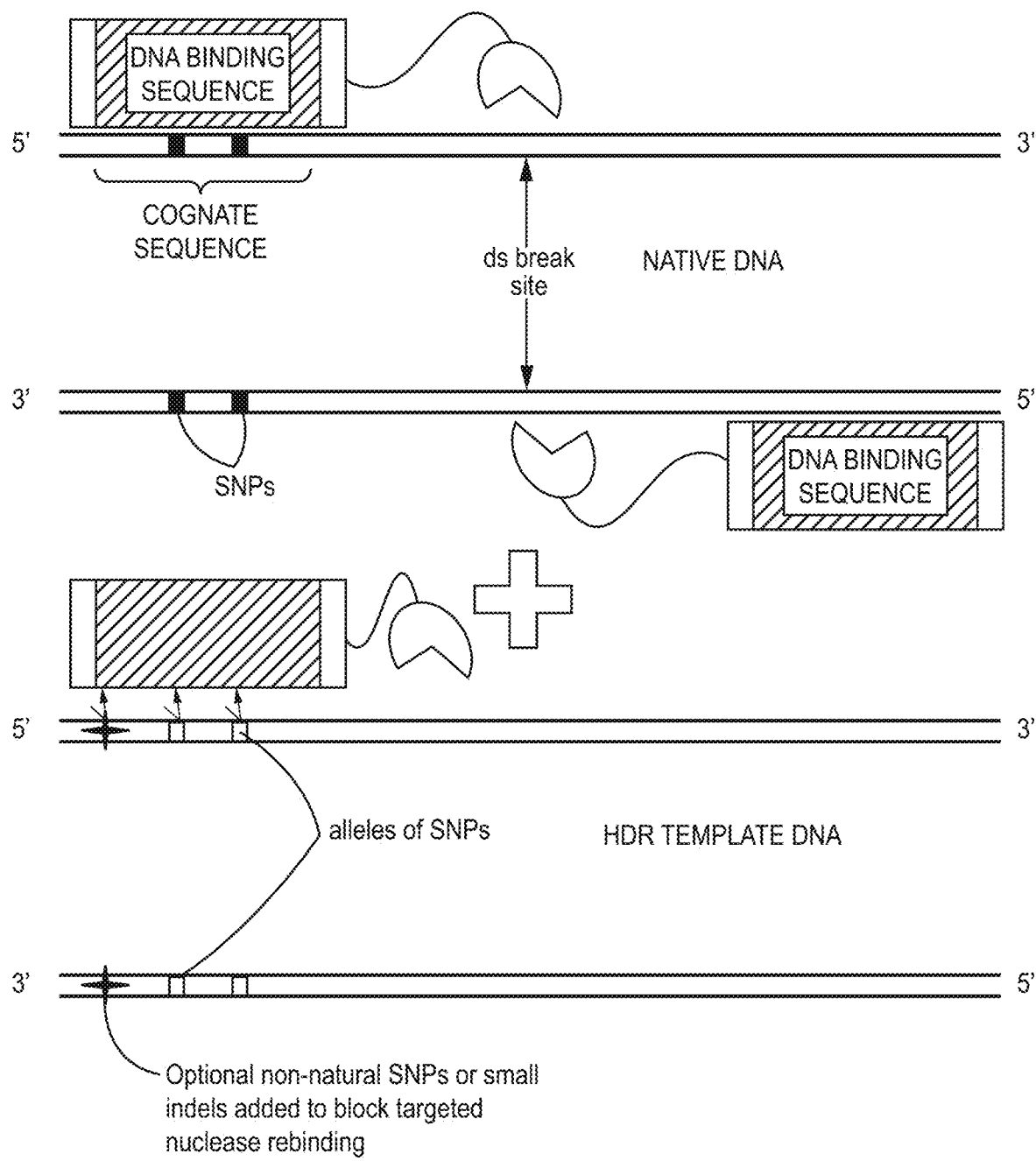
FIG. 4 illustrates a general method of making and using targeting endonucleases that is effective to make an SNP edit.

FIG. 4 illustrates a general process of making and using targeting endonucleases that is effective to make an SNP edit. One strategy that is effective is to design the targeting endonucleases so that the desired SNPs (or other altered residues) are in the cognate region of the DNA binding portion of the endonuclease system. The HDR template guides a change in the SNPs so that the desired SNPs are mismatches with the RVDs or other DNA-binding portion.

Further, changes may optionally be added to the HDR template to create further mismatches. An embodiment of designing the HDR sequence to reduce specific binding of the DNA-binding member comprises placing a mismatch in the HDR template sequence as aligned with the endogenous chromosomal DNA. The mismatch may include one or more of: an insertion, a deletion, a substitution, an insertion of 1-6 residues and/or a deletion of 1-6 residues, a substitution of 1-60 residues, only one SNP, one or more SNPs; artisans will immediately appreciate that all values and ranges within the expressly stated limits are contemplated. In the context of introgression of a naturally-occurring allele, the mismatches may be in addition to those that are present in the naturally-occurring allele.

Figure 5:
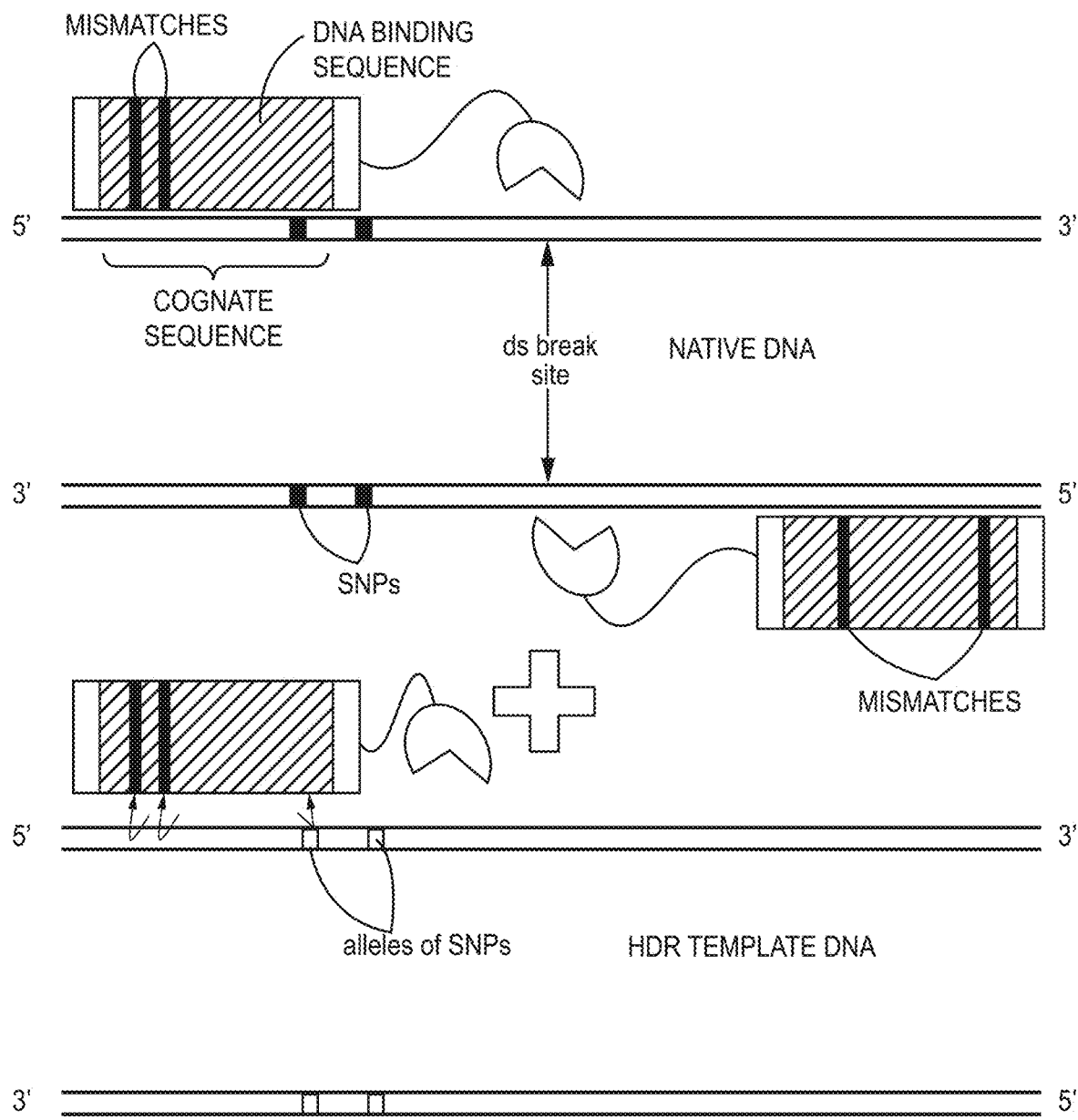
FIG. 5 illustrates another general method of making and using targeting endonucleases that is effective to make an SNP edit.

FIG. 5 illustrates another general process of making and using targeting endonucleases that is effective to make an SNP edit, or to make larger edits. The DNA-binding sequences of one (and/or both if applicable) of the targeting endonucleases are made with intentional mismatches with the endogenous DNA. In TALENs, the RVDs are chosen to be mismatches. In CRISPR/Cas9 the guide sequence has one or more mismatches. The desired SNPs, referring to the changes that are the biological goal of the introgression process, may be inside and/or outside of the DNA-binding domain. Creating a reduction in binding seemed to be an improbable approach. But, in fact, experiments showed that driving efficiency down at the initial binding stage was helpful.

The embodiments of FIGS. 4 and 5 may be combined. The TALENs or CRISPR/Cas9 can be designed with a mismatch to reduce binding to endogenous DNA and/or the HDR template can introduce a mismatch to reduce specific binding to the targeting endonucleases and/or the site on the endogenous DNA can be chosen to create a mismatch in the cognate binding sequences for the DNA-binding domains. In the context of introgression of a naturally-occurring allele, the mismatches may be in addition to those that are present in the naturally-occurring allele. So the method would include selecting an allele found in nature, making an HDR template that comprises at least a portion of that allele, and making one or more of the mismatches in the HDR template and/or in the DNA-binding domain.

Intro Gression of POLLED Allele

To protect the welfare of dairy farm operators and cattle, horns are routinely manually removed from the majority of dairy cattle in the U.S., Europe, and in other regions. De-horning is painful, elicits a temporary elevation in animal stress, adds expense to animal production and, despite the intent of protecting animals from subsequent injury, the practice is viewed by some as inhumane. Some beef breeds are naturally horn-free (e.g., Angus), a trait referred to as POLLED that is dominant. The techniques set forth herein improve animal well-being by providing animals that do not have to undergo dehorning. Two allelic variants conferring polledness have recently been identified on chromosome 1. Dairy cows with either of these mutations are rare and generally rank much lower on the dairy genetic selection indices than their horned counterparts. Meiotic introgression of the POLLED allele into horned breeds can be accomplished by traditional crossbreeding, but the genetic merit of crossbred animals would suffer and require many lengthy generations of selective breeding to restore to productivity.

It is possible, however, to create polledness in animals, and to do so without disturbing the animals' genome. The non-meiotic introgression of the Celtic POLLED allele (duplication of 212 bp that replaces 10 bp) was achieved in fibroblasts derived from horned dairy bulls. A plasmid HDR template containing a 1594 bp fragment including the Celtic POLLED allele was taken from the Angus breed (FIG. 6 panel a). TALENs were designed such that they could cleave the HORNED allele but leave the POLLED allele unaffected. Surprisingly, this experiment showed that one pair of TALENs delivered as mRNA had similar activity compared to plasmid expression cassettes (FIG. 7), Accordingly, experiments were performed that delivered TALENs as mRNA to eliminate the possible genomic integration of TALEN expression plasmids. Five of 226 colonies (2%) passed each PCR test shown in FIG. 6 panel b to confirm introgression of POLLED. Three of the five clones were homozygous for POLLED introgression and confirmed by sequencing to be 100% identical to the intended allele. U.S. Ser. No. 14/154,906 filed Jan. 14, 2014, which is hereby incorporated by reference herein, provides additional information regarding polledness.

Allele Introgression in Pig, Goat and Cattle Genome

While plasmid templates were effective for introgression of POLLED and GDF8, the inventors believe that many desirable alleles correspond to SNPs. A first set of experiments used oligonucleotide templates that had an overlap in their cognate TALEN-binding sites and that also introduced a 4 bp indel into the spacer region for restriction fragment length polymorphism (RFLP) analysis. Primary fibroblasts were transfected with plasmid- or mRNA-encoded TALENs plus oligo templates and incubated 3 days at either 30 or 37° C. TALENs delivered as mRNA consistently outperformed plasmid in cells incubated at 30° C. (FIG. 8A). Despite appreciable levels of TALEN activity measured by the SURVEYOR assay, HDR was consistently higher (>2-fold) when TALENs were delivered as mRNA compared to plasmids. This observation was surprising, and it was speculated that could have been a result of favorable kinetics; e.g., TALENs from mRNA were more rapidly translated allowing utilization of the template prior to oligo degradation. However, a time-course experiment showed little difference in the onset of HDR between TALENs encoded by plasmid versus mRNA (FIG. 8B). Among replicates using TALEN mRNA at 30° C., the levels of cumulative mutation and total HDR were similar, suggesting the majority of mutant alleles corresponded to the intended introgression.

In previous studies, TALEN-induced indels declined 50-90% after extended culture unless selection processes or markers were used (Carlson, D. F. et al. Efficient TALEN-mediated gene knockout in livestock, *Proceedings of the National Academy of Sciences*, 109:17382-17387 (2012), herein "Carlson 2012"). In other words, even when indels could be made, they were often not stable and a selection marker process had to be used to identify stable changes. In contrast, it was observed herein that HDR levels at four loci were roughly equivalent when measured at days 3 and 10 without selective enrichment, indicating that these HDR indel alleles were stable in culture (FIG. 8A). The consistently high rate (25-50%) and stability of gene edits at all four loci suggested that edited cells should be recoverable by dilution cloning without selective enrichment, reporters or selection markers. Further experimental work involving analysis of about 1,000 colonies for defined indel alleles in eight separate loci revealed a recovery rate of 10-65% (average 42%) where up to 32% of the colonies are homozygous for the intended edit (Table 1). The data shows that introducing TALENs as mRNA into the cell is helpful for efficiency and stability; extended culture times at 30° C. were also helpful.

The term reporter, as used herein, refers to genes or transgenes that encode reporters and selection markers. The term selection marker, as used herein, refers to a genetically expressed biomolecule that confers a trait that permits isolation by either positive or negative survival selection criteria. The reporter may be, e.g., a fluorescent marker, e.g., green fluorescent protein and yellow fluorescent protein. The reporter may be a selection marker, e.g., puromycin, ganciclovir, adenosine deaminase (ADA), aminoglycoside phosphotransferase (neo, G418, APH), dihydrofolate reductase (DHFR), hygromycin-B-phosphtransferase, thymidine kinase (TK), or xanthin-guanine phosphoribosyltransferase (XGPRT). Phenotypic markers are markers based on discernible physical traits (e.g., epitopes or color), growth rate, and/or viability.

Differential Stability of Gene-Edits

It was not known if it was possible to have Introgression of stable SNPs by NHEJ or HDR. As indicated in Table 1, both day-3 levels of HDR (7-18%) and the isolation of cellular clones with the intended SNP alleles (3-15%) within cattle and swine GDF8 or pig p65 was significantly lower than for indel alleles, where HDR ranged from 10 to about 50%. This data suggested a hypothesis that indels were more stable than SNP because the introduction or elimination of at least 4 bp in the TALEN spacer region would be expected to reduce re-cleavage of the locus, consistent with constraints on TALEN spacer length. And even a 4 bp insertion allele was more efficient than SNP alleles, based comparison of HDR frequencies with oligo within the same locus suggested (FIG. 9).

This hypothesis also explained why sequence analysis revealed that nearly half of the isolated SNP-positive colonies for GDF8 or pigp65 harbored concomitant indels expected to change TALEN spacing. Regardless, it was possible to recover colonies with homozygous conversion of G938A in GDF8 (both pigs and cattle) and T1591C in pig p65 at up to nearly a 5 percent level without any additional changes to the locus (Table 1). It was also possible to introgress small polymorphisms for the sheep FecB and Callipyge loci into the goat genome. This ability to precisely alter a single nucleotide or 1-3 nucleotides is surprising as well as significant. As a comparison, it was also possible to design CRISPR gRNAs that overlapped the T1591C site ofp65 and to compare introgression using the two platforms. Despite efficient production of DSB at the intended site, CRISPR/Cas9-mediated HDR was lower than 6 percent at day-3 and below detection at day-10 (FIG. 10). Recovery of modified clones with CRISPR-mediated HDR was also lower than with TALENs even though the TALENcleavage site was 35 bp away from the SNP site (Table 1). Analysis of CRISPR/Cas9 induced targeting at a second locus, ssAPC14.2, was much more efficient, but still did not reach the level of HDR induced by TALENs at this site, circa 30 versus 60% (FIG. 11).

Strategies for Introgression of Alleles and for Stabilizing Introgressed SNP Alleles Given the conservation of the 5'-thymidine nucleotide immediately preceding TAL-binding sites, it was reasoned that altering these bases in the oligo HDR template (referred to as blocking mutations (BM)) would inhibit re-cleavage of edited alleles. Surprisingly, the BMs had no significant impact on the maintenance of SNP alleles at the pig LDLR or GDF8 loci (FIG. 12 panel a). This suggested that either the conversion tract for oligo-templated HDR is quite short and does not incorporate the BM, or that altering the 5'-thymidine does not completely abolish TALEN activity.

ILLUMINA deep sequencing was conducted for 200-250 bp amplicons flanking the target sites from populations of cells transfected with oligos and TALEN mRNA. The results from five loci in pigs and cattle showed that insertion alleles were in general more prevalent and stable in the population (FIG. 13). Whereas BMs had little influence on the preservation of intended alleles in culture, there was a slight bias towards incorporation of BMs in SNP edited alleles versus insertional edits (FIG. 14). with our colony analysis, reads sorted on the basis of incorporating the intended SNP (iSNP), G938A or T1591C conversion in btGDF8 and p65, revealed that nearly half of reads with the iSNP had an additional mutation (iSNP+Mut) (FIG. 13 panel b), the majority of which were indels (FIG. 14). The majority of iSNP btGDF8 reads with indels in the spacer also contained one or both BM (data not shown) demonstrating that modification of the conserved 5'-thymidine was not able to suppress re-cleavage and subsequent indel generation. Thus, this base must be less critical to TALEN-binding than suggested by conservation, and provides a molecular basis for the inability of BMs to preserve alleles as described above.

Another strategy to reduce re-cutting of the SNP edits is to design TALENs such that their binding sites overlap the target SNPs. The influence of RVD/nucleotide mismatches within the TALEN-binding site for introgression of G938A SNP into cattle GDF8 was evaluated. Two pairs of TALENs were generated, one that bound the wildtype "G" allele (btGDF83.6-G) and another that bound the intended "A" allele (btGDF83.6-A) (FIG. 12 panel b). HDR with each TALEN pair was similar at day-3 whereas levels measured at day-12 were significantly higher using the TALENs that bound the wildtype "G" allele, indicating that recleavage was more prevalent with btGDF83.6-A which targets the repaired allele perfectly. Different RVD/nucleotide mismatches may have greater influence on maintenance of HDR alleles since the NN-RVD used for the wildtype "G" TALENs is able to bind both G and A nucleotides. For modification of porcine EIF4GI, it was found that three RVD/nucleotide mismatches were sufficient for protection of the HDR-edit as nearly 70% of isolated colonies contained an edited allele, greater than half of those being homozygotes (Table 1 and FIG. 15). Thus, the intentional alteration of the target locus to resist recleavage is an effective strategy for preserving edits.

It was hypothesized that gene-editing is a dynamic process. TALEN cleavage and re-cleavage are theorized to be in flux with repair by NHEJ, HDR with oligo template, and HDR with the sister chromatid as template. It was hypothesized that the observed loss of SNP alleles might be reduced by extending the hypothermic treatment, slowing cell proliferation long enough to outlast the burst of TALEN activity from TALEN mRNA transfection. Indeed, and surprisingly, this extension almost tripled the level of SNP HDR-edited alleles recovered after extended culture (FIG. 16).

For biomedical applications, alterations of bases besides the key bases that create the desired functionality is acceptable so long as the desired phenotype is achieved and the other changes are apparently without functional relevance. The inventors believe, however, that it is desirable for animals used in agriculture, to duplicate natural (native) alleles without further changes or to make only the intended edits without further changes. In contrast to the approaches where the mismatches are derived from successful introgression of the HDR construct, mismatches can be derived from changes in the RVD sequence. For TALENs, this process requires the TALEN monomers to be constructed with RVDs that do not bind to their corresponding nucleotides in the native alleles (FIG. 17 panel c). This concept of an intentional mismatch in the design of the nuclease (in this case TALENs) to prevent re-cutting of a desired is novel and operates under the following theory. TALENs can only tolerate some mismatches in their binding regions before their binding activity is essentially eliminated. Thus, it is possible to develop TALENs that have intentional mismatches with the native allele that will still cut, but as more mismatches are created, binding will be abolished. The theory of intentional mismatch is that after introgression of the desired allele, the new mismatch will have an additive effect to the engineered mismatches in the TALEN code to pass a critical tipping point to render the TALEN inactive. Counterintuitively, decreasing nuclease affinity for a target by intentional mismatching of RVDs provides a strategy to introgress a specific mutation down to a single nucleotide polymorphism (SNP), and reduce to undesired indels as a result of re-cutting.

As an example, a TALEN pair (caCLPG 1.1) was designed with zero mismatches to target the CLPG locus in the goat (Capra aegagrus hircus) genome (FIG. 17 panel a). The desired mutation was an adenine to guanine SNP, which has been linked to an increase in hindquarter muscle hypertrophy. The SNP allowed easy genotyping of colonies due to a loss of an Avail restriction site. Initial restriction digest assays showed several colonies with promising results, however when the alleles of each colony were sequenced, zero of fourteen were our intended product as each contained an undesired indel in addition to the desired SNP (FIG. 17 panel b and Table 2 labeled Success rate using intentional mismatches). To test the intentional mismatch approach, an additional three TALEN pairs were developed with different numbers and locations of intentional mismatches (FIG. 17 panel c). These TALENs were able to cut the wild-type allele at similar frequencies to the original caCLPG1.1 TALEN pair (FIG. 17 panel d). To observe the effect on HDR and reducing of undesired indels, individual colonies were derived from cells transfected with caCLPG 1.1c (two mismatches) and the HDR template. In contrast to the results with the original caCLPG1.1 TALENs, three of fifteen (20%) of Avail resistant colonies were positive for the desired SNP and contained no additional mutations (3/15 =20%) (FIG. 17 panel e and Table 2). Thus, derivation of the intended allele was dependent on intentional mismatch.

In a further example, the intention was to alter specifically two bases in the bovine DGAT gene. As with the CLPG locus, attempts to introgress the desired mutation without intentional mismatch failed as 0/12 RFLP colonies that were positive for the HindIn site were free of indels (FIG. 18 panel d and Table 2). The intentional mismatch method was used, and found overall rates of HDR on the population level (FIG. 18 panel c). Sequencing from individual colonies however revealed that two of three of the intentional mismatch designs were successful, giving rise to 2/12 and 3/12 correct alleles for 14.5 and 14.6 respectively (FIG. 18 panel e and Table 2). As with the CLPG locus, derivation of the intended allele was dependent on RVD-encoded intentional mismatch. The data in Table 1 demonstrated that combining mRNAs encoding TALENS plus oligonucleotides as templates for directing HDR achieved several benchmarks for a genome-editing strategy: 1) only target nucleotides were changed and mRNA transfection avoided unintended integration of plasmid DNA, 2) gene edits were efficient; from about 10% for SNPs to above 50% for some larger alterations, and 3) the method was reliable; targeted alteration of 16/16 sites (15 genes) was achieved. The efficiency and precision reported here is very surprising.

Two concerns in gene editing are stabilizing the changes at the targeted site and avoiding modification of unintended sites. With regard to the first, evidence was found that HDR-edits directing single basepair changes, i.e., SNPs, could be lost (FIG. 12 and FIG. 13 panel b). Based on the prediction that a thymidine preceding the targeted DNA sequence influences TAL binding, it was attempted to block re-cleavage of introgressed alleles by introducing BMs. However, it was found that BMs did not prevent TALEN activity and re-cleavage of edited alleles (FIG. 12 and FIGS. 14 and 15). In contrast, introduction of multiple SNPs or additional sequence (FIG. 8A and FIG. 15) resulted in more stable HDR226 edits. Surprisingly, it was found that extension of hypothermic culture resulted in the stabilization of introgressed SNP alleles. It is theorized that hypothermia slows cell proliferation primarily by prolonging G1-phase of the cell cycle so that this treatment differentially favors oligo-HDR versus sister chromatid templated repair in a cell-cycle dependent manner. Regardless of the mechanism, this approach offers a straight-forward strategy for recovering cells with precise introgression of SNP alleles.

A variety of objectives were achieved by precise gene editing (Table 1). Knockout of genes of biomedical relevance was accomplished by interrupting coding sequences with 4 bp indels. This strategy was reliable and generally resulted in HDR-edits in about 40% of the clones (range 2660%), and of those, up to one-third were homozygotes. At similar frequencies, a modified loxP(mloxP) site was integrated into ROSA26 and SRY loci in cattle and pigs that can be used as a landing pad (also referred to as a safe harbour) for insertion of novel sequences in livestock via recombinase-mediated cassette exchange. Previously, only NHEJ edits had been demonstrated for the Y chromosome of livestock, however, TALENs are suitable for direct stimulation of knockout/knock-in, at least as demonstrated in mice. Also, there was an introgression of native alleles between species/breeds, including the double-muscling mutations of GDF8 (SNP G938A23, 25 or 821de11123-25 from Piedmontese and Belgian Blue cattle respectively) into the genome of Wagyu cattle and Landrace pigs.

In some cases gene targeting with a standard plasmid vector and homologous recombination cassette will not be suitable for transgene delivery. Some cases could include when attempting to place a transgene in a site surrounded by repetitive elements or low complexity DNA. In these cases, the short homology required by oligo HDR may be preferred to integrate a transgene into a small region of unique sequence. However, the cargo capacity for oligo HDR is not sufficient to deliver a transgene. To circumvent this problem, we sought to combine the efficiency of oligo HDR for delivery of small insertions (e.g., LoxP sites) and the large cargo capacity of recombinase mediated cassette exchange (RMCE) for site specific integration of transgenes. Recombinase-mediated cassette exchange (RMCE) is a method based on the features of site-specific recombination processes (SSRs). This process allows for systematic, repeated modification of higher eukaryotic genomes by targeted integration. This result is achieved with RMCE by the clean exchange of a preexisting gene cassette for an analogous cassette carrying the gene of interest (GOI).

There is are problems with using RMCE to make genetically modified animals in the higher vertebrates, such as livestock. A significant problem is that due to the short lifespan of primary livestock cells prior to senescence, this process must occur in a single treatment. It would be possible in some other types of cells to perform the RMCE process serially wherein a cellular clone with the inserted LoxP site is isolated prior to transfection with the RCME machinery and isolation of clones to identify those with the correct targeting event. Applicants attempted to perform this process by simultaneously transfecting primary fibroblasts with four components: 1) SRY TALENs 2) an oligo with homology to SRY that includes two RMCE compatible loxP sites 3) a RMCE compatible transgene and 4) a source of Cre recombinase. In FIG. 19, the RMCE transgene was the puromycin resistance gene enabling selection for integration events. The number of puromycin resistant colonies was significantly increased when YFC-Cre was provided in contrast to the control group that included a mCherry expression cassette in place of YFC-Cre. Among puromycin resistant colonies (selected from cells treated for 3 days at either 30° C. or 37° C.) eight (n=95) and four percent (n=95) were positive for correct targeting of the RMCE vector. These results showed that it was possible to simultaneously provide the TALENS, HDR template containing loxP site, a transgene of interest flanked by loxP, and a Cre-recombinase mRNA resulting in RMCE mediated recombination into a TALEN targeted locus.

Embodiments of the invention include a process of homology dependent repair using an HDR template with a sequence that is introduced into the host cell or embryo that is a landing pad, e.g., for exogenous genes. The term landing pad is used according to its customary meaning to refer to a site-specific recognition sequence or a site-specific recombination site that is stably integrated into the genome of a host cell. Presence in the host genome of the heterologous site-specific recombination sequence allows a recombinase to mediate site-specific insertion of a heterologous polynucleotide or an exogenous into the host genome.

Embodiments include, kits, uses, compositions, and a method of creating a landing pad in a chromosomal DNA of a cell, comprising introducing a targeted nuclease system and a HDR template into the cell, with the targeted nuclease system comprising a DNA-binding member for specifically binding an endogenous cognate sequence in the chromosomal DNA, wherein the targeted nuclease system and the HDR template operate to alter the chromosomal DNA to have identity to the HDR template sequence, wherein the HDR template sequence comprises a landing pad. The method may be applied in a primary cell or embryo Embodiments include introducing the targeting nuclease, the HDR template encoding the landing pad, the exogenous gene that is compatible with the landing pad, and a source of recombinase compatible with the same; all of these may be introduced simultaneously. The term simultaneous is in contrast to a hypothetical process of treating cells multiple times in seriatim; the term must be kept in context, with an appreciation that it refers to a literally simultaneous introduction or an introduction calculated to having all of the factors bioactive at the same time. The landing site may be, e.g., RMCE compatible loxP sites, FRT, rox, VloxP, SloxP. The recombinase may be, e.g., Cre, FLP, Dre.

In other experiments, for improvement of animal welfare, the POLLED allele was transferred from a beef producing breed into cells from homed dairy cattle. A candidate SNP allele for African swine fever virus resilience (T1591C of p6539) was transferred from warthog to the genome of conventional swine cells and introgressed sheep SNPs responsible for elevated fecundity (FecB; BMPR-IB) and parent-of-origin dependent muscle hypertrophy (Callipyge) into the goat genome. Such introgression was previously impossible by breeding and will enable the assessment of defined genetic effects in related species. Non-meiotic allele introgression has not conventionally been possible without selective enrichment, and efficiencies reported herein are $10^3$-$10^4$ -fold higher than results previously obtained WITH selection. Such high levels of unselected single-allele introgression suggests it will be feasible to alter multiple alleles in a single generation of farm animals, decreasing the impact of long generation intervals on genetic improvement. Furthermore, efficient editing to homozygosity will greatly increase the rate of introgression per breeding interval.

As further elaboration of inventions described here customized endonucleases were used to generate live animals with precise edits at two independent loci. Pigs edited to disrupt the DAZL gene are useful as a model for studying the restoration of human fertility by germ cell transplantation, or for the production of genetically modified offspring by transfer of genetically modified germline stem cells as demonstrated in pigs, goats, and rodents. Gene edited alleles of APC provide a size-relevant model of colon cancer for pre-clinical evaluation of therapeutics, surgical intervention or detection modalities. These results demonstrate an introduction of genetic modifications, including polymorphisms, and including modifications that mimic natural polymorphisms into livestock. Gene-editing technology is useful to accelerate genetic improvement of agricultural products by intra- and interspecific allele introgression to help meet the growing global demand for animal protein. It also is useful for the development of large animals with defined genetics for drug and device testing, or for the development of therapeutic cells and organs. Other uses include making cells that can be used in vitro for research to understand the mechanisms of congenital and infectious disease, and to improve the methods for gene editing and control.

Gene Editing to Avoid Re-Binding by Nuclease Systems

Experimental results suggested that targeted (endo)nuclease systems were effectively cutting dsDNA at the intended cognate sites. Analysis of the data suggested that the nucleases would bind to sites that had already been templated and re-cleave the site, causing a reversion of the dsDNA to its original sequence. Targeted nuclease systems include a motif that binds to the cognate DNA, either by protein-to-DNA binding, or by nucleic acid-to-DNA binding. Experiments demonstrated that templates that contain polymorphisms can be selected to confound the re-binding or re-cutting by the targeted nuclease, thereby increasing significantly the number of precisely introgressed cellular clones.

Embodiments for reducing re-binding include a method of homology-directed repair (HDR) to introgress an exogenous allele into chromosomal DNA of a cell, comprising introducing a targeted nuclease system and a HDR template that comprises the exogenous allele into the cell, with the targeted nuclease system comprising a DNA-binding member for specifically binding an endogenous cognate sequence in the chromosomal DNA, wherein the targeted nuclease system and the HDR template operate to alter the chromosomal DNA to have identity to the HDR template sequence and to introgress the exogenous allele into the chromosomal DNA in place of an endogenous allele. In one embodiment the HDR template sequence is designed to introduce a polymorphism intended to reduce the specific binding of the DNA-binding member to genomic sequence once introgressed. Alternatively, the DNA-binding member of the targeted nuclease can be designed to recognize nucleotide sequences that aren't present in endogenous or exogenous sequence. Whereas the level of this hobbled DNA-binding member is sufficient to enable cleavage of the endogenous allele, the intended polymorphisms from the HDR template further alter the target site and decreases re-cleavage of precisely introgressed alleles. This results in a higher frequency of cellular clones within a population that contain those precise introgression events.

The term allele means one of two or more forms of a gene. A population or species of organisms typically includes multiple alleles at each locus among various individuals. Allelic variation at a locus is measurable as the number of alleles (polymorphisms) present, or the proportion of heterozygotes in the population. The term natural allele as used herein means an allele found in nature in the same species of organism that is being modified. The term novel allele means a non-natural allele. A human allele placed into a goat is a novel allele. The term synthetic allele means an allele that has not yet been found in nature. An exogenous allele is one that is introduced into an organism, and the endogenous allele is the one that is already in the cell, usually the one that is in the organism in its wild-type unmodified state. Animals that are heterozygous have two alleles. In some cases, it is desirable to introduce an exogenous allele to make an animal homozygous for an allele that is already present in the heterozygous animal. Movement of an allele interspecies means from one species of animal to another and intraspecies means movement between animals of the same species. The term exogenous allele is broad and includes DNA with, e.g., native, novel or synthetic SNPs or indels, reporters, endonuclease digestion sites, promoters, and vectors.

Homology directed repair (HDR) is a mechanism in cells to repair ssDNA and double stranded DNA (dsDNA) lesions. This repair mechanism can be used by the cell when there is an HDR template present that has a sequence with significant homology to the lesion site. Specific binding, as that term is commonly used in the biological arts, refers to a molecule that binds to a target with a relatively high affinity compared to non-target sequences, and generally involves a plurality of non-covalent interactions, such as electrostatic interactions, van der Waals interactions, hydrogen bonding, and the like. Specific binding involves processes of binding to a substrate and releasing from a substrate; as such it can be affected by changes in the efficiency of binding and release from a substrate as well as by a strength of the binding to the substrate. Accordingly, a reduction in specific binding may result from a lesser affinity to a substrate that reduces the number of binding events, or it may result from a reduced strength of binding to the substrate that reduces how long the binding is maintained. In the context of targeted endonucleases, without being bound to a particular theory, a change in specific binding of the endonuclease or guide sequence to the DNA can affect not only that actual binding but also be involved in an incompletely understood process of forming complexes with targeted and/or template DNA or RNA. Therefore specific binding can be measured relative to the actual DNA-binding events and is a useful feature for manipulating those processes, even if the actual events at the chromosomal level involve more or less than actual DNA-binding. Specific hybridization is a form of specific binding between nucleic acids that have complementary sequences. Proteins can also specifically bind to DNA, for instance, in TALENs or CRISPR/Cas9 systems or by Gal4 motifs. Introgression of an allele refers to a process of copying an exogenous allele over an endogenous allele with a template-guided process. The endogenous allele might actually be excised and replaced by an exogenous nucleic acid allele in some situations but present theory is that the process is a copying mechanism. Since alleles are gene pairs, there is significant homology between them. The allele might be a gene that encodes a protein, or it could have other functions such as encoding a bioactive RNA chain or providing a site for receiving a regulatory protein or RNA.

The HDR template is a nucleic acid that comprises the allele that is being introgressed. The template may be a dsDNA or a single-stranded DNA (ssDNA). ssDNA templates are preferably from about 20 to about 5000 residues although other lengths can be used. Artisans will immediately appreciate that all ranges and values within the explicitly stated range are contemplated; e.g., from 500 to 1500 residues, from 20 to 100 residues, and so forth. The template may further comprise flanking sequences that provide homology to DNA adjacent to the endogenous allele. The template may also comprise a sequence that is bound to a targeted nuclease system, and is thus the cognate binding site for the system's DNA-binding member. The term cognate refers to two biomolecules that typically interact, for example, a receptor and its ligand. In the context of HDR processes, one of the biomolecules may be designed with a sequence to bind with an intended, i.e., cognate, DNA site or protein site.

One embodiment for reducing specific binding to a targeted nuclease system comprises making changes in the HDR template relative to its alignment with the endogenous DNA. One type of change is designed to create mismatches between the cognate members. One change is an insertion or a deletion of one or more residues. Another change is a substitution of one residue for another residue that does not promote binding. The term residue refers to a unit in a molecular chain, e.g., an amino acid in a protein or a base in a nucleic acid. One place to make the change is at the cognate binding site for the system's DNA-binding member.

Another type of change is designed to interfere with operation of the nucleases by making the change is in the spacer in systems that operate with a spacer, e.g., TALENs pairs, the change may be made in the spacer area. These changes are may include a deletion, e.g., so that the nucleases are hindered from making cuts. These various changes are generally referred to as mismatches herein since they create mismatches when the sequences are aligned; in this context, a deletion, insertion, or substitution is a mismatch. Artisans routinely make alignments of sequences so that mismatches are readily identified with specificity. Pairs of nucleases require a spacing that provides a cooperativity; their activity can be disrupted by additions or subtractions to the spacer.

Further embodiments place a mismatch in the exogenous allele. The system's DNA-binding member is designed to bind at a site that at least partially overlaps with the endogenous allele. Once it is introgressed to have identity with the exogenous allele, the DNA-binding member has reduced binding. The DNA-binding member's cognate site thus changes from a preferred endogenous allele to a not-preferred exogenous allele. The cognate site may encompass all of the allele, or just a part of it. It is surprising that the introduction of a mismatch into the exogenous allele is required to stabilize the introgression of the exogenous allele. Apparently the problem of re-cleavage has a very large impact on stability of introgressed alleles. The data that shows this impact was not previously obtained by others because processes with a comparable efficiency were not conventionally available.

Embodiments include creating, with an HDR templating process, mismatches at these various places by insertion, deletion, or substitution of a residue. For instance, from 1-60 residues may be inserted, deleted, or substituted; artisans will immediately appreciate that all ranges and values within the explicitly stated range are contemplated; e.g., 1-3 residues, at least 10 residues, 4 residues, 4-20 residues, and so forth. One or more of these may be combined, e.g., an insertion at one place, a deletion at another, and a substitution at other places.

Embodiments include designing the DNA-binding member of the targeting endonuclease to place a mismatch in the DNA-binding member sequence as aligned with the endogenous chromosomal DNA. The mismatch would typically also be a mismatch for the exogenous DNA. These mismatches reduce targeted nuclease rebinding. Further mismatches may be used in combination with this method as already described, e.g., with the DNA-binding sites of the endonucleases chosen at positions wherein introgression of the exogenous allele; the HDR template having mismatches at the DNA-binding cognates; or in the spacer region to change the spacing.

These various embodiments can be performed in a reporter-free system and to make an SNP or an embodiment relating to an SNP. The cells or animals may be, e.g., vertebrate, livestock, primate, swine, cow, horse, sheep, goat, chicken, rabbit, fish, dog, mouse, cat, rat, and laboratory animal.

SNPs

These experimental results provide a process for placing single nucleotide polymorphisms (SNPs) into chromosomal DNA. The SNPs can be placed at a predetermined position. This control over placement is without precedent. For instance an SNP can be placed into an endogenous allele without other SNPs or modifications at other locations. Moreover, and crucially, an endogenous allele can be replaced with an exogenous allele that differs by only one SNP. And the replacements are made with minimal alterations to chromosomal DNA at any location in genome of the cell. One or more SNPs may be introgressed.

An embodiment is a method of creating a single nucleotide polymorphism (SNP) in a chromosomal DNA of a cell, comprising introducing a targeted nuclease system and a HDR template into the cell, with the targeted nuclease system comprising a DNA-binding member for specifically binding an endogenous cognate sequence in the chromosomal DNA, wherein the targeted nuclease system and the HDR template operate to alter the chromosomal DNA to have identity to the HDR template sequence, wherein the HDR template sequence comprises a SNP. The HDR template may have a plurality of SNPs or only one. Other changes may be present, e.g., insertions, deletions, or substitutions. Or the changes may be limited to a single SNP, or one or a plurality of SNPs introgressed into the endogenous allele. The HDR template sequence may comprise an exogenous allele that replaces an endogenous allele, with the exogenous allele comprising an SNP in a sequence alignment with the endogenous allele.

Further embodiments include placing an SNP into a cognate site for a DNA-binding member of a targeted nuclease system. The SNP may be chosen to reduce binding to the DNA-binding member. One SNP may be thusly placed, or a plurality. Further changes, SNPs, or others, may be present in the allele, or not. The chromosomal DNA may be free of all other changes.

Embodiments include a genetically modified animal, the animal belonging to a breed of animals having an endogenous allele, the animal comprising a genetic change at an SNP to change the chromosomal DNA of the animal from the endogenous allele to an exogenous allele found in another species or another breed of animal. The animal may comprise one or more of: a plurality of SNPs to change the chromosomal DNA of the animal from the endogenous allele to an exogenous allele found in another species or another breed of animal; further being free or reporters; being homozygous for the polymorphism, SNP or SNPs; being a livestock, primate, swine, cow, horse, sheep, goat, avian, chicken, rabbit, fish, dog, mouse, cat, rat, and laboratory animal.

These various embodiments can be performed in a reporter-free system and to make an SNP or an embodiment relating to an SNP. The cells or animals may be, e.g., livestock, primate, swine, cow, horse, sheep, goat, avian, chicken, rabbit, fish, dog, mouse, cat, rat, and laboratory animal.

Targeted Nuclease Systems

Genome editing tools such as transcription activator-like effector nucleases (TALENs) and zinc finger nucleases (ZFNs) have impacted the fields of biotechnology, gene therapy and functional genomic studies in many organisms. More recently, RNA-guided endonucleases (RGENs) are directed to their target sites by a complementary RNA molecule. The Cas9/CRISPR system is a RGEN. tracrRNA is another such tool. These are examples of targeted nuclease systems: these system have a DNA-binding member that localizes the nuclease to a target site. The site is then cut by the nuclease. TALENs and ZFNs have the nuclease fused to the DNA-binding member. Cas9/CRISPR are cognates that find each other on the target DNA. The DNA-binding member has a cognate sequence in the chromosomal DNA. The DNA-binding member is typically designed in light of the intended cognate sequence so as to obtain a nucleolytic action at nor near an intended site. Certain embodiments are applicable to all such systems without limitation; including, embodiments that minimize nuclease re-cleavage, embodiments for making SNPs with precision at an intended residue, and placement of the allele that is being introgressed at the DNA-binding site.

TALENs

The term TALEN, as used herein, is broad and includes a monomeric TALEN that can cleave double stranded DNA without assistance from another TALEN, e.g., as in Beurdeley, M. et al. Compact designer TALENs for efficient genome engineering. Nat. Commun. 4:1762 doi: 10.1038/ncomms2782 (2013). The term TALEN is also used to refer to one or both members of a pair of TALENs that are engineered to work together to cleave DNA at the same site. TALENs that work together may be referred to as a left-TALEN and a right-TALEN, which references the handedness of DNA or a TALEN-pair.

The cipher for TALs has been reported (PCT Publication WO 2011/072246) wherein each DNA binding repeat is responsible for recognizing one base pair in the target DNA sequence. The residues may be assembled to target a DNA sequence. In brief, a target site for binding of a TALEN is determined and a fusion molecule comprising a nuclease and a series of RVDs that recognize the target site is created. Upon binding, the nuclease cleaves the DNA so that cellular repair machinery can operate to make a genetic modification at the cut ends. The term TALEN means a protein comprising a Transcription Activator-like (TAL) effector binding domain and a nuclease domain and includes monomeric TALENs that are functional per se as well as others that require dimerization with another monomeric TALEN. The dimerization can result in a homodimeric TALEN when both monomeric TALEN are identical or can result in a heterodimeric TALEN when monomeric TALEN are different.

In some embodiments, a monomeric TALEN can be used. TALEN typically function as dimers across a bipartite recognition site with a spacer, such that two TAL effector domains are each fused to a catalytic domain of the FokI restriction enzyme, the DNA-recognition sites for each resulting TALEN are separated by a spacer sequence, and binding of each TALEN monomer to the recognition site allows FokI to dimerize and create a double-strand break within the spacer. Monomeric TALENs also can be constructed, however, such that single TAL effectors are fused to a nuclease that does not require dimerization to function. One such nuclease, for example, is a single-chain variant of FokI in which the two monomers are expressed as a single polypeptide. Other naturally occurring or engineered monomeric nucleases also can serve this role. The DNA recognition domain used for a monomeric TALEN can be derived from a naturally occurring TAL effector. Alternatively, the DNA recognition domain can be engineered to recognize a specific DNA target. Engineered single-chain TALENs may be easier to construct and deploy, as they require only one engineered DNA recognition domain. A dimeric DNA sequence-specific nuclease can be generated using two different DNA binding domains (e.g., one TAL effector binding domain and one binding domain from another type of molecule). TALENs may function as dimers across a bipartite recognition site with a spacer. This nuclease architecture also can be used for target-specific nucleases generated from, for example, one TALEN monomer and one zinc finger nuclease monomer. In such cases, the DNA recognition sites for the TALEN and zinc finger nuclease monomers can be separated by a spacer of appropriate length. Binding of the two monomers can allow FokI to dimerize and create a double-strand break within the spacer sequence. DNA binding domains other than zinc fingers, such as homeodomains, myb repeats or leucine zippers, also can be fused to FokI and serve as a partner with a TALEN monomer to create a functional nuclease.

The term nuclease includes exonucleases and endonucleases. The term endonuclease refers to any wild-type or variant enzyme capable of catalyzing the hydrolysis (cleavage) of bonds between nucleic acids within a DNA or RNA molecule, preferably a DNA molecule. Non-limiting examples of endonucleases include type II restriction endonucleases such as FokI, HhaI, HindIII NotI, BbvCI, EcoRI, BglII, and AlwI. Endonucleases comprise also rare-cutting endonucleases when having typically a polynucleotide recognition site of about 12-45 basepairs (bp) in length, more preferably of 14-45 bp. Rare-cutting endonucleases induce DNA double-strand breaks (DSBs) at a defined locus. Rare-cutting endonucleases can for example be a homing endonuclease, a chimeric Zinc-Finger nuclease (ZFN) resulting from the fusion of engineered zinc-finger domains with the catalytic domain of a restriction enzyme such as FokI or a chemical endonuclease. In chemical endonucleases, a chemical or peptidic cleaver is conjugated either to a polymer of nucleic acids or to another DNA recognizing a specific target sequence, thereby targeting the cleavage activity to a specific sequence. Chemical endonucleases also encompass synthetic nucleases like conjugates of orthophenanthroline, a DNA cleaving molecule, and triplex-forming oligonucleotides (TFOs), known to bind specific DNA sequences. Such chemical endonucleases are comprised in the term "endonuclease" according to the present invention. Examples of such endonuclease include I-See I, I-Chu L I-Cre I, I-Csm I, PI-See L PI-Tti L PI-Mtu I, I-Ceu I, I-See IL 1-See III, HO, PI-Civ I, PI-Ctr L PI-Aae I, PI-Bsu I, PI-Dha I, PI-Dra L PI-May L PI-Meh I, PI-Mfu L PI-Ml I, PI-Mga L PI-Mgo I, PI-Min L PI-Mka L PI-Mle I, PI-Mina I, PI-30 Msh L PI-Msm I, PI-Mth I, PI-Mtu I, PI-Mxe PI-Npu I, PI-Pfu L PI-Rma I, PI-Spb I, PI-Ssp L PI-Fae L PI-Mja I, PI-Pho L PI-Tag L PI-Thy I, PI-Tko I, PI-Tsp I, I-Msol.

Extended Hypothermia for Template-Directed Repair

Experiments surprisingly showed that an extended period of hypothermic culture could enhance the efficiency of templating processes. Hypothermic cell cultures are known to be useful for up to about three days to introduce double-stranded DNA breaks. Conventional theories for this effect revolve around the idea that the active enzymes are being diluted or the DNA is stabilized by inhibiting division.

The data herein, however, are not consistent with these other theories. Instead, it is believed that hypothermia minimizes re-repair of altered chromosomes as guided by the sister chromatid. In other words, even if there is successful integration, the cell may use the sister chromatid at the altered site to undo the changed allele. Moreover, these data are the first to show that hypothermia could be used to impact templating processes. A surprising aspect of the experiments was that the extended hypothermic culture did not improve the efficiency of copying the template into the cellular DNA. What it improved was the stability of the exogenous allele after it had been copied. In fact, this process almost tripled the level of SNP HDR-edited alleles. The theories of operation for this phenomenon are discussed, above.

An embodiment is a hypothermic method of template-directed repair to change a chromosomal DNA of a cell, comprising introducing into a living cell a targeted nuclease system and a nucleic acid template, wherein the targeted nuclease system and the template operate to alter the chromosomal DNA to have identity to the template sequence wherein the living cell is maintained at a hypothermic culturing temperature below a physiological temperature for a time period. The length of the culture can be varied as appropriate, e.g., more than 3 days to 31 days or 72 to 800 hours; artisans will immediately appreciate that all ranges and values within the explicitly stated range are contemplated; e.g., 80 to 600 hours, 4 days to 15 days, 3.1 days to two weeks, and so forth. Extended culture times at about 20° C. have been successful (data not shown). The hypothermic culture temperature ranges from 20 to 34° C.; artisans will immediately appreciate that all ranges and values within the explicitly stated range are contemplated; e.g., 21 to 30° C. Moreover embodiments include maintaining the culture at a specific temperature within the range as well as allowing the culture temperature to change while remaining within the range. The term "kept within a range" in this context includes both these embodiments Embodiments include culturing to provide a stability of an allele introduced into a cell; for example, with the stability being for more than 5 cell divisions, or at least 3 cell divisions, or a value between 3 and 10 cell divisions; artisans will immediately appreciate that all ranges and values within the explicitly stated range are contemplated.

Production of Biomedical Model Animals with Gene-Edited Alleles

Two gene-edited loci in the porcine genome were selected to carry through to live animals—APC and DAZL. Mutations in the adenomatous polyposis coli (APC) gene are not only responsible for familial adenomatous polyposis (FAP), but also play a rate-limiting role in a majority of sporadic colorectal cancers. Dazl (deleted in azoospermia-like) is an RNA binding protein that is important for germ cell differentiation in vertebrates. The DAZL gene is connected to fertility, and is useful for infertility models as well as spermatogenesis arrest. Colonies with HDR-edited alleles of DAZL or APC for were pooled for cloning by chromatin transfer. Each pool yielded two pregnancies from three transfers, of which one pregnancy each was carried to term. A total of eight piglets were born from DAZL modified cells, each of which reflected genotypes of the chosen colonies consistent with either the HDR allele or deletions resulting from NHEJ. Three of the DAZL piglets were stillborn. Of the six piglets from APC modified cells, one was stillborn, three died within one week, and another died after 3 weeks, all for unknown reasons likely related to cloning. All six APC piglets were heterozygous for the intended HDR-edited allele and all but one either had an in-frame insertion or deletion of 3 bp on the second allele. Remaining animals are being raised for phenotypic analyses of spermatogenesis arrest (DAZL−/−founders) or development of colon cancer (APC+/−founders).

Template-driven introgression methods are detailed herein Embodiments of the invention include template-driven introgression, e.g., by HDR templates, to place an APC or a DAZL allele into a non-human animal, or a cell of any species.

This method, and methods generally herein, refer to cells and animals. These may be chosen from the group consisting of vertebrate, livestock, an artiodactyl, a primate, cattle, a swine, a sheep, a goat, a bird, a chicken, a rabbit, fish, dog, mice, rat, cat or laboratory animal. The term livestock means domesticated animals that are raised as commodities for food or biological material. The term artiodactyl means a hoofed mammal of the order Artiodactyla, which includes cattle, deer, camels, hippopotamuses, sheep, pigs and goats that have an even number of toes, usually two or sometimes four, on each foot.

Recombinases

Embodiments of the invention include administration of a targeted nuclease system with a recombinase (e.g., a RecA protein, a Rad51) or other DNA-binding protein associated with DNA recombination. A recombinase forms a filament with a nucleic acid fragment and, in effect, searches cellular DNA to find a DNA sequence substantially homologous to the sequence. For instance a recombinase may be combined with a nucleic acid sequence that serves as a template for HDR. The recombinase is then combined with the HDR template to form a filament and placed into the cell. The recombinase and/or HDR template that combines with the recombinase may be placed in the cell or embryo as a protein, an mRNA, or with a vector that encodes the recombinase. The disclosure of US Pub 2011/0059160 (U.S. Ser. No. 12/869,232) is hereby incorporated herein by reference for all purposes; in case of conflict, the specification is controlling. The term recombinase refers to a genetic recombination enzyme that enzymatically catalyzes, in a cell, the joining of relatively short pieces of DNA between two relatively longer DNA strands. Recombinases include Cre recombinase, Hin recombinase, RecA, RAD51, Cre, and FLP. Cre recombinase is a Type I topoisomerase from P1 bacteriophage that catalyzes site-specific recombination of DNA between loxP sites. Hin recombinase is a 21 kD protein composed of 198 amino acids that is found in the bacteria Salmonella. Hin belongs to the serine recombinase family of DNA invertases in which it relies on the active site serine to initiate DNA cleavage and recombination. RAD51 is a human gene. The protein encoded by this gene is a member of the RAD51 protein family which assist in repair of DNA double strand breaks. RAD51 family members are homologous to the bacterial RecA and yeast Rad51. genes. Cre recombinase is an enzyme that is used in experiments to delete specific sequences that are flanked by loxP sites. FLP refers to Flippase recombination enzyme (FLP or Flp) derived from the 2μ plasmid of the baker's yeast *Saccharomyces cerevisiae*.

Herein, "RecA" or "RecA protein" refers to a family of RecA-like recombination proteins having essentially all or most of the same functions, particularly: (i) the ability to position properly oligonucleotides or polynucleotides on their homologous targets for subsequent extension by DNA polymerases; (ii) the ability topologically to prepare duplex nucleic acid for DNA synthesis; and, (iii) the ability of RecA/oligonucleotide or RecA/polynucleotide complexes efficiently to find and bind to complementary sequences. The best characterized RecA protein is from *E. coli*; in addition to the original allelic form of the protein a number of mutant RecA-like proteins have been identified, for example, RecA803. Further, many organisms have RecA-like strand-transfer proteins including, for example, yeast, *Drosophila*, mammals including humans, and plants. These proteins include, for example, Rec1, Rec2, Rad51, Rad51B, Rad51C, Rad51D, Rad51E, XRCC2 and DMC1. An embodiment of the recombination protein is the RecA protein of *E. coli*. Alternatively, the RecA protein can be the mutant RecA-803 protein of *E. coli*, a RecA protein from another bacterial source or a homologous recombination protein from another organism.

Alleles for Introgression

Allele introgression has many important applications. The Allelic Introgression Table, below, and Table 1 (Frequencies for recovery of colonies with HDR alelles) describe certain genes and their applications. Artisans reading this application will be able to make and use the introgressions and resultant cells and animals. Artisans can readily apply the processes set forth herein for the use of these alleles as templates or targets for disruption. Embodiments include making a genetically modified cell or animal (for instance, a lab animal, an F0 founder, or animal line) whose genome has received a gene from Table 1 or the Allelic introgression Table, e.g., by insertion or template-driven allele introgression that replaces the endogenous allele with an allele from Table 1 or the Allelic introgression Table. Alleles for some genes are reported to provide livestock production advantages, but are at very low frequencies or are absent in some breeds or species (see items 1-9). Introgression of these alleles can be of significant value for production traits. For example, the Polled allele (item 1) from beef breeds results in animals that do not have horns, whereas dairy breeds do not have this allele so have horns and need to be dehorned as a production practice. Allele introgression from beef breeds into horned (dairy) breeds will lead to hornless dairy cattle which is has value for both production and animal welfare. Other examples relate to alleles that can increase or enhance characteristics of agricultural products such as meat (items 4-6) and milk (items 7-8). Item 9 is useful for disease resistance.

Many commercial and commonly used animal breeds have been carefully bred to establish desirable traits but, in the process of that breeding, have accumulated genetic errors that reduce their reproductive success because of losses in fertility or by increasing miscarriages. Deleterious alleles for some genes are present in animal populations. As explained elsewhere herein, the inventive techniques provide for changing alleles only at an intended location in a target animal, without other modifications resulting from genetic tools or from meiotic recombinations. Therefore, for the first time, it is possible to clean-up the genetic errors that have accumulated in livestock and animal breeds without disrupting the genome of the animals and, consequently, disrupting traits or causing unintended consequences. Alleles for some genes can be used to control animal fertility for genetic control of breeding stock (items 2-3). The term breed is a term of art that refers to domestic animals that, through selection and breeding, have come to resemble one another and pass those traits uniformly to their offspring.

Many useful animal models can be made. Certain alleles are useful, see Allelic introgression Table items 10-39. Some of these are established in animals. Others of the genes are known to cause human disease, so introgressing these alleles into livestock, lab animals, or other animals is useful to create biomedical models of human disease.

Embodiments of the invention include a method of making a genetically modified animal, said method comprising exposing embryos or cells to an mRNA encoding a TALEN, with the TALEN specifically binding to a target chromosomal site in the embryos or cells, cloning the cells in a surrogate mother or implanting the embryos in a surrogate mother, with the surrogate mother thereby gestating an animal that is genetically modified without a reporter gene and only at the TALEN targeted chromosomal site wherein the allele is a member of the group consisting of (a) horn polled locus (b) a gene recessive for fertility defects, e.g., CWC15 and/or ApaF1 (c) genes for enhancing a livestock trait, e.g., meat production (GDF8, IGF2, SOCS2, or a combination thereof) and/or milk production (DGAT1 and/or or ABCG2) (d) a gene for resistance to African swine fever (P65/RELA) (e) a gene for changing animal size (PLAG1, GHRHR) (f) genes that potential tumor growth (e.g., TP53, APC, PTEN, RB1, Smad4, BUB1B, BRCA1, BRCA2, ST14 or a combination thereof) (g) human oncogenes for animal models of cancer (e.g., AKT1, EGF, EGFR, KRAS, PDGFRA/B or a combination thereof) (h) genes in animal models for hypercholesterolemia (to induce atherosclerosis, stroke, and Alzheimer's disease models), e.g., LDLR, ApoE, ApoB or a combination thereof (i) Inflammatory Bowel disease, e.g., NOD2 (j) spina bifida, e.g., VANGL1 and/or VANGL2 (k) pulmonary hypertension, e.g., miR-145 (l) genes for cardiac defects, e.g., BMP10, SOS1, PTPN11, Nrg1, Kir6.2, GATA4, Hand2, or a combination thereof and (l) celiac disease genes, e.g., HLA-DQA1.

| Allelic introgression Table | |
|---|---|
| Item | Genes; Species [Gene Reference Identification] | Application |
|---|---|---|
| 1 | Horn-Polled Locus; Bovine [UMD3.1:1:1705490:1706389:1] | Transfer allele into cows of various breeds to make bovine lines of those species without horns; see Medugorac, I., D. Seichter, et al., (2012). "Bovine polledness - an autosomal dominant trait with allelic heterogeneity." PloS one, 7(6): e39477. |
| 2 | CWC15 (JH1) [hs Gene ID: 51503] | Use natural allele as template to restore wildtype sequence to animal lines and breeds with defective alleles; see VanRaden, P. M., K. M. Olson, et al., (2011). "Harmful recessive effects on fertility detected by absence of homozygous haplotypes." J Dairy Sci., 94(12): 6153-6161. |
| 3 | ApaF1 (HH1) [hs Gene ID: 317] | |
| 4 | GDF8 [hs Gene ID: 2660] | Enhancement of growth for meat production. |
| 5 | IGF2 [hs Gene ID: 3481] | |
| 6 | SOCS2 [hs Gene ID: 8835] | |
| 7 | DGAT1 [hs Gene ID: 8694] | Alleles of these genes are known to influence the amount and composition of milk |
| 8 | ABCG2 Hs Gene ID: 9429] | |
| 9 | P65/RELA [hs Gene ID: 5970] | Transfer of the warthog p65 allele to commercial swine breeds for resistance to African swine fever. Palgrave, C. J., L. Gilmour, et al., (2011). "Species-specific variation in RELA underlies differences in NF-kappaB activity: a potential role in African swine fever pathogenesis." Journal of virology, 85(12): 6008-6014. |
| 10 | GHRHR [hs Gene ID: 2692] | Size reduction of animals for Biomedical modeling. |
| 11 | TP53 [hs Gene ID: 7157] | Tumor suppressor genes; heterozygous knockout to potentiate tumor growth. |
| 12 | APC [hs Gene ID: 324] | |
| 13 | PTEN [hs Gene ID: 5728] | |
| 14 | RB1 [hs Gene ID: 5925] | |
| 15 | Smad4 [hs Gene Id: 4089] | |
| 16 | BUB1B [hs Gene ID: 701] | |
| 17 | BRCA1 [hs Gene ID: 672] | |
| 18 | BRCA2 [hs Gene ID: 675] | |
| 19 | ST14 [hs Gene ID: 6768] | |
| 20 | AKT1 [hs Gene ID: 207] | Oncogenes. Activated human alleles will be introgressed into pigs to model cancers. |
| 21 | EGF [hs Gene ID: 1950] | |
| 22 | EGFR [hs Gene ID: 1956] | |
| 23 | KRAS [hs Gene ID: 3845] | |
| 24 | PDGFRA/B [hs Gene IDs: 5156/5159] | |
| 25 | LDLR [hs Gene ID: 3949] | Hypercholesterolemia to induce atherosclerosis, stroke and Alzheimer's disease models. |
| 26 | ApoE [hs Gene ID: 348] | |
| 27 | ApoB [hs Gene ID: 338] | |
| 28 | NOD2 [hs Gene ID: 64127] | Inflammatory Bowel disease for animal models. |
| 29 | VANGL1 [hs Gene ID: 81839] | Spina Bifida is associated with alleles of these genes. Transfer of these alleles in livestock will generate models for biomedical research. |
| 30 | VANGL2 [hs Gene ID: 57216] | |
| 31 | miR-145 [hs Gene ID: 611795] | Pulmonary hypertension is associated with alleles of these genes. Transfer of these alleles in swine will generate models for biomedical research. |

-continued

Allelic introgression Table

| Item | Genes; Species [Gene Reference Identification] | Application |
|---|---|---|
| 32 | BMP10 [hs Gene ID: 27302] | Cardiac defects associated with alleles of these genes. Transfer of these alleles will generate models for biomedical research. |
| 33 | SOS1 [hs Gene ID: 6654] | |
| 34 | PTPN11 [hs Gene ID: 5781] | |
| 35 | Nrg1 [hs Gene ID: 3084] | |
| 36 | Kir6.2 [hs Gene ID: 3767] | |
| 37 | GATA4 [hs Gene ID: 2626] | |
| 38 | Hand2 [hs Gene ID: 9464] | |
| 39 | HLA-DQA1 [hs Gene ID: 3117] | Alleles associated with celiac disease will be transferred to livestock to create an animal model. |

Animals Genetically Modified Without Any Reporters; Certain TALENs Techniques; Allelic Introgressions Certain embodiments of the invention are directed to processes of modifying cells or embryos without the use of reporters and/or selection markers. In general, it was observed that TALENs and CRISPR/Cas9 modifications were unstable over a time frame of several days. Accordingly, processes described herein for stabilizing changes may be used, as well as other processes described in US 2013/0117870: for instance, direct mRNA introduction and/or use of ssDNA templates. The term direct introduction, e.g., direct mRNA introduction, refers to introduction of mRNA material. In contrast, introduction by means of a vector encoding the mRNA is termed indirect introduction. Many processes of direct introduction are known, e.g., electroporation, transfection, lipofection, liposome, nucleofection, biolistic particles, nanoparticles, lipid transfection, electrofusion, and direct injection.

Founder animals can be immediately created from modified cells or embryos without the need to create initially modified animals that are subsequently bred to create the basis for a new transgenic line. The term founder or founder animal is used to refer to a first-generation ("F0") transgenic animal that develops directly from the cloned cell or treated/injected embryo that is modified. Methods reported herein provide for creation of founders genetically modified only at the chromosomal target site, and without intermediate steps of breeding and/or inbreeding. Moreover, embodiments include founders that are homozygous for the modification. The founders may be prepared without ever exposing cells and/or embryos to reporter genes (and/or selection marker genes).

A method of making a genetically modified animal comprises introducing TALENs and/or vectors into cultured cells, e.g., primary livestock cells. The TALENs are directed to specific chromosomal sites and cause a genetic alteration at the site. An HDR template may also be introduced into the cell, e.g., as a double stranded vector, single stranded DNA, or directly as an ss nucleotide. The cultured cells are subsequently cultured to form colonies of clonal cells. The colonies are tested by PCR and/or sequenced, or otherwise assayed for a genetic modification, preferably without a reporter gene and/or without a selection marker. Cells are taken from colonies that are genetically modified at the intended site and used in cloning. For example, from 10 to 50,000 cells are used to make from 10 to 50,000 embryos that are implanted into surrogates, e.g., in sets of 1-500 embryos per surrogate; artisans will immediately appreciate that all the ranges and values within the explicitly stated ranges are contemplated. Embodiments comprise exposing the cells to the TALEN without a reporter gene, creating colonies of clonal cells, and testing a subset of members of the colonies to identify colonies incorporating the modification at the chromosomal target site.

Genetically Modified Animals

Various techniques known in the art can be used to introduce nucleic acid constructs into non-human animals to produce founder animals, in which the nucleic acid construct is integrated into the genome. Such techniques include, without limitation, pronuclear microinjection (U.S. Pat. No. 4,873,191), retrovirus mediated gene transfer into germ, gene targeting into embryonic stem cells, electroporation of embryos, sperm-mediated gene transfer (Lavitrano et al., (2002) *Proc. Natl. Acad. Sci. USA,* 99:14230-14235; Lavitrano et al., (2006) *Reprod. Fert. Develop.,* 18:19-23), and in vitro transformation of somatic cells, such as cumulus or mammary cells, or adult, fetal, or embryonic stem cells, followed by nuclear transplantation. Pronuclear microinjection, sperm mediated gene transfer, and somatic cell nuclear transfer are particularly useful techniques, as well as cytoplasmic injection, primordial germ cell transplantation, and blastocyst chimera production whereby a germ cell is propagated in an embryo.

Typically, in pronuclear microinjection, a nucleic acid construct is introduced into a fertilized egg; 1 or 2 cell fertilized eggs are used as the pronuclei containing the genetic material from the sperm head and the egg are visible within the protoplasm. Pronuclear staged fertilized eggs can be obtained in vitro or in vivo (i.e., surgically recovered from the oviduct of donor animals) and In vitro fertilized eggs can be produced. For example, in swine, mature oocytes can be fertilized in 500 μl Minitube PORCPRO IVF MEDIUM SYSTEM (Minitube, Verona, Wis.) in Minitube 5-well fertilization dishes. In preparation for in vitro fertilization (IVF), freshly-collected or frozen boar semen can be washed and resuspended in PORCPRO IVF Medium to 4×10⁵ sperm. Sperm concentrations can be analyzed by computer assisted semen analysis (SPERMVISION, Minitube, Verona, Wis.). Final in vitro insemination can be performed in a 10 µl volume at a final concentration of approximately 40 motile sperm/oocyte, depending on boar. Incubate all fertilizing oocytes at 38.7° C. in 5.0% $CO_2$ atmosphere for 6 hours. Six hours post-insemination, presumptive zygotes can be washed twice in NCSU-23 and moved to 0.5 mL of the same medium. This system can produce 20-30% blastocysts routinely across most boars with a 10-30% polyspermic insemination rate.

In somatic cell nuclear transfer, a genetically modified cell or blastomere, e.g., an embryonic blastomere, fetal fibroblast, adult ear fibroblast, or granulosa cell, can be introduced into an enucleated oocyte to establish a combined cell. In some conventions, oocytes arrested at meiosis-2 are termed "eggs". After producing an embryo (e.g., by fusing and activating the oocyte), the embryo is transferred to the oviducts of a recipient female, about 20 to 24 hours after activation. Standard breeding techniques can be used to create animals that are homozygous for the target nucleic acid from initial heterozygous founder animals.

Vectors and Nucleic Acids

A variety of nucleic acids may be introduced into cells. As used herein, the term nucleic acid includes DNA, RNA, and nucleic acid analogs, and nucleic acids that are double-stranded or single-stranded (i.e., a sense or an antisense single strand). Nucleic acid analogs can be modified at the base moiety, sugar moiety, or phosphate backbone to improve, for example, stability, hybridization, or solubility of the nucleic acid. The deoxyribose phosphate backbone can be modified to produce morpholino nucleic acids. In addition, the deoxyphosphate backbone can be replaced with, for example, a phosphorothioate or phosphorodithioate backbone, a phosphoroamidite, or an alkyl phosphotriester backbone. A nucleic acid sequence can be operably linked to a regulatory region such as a promoter for expression. As used herein, operably linked refers to positioning of a regulatory region relative to a nucleic acid sequence in such a way as to permit or facilitate transcription of the target nucleic acid. Any type of promoter can be operably linked to a target nucleic acid sequence. Examples of promoters include, without limitation, tissue-specific promoters, constitutive promoters, and promoters responsive or unresponsive to a particular stimulus.

Nucleic acid constructs can be methylated using an SssI CpG methylase (New England Biolabs, Ipswich, Mass.). In general, the nucleic acid construct can be incubated with S-adenosylmethionine and SssI CpG-methylase in buffer at 37° C. Hypermethylation can be confirmed by incubating the construct with one unit of HinPlI endonuclease for 1 hour at 37° C. and assaying by agarose gel electrophoresis.

Nucleic acid constructs can be introduced into embryonic, fetal, or adult artiodactyl cells of any type, including, for example, germ cells such as an oocyte or an egg, a progenitor cell, an adult or embryonic stem cell, a primordial germ cell, a kidney cell such as a PK-15 cell, an islet cell, a beta cell, a liver cell, or a fibroblast such as a dermal fibroblast, using a variety of techniques. Non-limiting examples of techniques include the use of transposon systems, recombinant viruses that can infect cells, or liposomes or other non-viral methods such as electroporation, microinjection, or calcium phosphate precipitation, that are capable of delivering nucleic acids to cells. In transposon systems, the transcriptional unit of a nucleic acid construct, i.e., the regulatory region operably linked to a target nucleic acid sequence, is flanked by an inverted repeat of a transposon. Several transposon systems, including, for example, Sleeping Beauty (see, U.S. Pat. No. 6,613,752 and U.S. Publication No. 2005/0003542); Frog Prince (Miskey et al., (2003) *Nucleic Acids Res.*, 31:6873); Tol2 (Kawakami (2007) *Genome Biology*, 8 (Suppl. 1):57; Minos (Pavlopoulos et al., (2007) *Genome Biology*, 8 (Suppl. 1): S2); *Hsmar* 1 (Miskey et al., (2007)) *Mol. Cell Biol.*, 27:4589); and Passport have been developed to introduce nucleic acids into cells, including mice, human, and pig cells. The Sleeping Beauty and Passport transposon is particularly useful. A transposase can be delivered as a protein, encoded on the same nucleic acid construct as the target nucleic acid, can be introduced on a separate nucleic acid construct, or provided as an mRNA (e.g., an in vitro-transcribed and capped mRNA).

Nucleic acids can be incorporated into vectors. A vector is a broad term that includes any specific DNA segment that is designed to move from a carrier into a target DNA. A vector may be referred to as an expression vector, or a vector system, which is a set of components needed to bring about DNA insertion into a genome or other targeted DNA sequence such as an episome, plasmid, or even virus/phage DNA segment. Vector systems such as viral vectors (e.g., retroviruses, adeno-associated virus and integrating phage viruses), and non-viral vectors (e.g., transposons) used for gene delivery in animals have two basic components: 1) a vector comprised of DNA (or RNA that is reverse transcribed into a cDNA) and 2) a transposase, recombinase, or other integrase enzyme that recognizes both the vector and a DNA target sequence and inserts the vector into the target DNA sequence. Vectors most often contain one or more expression cassettes that comprise one or more expression control sequences, wherein an expression control sequence is a DNA sequence that controls and regulates the transcription and/or translation of another DNA sequence or mRNA, respectively.

Many different types of vectors are known. For example, plasmids and viral vectors, e.g., retroviral vectors, are known. Mammalian expression plasmids typically have an origin of replication, a suitable promoter and optional enhancer, and also any necessary ribosome binding sites, a polyadenylation site, splice donor and acceptor sites, transcriptional termination sequences, and 5' flanking non-transcribed sequences. Examples of vectors include: plasmids (which may also be a carrier of another type of vector), adenovirus, adeno-associated virus (AAV), lentivirus (e.g., HIV-1, SIV or FIV), retrovirus (e.g., ASV, ALV or MoMLV), and transposons (e.g., Sleeping Beauty, P-elements, Tol-2, Frog Prince, piggyBac).

As used herein, the term nucleic acid refers to both RNA and DNA, including, for example, cDNA, genomic DNA, synthetic (e.g., chemically synthesized) DNA, as well as naturally occurring and chemically modified nucleic acids, e.g., synthetic bases or alternative backbones. A nucleic acid molecule can be double-stranded or single-stranded (i.e., a sense or an antisense single strand). The term transgenic is used broadly herein and refers to a genetically modified organism or genetically engineered organism whose genetic material has been altered using genetic engineering techniques. A knockout artiodactyl is thus transgenic regardless of whether or not exogenous genes or nucleic acids are expressed in the animal or its progeny.

The nucleic acid sequences set forth herein are intended to represent both DNA and RNA sequences, according to the conventional practice of allowing the abbreviation "T" stand for "T" or for "U", as the case may be, for DNA or RNA.

Polynucleotides are nucleic acid molecules of at least three nucleotide subunits. Polynucleotide analogues or polynucleic acids are chemically modified polynucleotides or polynucleic acids. In some embodiments, polynucleotide analogues can be generated by replacing portions of the sugar-phosphate backbone of a polynucleotide with alternative functional groups. Morpholino-modified polynucleotides, referred to herein as "morpholinos," are polynucleotide analogues in which the bases are linked by a morpholino-phosphorodiamidate backbone (see, e.g., U.S. Pat. Nos. 5,142,047 and 5,185,444). In addition to morpholinos, other examples of polynucleotide analogues include analogues in which the bases are linked by a polyvinyl backbone, peptide nucleic acids (PNAs) in which the bases are linked by amide bonds formed by pseudopeptide 2-aminoethyl-glycine groups, analogues in which the nucleoside subunits are linked by methylphosphonate groups, analogues in which the phosphate residues linking nucleoside subunits are replaced by phosphoroamidate groups, and phosphorothioated DNAs, analogues containing sugar moieties that have 2' O-methyl group). Polynucleotides of the invention can be produced through the well-known and routinely used technique of solid phase synthesis. Alternatively, other suitable methods for such synthesis can be used (e.g., common molecular cloning and chemical nucleic acid synthesis techniques). Similar techniques also can be used to prepare polynucleotide analogues such as morpholinos or phosphorothioate derivatives. In addition, polynucleotides and polynucleotide analogues can be obtained commercially. For oligonucleotides, examples of pharmaceutically acceptable compositions are salts that include, e.g., (a) salts formed with cations such as sodium, potassium, ammonium, etc.; (b) acid addition salts formed with inorganic acids, for example, hydrochloric acid, hydrobromic acid (c) salts formed with organic acids e.g., for example, acetic acid, oxalic acid, tartaric acid; and (d) salts formed from elemental anions e.g., chlorine, bromine, and iodine.

A sequence alignment is a way of arranging the sequences of DNA, RNA, or protein to identify regions of similarity. Aligned sequences of nucleotide or amino acid residues are typically represented as rows within a matrix, with gaps are inserted between the residues so that identical or similar characters are aligned in successive columns.

EXAMPLES

Example 1

TALEN Designing and Production

Candidate TALEN target DNA sequences and RVD sequences were identified using the online tool "TAL EFFECTOR NUCLEOTIDE TARGETER". Plasmids for TALEN DNA transfection or in vitro TALEN mRNA transcription were then constructed by following the Golden Gate Assembly protocol using pCGOLDYTALEN (Addgene ID 38143) and RCIscript-GOLDYTALEN (Addgene ID 38143) as final destination vectors (Carlson 2012). The final pC-GoldyTALEN vectors were prepared by using PureLink® HIPURE PLASMID MIDIPREP Kit (Life Technologies) and sequenced before usage. Assembled RCIscript vectors prepared using the QIAPREP SPIN MINIPREP kit (Qiagen) were linearized by SacI to be used as templates for in vitro TALEN mRNA transcription using the mMESSAGE mMACHINE® T3 Kit (Ambion) as indicated previously elsewhere. Modified mRNA was synthesized from RCIScript-GOLDYTALEN vectors as previously described (Carlson 2012) substituting a ribonucleotide cocktail consisting of 3'-0-Mem7G(5')ppp(5')G RNA cap analog (New England Biolabs), 5-methylcytidine triphosphate pseudouridine triphosphate (TriLink Biotechnologies, San Diego, Calif.) and adenosine triphosphate guanosine triphosphate. Final nucleotide reaction concentrations are 6 mM for the cap analog, 1.5 mM for guanosine triphosphate, and 7.5 mM for the other nucleotides. Resulting mRNA was DNAse treated prior to purification using the MEGACLEAR REACTION CLEANUP kit (Applied Biosciences).

Example 2

CRISPR/Cas9 Design and Production

Gene specific gRNA sequences were cloned into the Church lab gRNA vector (Addgene ID: 41824) according their methods. The Cas9 nuclease was provided either by co-transfection of the hCas9 plasmid (Addgene ID: 41815) or mRNA synthesized from RCIScript-hCas9. This RCIScript-hCas9 was constructed by sub-cloning the XbaI-AgeI fragment from the hCas9 plasmid (encompassing the hCas9 cDNA) into the RCIScript plasmid. Synthesis of mRNA was conducted as above except that linearization was performed using KpnI.

Example 3

Donor Repair Template Preparation

BB-HDR (1,623 bp) plasmid. A 1,695 bp fragment encompassing the Belgian Blue allele was PCR amplified (btGDF8 BB 5-1: 5'-CAAAGTTGGTGACGTGACAGAGGTC (SEQ ID NO:88); btGDF8 BB 3-1: 5'-GTGTGCCATCCC-TACTTTGTGGAA(SEQ ID NO:89)) from Belgian Blue genomic DNA and TOPO cloned into the PCR 2.1 vector (Life Technologies). This plasmid was used as positive control template for analytical primer sets and for derivation of the 1,623 bp BB-HDR template by PCR with following primers (BB del HR 1623 5-1: 5'-GATGTATTCCTCA-GACTTTTCC (SEQ ID NO:90); BB del HR 1623 3-1: 5'-GTGGAATCTCATCTTACCAA, SEQ ID NO:91) and TOPO cloned as before. Each plasmid was sequence verified prior to use. Transfection grade plasmid was prepared using the Fast-Ion MIDI PLASMID ENDO-FREE kit (IBI Scientific). rAAV packaging. BB-HDR was cloned into pAAV-MCS and packaged into using the ADENO-ASSOCIATED VIRUS HELPER-FREE system (Agilent). Briefly, a 10 cm dish AAV-293 cells was transfected with 5 µg each: pAAV-Helper, pAAV-RC and the AAV-BB-HDR plasmid. Two days post transfection, the cells were removed from the plate by scraping into 1 ml of growth media. Viral particles were released by 3 freeze-thaw cycles prior to centrifugation at maximum speed in a microcentrifuge for 5 minutes. The supernatant was aspirated and used directly for infection of target cells.

B) Polled 1592 template. A 1,784 bp fragment encompassing 383 the POLLED allele was PCR amplified (F1: 5'-GGGCAAGTTGCTCAGCTGTTTTG (SEQ ID NO:92); R1-5'-TCCGCATGGTTTAGCAGGATTCA, SEQ ID NO:93) from angus genomic DNA and TOPO cloned into the PCR 2.1 vector (Life Technologies). This plasmid was used as positive the control template for analytical primer sets and for derivation of the 1,592 bp HDR template by PCR with following primers (1594 F: 5'-ATCGAACCTGGGTCTTCTGCATTG SEQ ID NO:94;

R1: 5'-TCCGCATGGTTTAGCAGGATTCA, SEQ ID NO:95) and TOPO cloned as before. Each plasmid was sequence verified prior to use. Transfection grade plasmid was prepared using the Fast-Ion MIDI Plasmid Endo-Free kit OBI Scientific) and 5 µg or 10 µg was transfected along with 2 µg HP1.3 TALEN mRNA. Oligonucleotide templates. All oligonucleotide templates were synthesized by Integrated DNA Technologies, 100 nmole synthesis purified by standard desalting, and resuspended to 400 µM in TE.

Example 4

Tissue Culture and Transfection

Pig or cattle fibroblasts were maintained at 37 or 30° C. (as indicated) at 5% CO2 in DMEM supplemented with 10% fetal bovine serum, 100 I.U./ml penicillin and streptomycin, and 2 mM L-Glutamine. For transfection, all TALENs and HDR templates were delivered through transfection using the Neon Transfection system (Life Technologies) unless otherwise stated. Briefly, low passage Ossabaw, Landrace, Wagyu, or Holstein fibroblasts reaching 100% confluence were split 1:2 and harvested the next day at 70-80% confluence. Each transfection was comprised of 500,000-600,000 cells resuspended in buffer "R" mixed with plasmid DNA or mRNA and oligos and electroporated using the 100 µl tips by the following parameters: input Voltage; 1800V; Pulse Width; 20 ms; and Pulse Number; 1. Typically, 2-4 µg of TALEN expression plasmid or 1-2 µg of TALEN mRNA and 2-3 µM of oligos specific for the gene of interest were included in each transfection. Deviation from those amounts is indicated in the figure legends. After transfection, cells were divided 60:40 into two separate wells of a 6-well dish for three days' culture at either 30 or 37° C. respectively. After three days, cell populations were expanded and at 37° C. until at least day 10 to assess stability of edits.

Example 5

Dilution Isolation of Cellular Clones

Three days post transfection, 50 to 250 cells were seeded onto 10 cm dishes and cultured until individual colonies reached about 5 mm in diameter. At this point, 6 ml of TrypLE (Life Technologies) 1:5 (vol/vol) diluted in PBS was added and colonies were aspirated, transferred into wells of a 24-well dish well and cultured under the same 420 conditions. Colonies reaching confluence were collected and divided for cryopreservation and genotyping. Sample preparation: Transfected cells populations at day 3 and 10 were collected from a well of a 6-well dish and 10-30% were resuspended in 50 µl of 1xPCR compatible lysis buffer: 10 mM Tris-Cl pH 8.0, 2 mM EDTA, 0.45% Tryton X-100 (vol/vol), 0.45% Tween-20 (vol/vol) freshly supplemented with 200 µg/ml Proteinase K. The lysates were processed in a thermal cycler using the following program: 55° C. for 60 minutes, 95° C. for 15 minutes. Colony samples from dilution cloning were treated as above using 20-300 of lysis buffer.

Example 6

Plasmid and rAAV HDR in Wagyu Fibroblasts

Low passage Wagyu fibroblasts were cultured to 70-90% confluence and transfected by NUCLEOFECTION (Lonza) with 2 µg each TALEN expression plasmid (btGDF83.1L+ NR,) along with 750 ng of SLEEPING BEAUTY transposon components as previously described, Carlson 2012. For conditions where plasmid HDR template was used, 2 µg of BB-HDR plasmid was also included in the transfection. Transfected cells were split between two wells of a 6-well plate for culture at 30 or 37° C. For conditions using rAAV HDR template, 1500 of viral lysate was added to each well 2 hours post transfection. After incubation for three days, cells were harvested by trypsinization, a portion of which were lysed for analysis of HDR at day 3, and the remainder were plated for colony isolation as previously described, Carlson 2012.

Example 7

Mutation Detection and RFLP Analysis

PCR flanking the intended sites was conducted using PLATINUM TAQ DNA POLYMERASE HIFI (Life Technologies) with 1 µl of the cell lysate according to the manufacturer's recommendations. The frequency of mutation in a population was analysed with the SURVEYOR MUTATION DETECTION Kit (Transgenomic) according to the manufacturer's recommendations using 10 µl of the PCR product as described above. RFLP analysis was performed on 10 µl of the above PCR reaction using the indicated restriction enzyme. SURVEYOR and RFLP reactions were resolved on a 10% TBE polyacrylamide gels and visualized by ethidium bromide staining. Densitometry measurements of the bands were performed using ImageJ; and mutation rate of SURVEYOR reactions was calculated as described in Guschin et al., 201049. Percent HDR was calculated via dividing the sum intensity of RFLP fragments by the sum intensity of the parental band +RFLP fragments. For analysis of mloxP insertion, small PCR products spanning the insertion site were resolved on 10% polyacrylamide gels and the insert versus wild type alleles could be distinguished by size and quantified. RFLP analysis of colonies was treated similarly except that the PCR products were amplified by 1× MYTAQ RED Mix (Bioline) and resolved on 2.5% agarose gels. For analysis of clones for introgression of the GDF8 G938A-only (oligos lacked a novel RFLP), colonies were initially screened by a three primer assay that could distinguish between heterozygous ad homozygous introgression. Briefly, lysates from pig or cattle colonies were analysed by PCR using 1× MYTAQ RED MIX (Bioline) using the following primers and programs. Cattle GDF8 (Outside F1: 5'-CCTTGAGGTAG-GAGAGTGTTTTGGG, SEQ ID NO:96, Outside R1: 5'-TT-CACCAGAAGACAAGGAGAATTGC, SEQ ID NO:97, Inside F1: 5'-TAAGGCCAATTACTGCTCTGGAGACTA, SEQ ID NO:98; and 35 cycles of (95° C., 20 s; 62° C., 20 s; 72° C., 60 s). Pig GDF8: Outside F1: 5'-CCTTTT-TAGAAGTCAAGGTAACAGACAC, SEQ ID NO:99, Outside R1: 5'-TTGATTGGAGACATCTTTGTGGGAG, SEQ ID NO:100 Inside F1: 5'-TAAGGCCAATTACTGCTCTG-GAGATTA, SEQ ID NO:101; and 35 cycles of (95° C., 20 s; 58° C., 20 s; 72° C., 60 s). Amplicons from candidates were sequenced directly and/or TOPO cloned (Life Technologies) and sequenced by Sanger sequencing. To detect TALEN-mediated HDR at with the BB-HDR template, either 1 µl or 1 µl of a 1:10 dilution of PCR-lysate (1,000 cells/ul was added to a PCR reaction with PCR primers bt GDF8 BB 5-1 (primer "c") and primer "c" (BB-Detect 3-1-5'-GCATCGAGATTCTGTCACAATCAA, SEQ ID NO:102) and subjected to PCR with using 1× MYTAQ RED MIX (Bioline) for 40 cycles (9 459 5° C., 20 s; 66° C., 20 s; 72° C., 60 s). To confirm HDR in colonies identified by the above PCR, amplification of the entire locus was performed with primers bt GDF8 BB 5-1 and bt GDF8 BB 3-1 followed by TOPO cloning (Life Technologies) and sequencing.

Example 8

Detection of POLLED introgression was performed by PCR using the F1 primer (see above) and the "P" primer (5'-ACGTACTCTTCATTTCACAGCCTAC, SEQ ID NO:103) using 1× MyTaq Red mix (Bioline) for 38 cycles (95° C., 25 s; 62° C., 25 s; 72° C., 60 s). A second PCR assay was performed using (F2: 5'-GTCTGGGGTGAGA-TAGTTTTCTTGG, SEQ ID NO:104; R2-5'-GGCAGAGATGTTGGTCTTGGGTGT, SEQ ID NO:105). Candidates passing both tests were analysed by PCR using the flanking F1 and R1 primers followed by TOPO cloning and sequencing.

Detection of FecB introgression was performed as previously described for sheep. Callipyge introgression was detected by an AVAII RFLP assay. See results in FIG. 6.

Example 9

Amplicon Sequencing and Analysis

DNA was isolated from transfected populations and 100-250 ng was added to a 50 µl PLATINUM TAQ DNA POLYMERASE HIGH FIDELITY (Life Technologies) assembled per the manufacturer's recommendations. Each sample was assigned a primer set with a unique barcode to enable multiplex sequencing. A portion of the PCR product was resolved on a 2.5% agarose gel to confirm size prior to PCR cleanup using the MINELUTE PCR PURIFICATION Kit (Qiagen). Samples were quantified and pooled into a single sample for sequencing. The single combined sample was spiked with 25% PhiX (for sequence diversity) and sequenced on an Illumina MISEQ sequencer generating 150 base-pair paired-end reads. Read quality was assessed using FASTQC Read-pairs with overlapping ends were joined using FASTQ-JOIN from the EA-UTILS package. A custom PERL script was used to demultiplex the joined reads and count insert types. Exact matches to the forward and reverse primers were required in the demultiplexing step. Cloned animals were genotyped by RFLP assay and sequencing. Pigs, in this example and others, were cloned under contract with Minitube of America Example 10

Evaluation of Transfected mRNA as a Source of TALENs

Referring to FIG. 7, p65_11.1 TALENs were introduced into pig fibroblasts encoded by either unmodified mRNA, modified mRNA (mod mRNA) or plasmid DNA (pDNA). Two quantities of each TALEN preparation were transfected into cells by nucleofection (Lonza), cultured 3 days at 30° C. or 37° C. prior to analysis of indels. Percent NHEJ was similar for all mRNA transfections incubated at 30° C., while a dosage response could be observed for transfected cells incubated at 37° C. Notably, mRNA transfection in all groups incubated at 30° C. significantly outperformed the TALENs transfected as plasmid DNA under the same conditions. There was little difference between modified and unmodified mRNA in this test. P65_11.1 TALENs: CTCCTCCATTGCGGA-CATGGACTTCTCAGCCCTTCTGAGTCAGATC (SEQ ID NO:106), underlines indicate TALENs binding sites.

Example 11

Kinetics of TALEN Induced HDR With Oligonucleotide Templates

Referring to FIG. 8A, an mRNA source of TALENs stimulated efficient and consistent HDR using an oligo donor. Each chart displays results of targeting a specific locus in fibroblasts (e.g., ssIL2RG; "ss" for Sus scrofa and "bt" for Bos taurus) using oligo donor templates and TAL-ENs delivered as plasmid DNA or mRNA. (Insets) Diagrams of the oligo templates, in which the shaded boxes represent the TALEN-binding site and the spacers are shown in white. Each oligo contains either a 4-bp insertion (ins4) or deletion (del4) that introduces a novel restriction site for RFLP analysis. Presumptive BMs replace the conserved −1 thymidine (relative to the TALEN-binding site) with the indicated nucleotide. Fibroblasts were transfected with either TALEN-encoding plasmids (3 µg) or mRNA (1 µg) along with 3 µM of their cognate oligo-homologous template. Cells were then incubated at 37° C. or 30° C. for 3 d before expansion at 37° C. until day 10. TALEN activity was measured by the Surveyor assay at day 3 (Day3 Surveyor), and HDR was measured at days 3 and 10 by RFLP analysis (Day3% HDR and Day10% HDR). Each bar displays the average and SEM from three replicates.

Referring to FIG. 8B, porcine fibroblasts were transfected with either TALEN-encoding mRNA or plasmid DNA and oligos with 4 base pair insertions targeting LDLR or APC genes. Cells from each transfection were then evenly split into seven 24-well plate wells, cultured at 30° C. and assayed by RFLP at the indicated time points. Panel a) RFLP analysis on cell populations at indicated time points. Panel b) Results from panel a were quantified by densitometry and the averages were plotted as a function of time with SEM (n=3). HDR signal first appears 12 hours post-transfection and accumulates over time. The onset of HDR at LDLR was independent of TALEN source, but the rate of HDR between 24 and 72 hours was much higher when mRNA was used compared to plasmid DNA.

Example 12

Influence of Mutation Type on the Frequency of HDR

Referring to FIG. 9, panel a) The sequence of five oligos used to target ssLDLR. Oligos vary in length and type of mutation. TALEN binding sites are indicated in boxed text and the novel BamHI site is underlined. SNPs including BMs and insertions are circled. Panel b) Cells were transfected with LDLR2.1 TALEN mRNA (1 µg) and oligos (2 µM final). HDR at day 3 was determined by RFLP analysis and the average with SEM (n=3) was plotted. The results suggest that insertion alleles are more efficiently incorporated than SNPs or deletions, but that homology length from 46-90 bp has negligible influence on HDR efficiency. c) Cattle cells were transfected with btRosal.2 TALEN mRNA and either 41_mloxP or 60_loxP oligos (2 µM final). The numbers 41 and 60 refer to the number of homologous bases. Each oligo contains a 34 bp loxP site, either a modified (mloxP) or wild type (loxP) version, in the center of the spacer. Densitometry at day 3 and 15 show that insertion of loxP sites is both efficient and stable.

Example 13

CRISPR/Cas9 Mediated HDR to Introgress the p65 S531P Mutation From Warthogs Into Conventional Swine Referring to FIG. 10, panel a) The S531P missense mutation is caused by a T-C transition at nucleotide 1591 of porcinep65. The S-P HDR template includes the causative TC transition mutation (oversized text) which introduces a novel XmaI site and enables RFLP screening. Two gRNA sequences (P65_G1S and P65_G2A) are shown along with the p65.8 TALENs used in previous experiments. Panel b) Landrace fibroblasts were transfected with S-P-HDR oligos (2 µM), two quantities of plasmid encoding hCas9 (0.5 µg or 2.0 µg); and five quantities of the G2A transcription plasmid (0.05 to 1.0 µg). Cells from each transfection were split 60:40 for culture at 30 and 37° C. respectively for 3 days before prolonged culture at 37° C. until day 10. Surveyor assay revealed activity ranging from 16-30%. Panels c and d) RFLP analysis of cells sampled at days 3 and 10. Expected cleavage products of 191 and 118 bp are indicated by black arrows. Despite close proximity of the double stranded break (DSB) to the target SNP, CRISPR/Cas9 mediated HDR was less efficient than TALENs for introgression of S531P. Individual colonies were also analyzed using each gRNA sequence (data not shown).

Referring to FIG. 11, experiments were made for comparison of TALENs and CRISPR/Cas9 mediated HDR at porcine APC. Panel a) APC14.2 TALENs and the gRNA sequence APC14.2 Gla are shown relative to the wild type APC sequence. Below, the HDR oligo is shown which delivers a 4 bp insertion (orange text) resulting in a novel HindIII site. Pig fibroblasts transfected with 2 µM of oligo HDR template, and either 1 µg TALEN mRNA, 1 µg each plasmid DNA encoding hCas9 and the gRNA expression plasmid; or 1 µg mRNA encoding hCas9 and 0.5 Kg of gRNA expression plasmid, were then split and cultured at either 30 or 37° C. for 3 days before expansion at 37° C. until day 10. Panel b) Charts displaying RFLP and Surveyor assay results. As previously determined TALEN stimulated HDR was most efficient at 30° C., while CRISPR/Cas9 mediated HDR was most effective at 37° C. For this locus, TALENs were more effective than the CRISPR/Cas9 system for stimulation of HDR despite similar DNA cutting frequency measured by Surveyor assay. In contrast to TALENs, there was little difference in HDR when hCas9 was delivered as mRNA versus plasmid.

Example 14

SNP Introgression Using Oligo Donors

Referring to FIG. 12, panel a) The influence of blocking mutations (BM) on maintenance of HDR alleles was evaluated in pig LDLR and GDF8. Each oligo was designed to introduce the same SNPs/restriction 313 site plus or minus blocking mutations. HR was quantified in transfected populations initially cultured at 30° C. for three days and further maintained at 37° C. until day 12 by RFLP assay. The average and SEM (n=3) is shown. Panel b) Introgression of myostatin C313Y into Wagyu fibroblasts. The C313Y missense mutation is caused by a G-A transition (indicated by oversized text) at nucleotide 938 of bovine myostatin The HDR template also includes a T to C transition (circled) to introduce a novel EcoRI site for RFLP screening. Two left TALENs were designed against the locus, btGDF83.6-G, targeting the wild type alelle (Wt), and btGDF83.6-A targeting the mutant allele (C313Y); both share a common right TALEN. Transfection, culture and measurement were conducted as above. The average and SEM for btGDF83.6-G (n=30) and btGDF83.6-A (n=5) represent twelve and three biological replicates, respectively. A two-sided student's t-test was used to compare averages between groups; the p values are indicated.

Example 15

SNPs

FIG. 13 is a plot that shows results for sequence analysis of TALEN stimulated HDR alleles. PCR amplicons flanking the target site (200-250 bp total) derived from TALEN mRNA and oligo transfected cell populations were sequenced by ILLUMINA sequencing. Total read count ranged from 10,000 328 to 400,000 per sample. The count of perfect, intended HR reads versus the wild type reads is plotted for insertion (panel a) and SNP alleles (panel b). The target locus, time point and whether or not BMs were included in the oligo are indicated below. Panel c). Reads from btGDF8 and p65 were sorted for incorporation of the target SNP and then classified intended (iSNP) versus those with an additional mutation (iSNP+Mut) and plotted against the total number of reads.

Example 16

Sequence Analysis of HDR Alleles

Referring to FIG. 14, sequencing reads containing the correct insertion (Panel a) or SNP allele (Panel b) were analyzed for incorporation of BM. The target locus, time point and whether or not BMs were included in the oligo are indicated below each graph. In general, the 5' BM was incorporated most frequently into the HDR conversion tract, followed by inclusion of both BMs, or the 3' BM only. The distribution of BM is somewhat skewed towards incorporation of both BM when the intended mutation to LDLR is a SNP versus a 4 bp insertion allele. It is also interesting to note that the majority of intended reads for btGDF8 have incorporated at least one BM, but seldom have the 3' BM alone. Thus, while BM did not have a significant impact on the frequency of maintaining the intended SNP (iSNP) allele in culture, their enrichment relative to other loci suggests that they might have offered some protection from TALEN re-cleavage. c). The data of FIG. 13 panel c was further classified by mutation type and compared. Some reads contained only the iSNP, others had a concomitant indel (iSNP+indel), or a concomitant unintended SNP (iSNP+uSNP). There appears to be some elevation in the frequency of iSNP+indel when BMs were not included in the template, and the majority of indels were located in the spacer region so are likely to be the result of re-cutting of already converted alleles.

Example 17

Multiple SNPs in the TALEN DNA-Binding Site Stabilize HDR Alleles

Referring to FIG. 15, the EIF4GI gene was stabilized with multiple SNPs in the TALEN DNA binding site. Panel a) A portion of wild type EIF4GI Wt-NL is shown. One pair of TALENs was designed to cut the wild type EIF4GI to stimulate homologous recombination. Also aligned to the Wt sequence is the core sequence of the donor oligo, DF-HDR, used to introduce three SNPs (red oversized letters) into the genome. The third SNP creates a novel EagI restriction site that was used for RFLP analysis. Pig fibroblasts were transfected with EIF4GI14.1 TALEN mRNA (2 μg) and DF-HDR (2 μM) and then cultured at 30° C. for 3 days prior to analysis and colony propagation. Panel b) RFLP analysis on population three days post transfection. Expected product sizes of 344, 177 and 167 bp are indicated by filled triangles. Panel c) RFLP assay on isolated cellular clones. Day 3 cells were used to derive monoclonal colonies through dilution cloning. An example of colonies with heterozygous (open triangles) or homozygous (filled triangles) HDR alleles are indicated.

Example 18

Hypothermic Treatment for Maintenance of SNP HDR Alleles

Referring to FIG. 16, pig fibroblasts were transfected with TALEN mRNA (1 μg) and oligos (3 μM). Cells from two independent transfections were pooled for each replicate and evenly distributed into six wells of a 6-well plate and cultured at 30° C. Samples were collected from these populations for RFLP analysis on days 1-7 (minus day 6, 1D to 7D along X-axis) post-transfection and the remaining cells were transferred to 37° C. Samples for each condition were collected again at day 12 for RFLP analysis. The average HDR and SEM (n=3) is shown at the initial collection and once again at day 12.

TABLE 2

Success rate using intentional mismatches

| Locus | Species | Allele desired | Number of RVD mismatches | TALEN ID | RFLP pos. | Confirmed |
|---|---|---|---|---|---|---|
| CLPG | Goat | A to G | 0 | caCLPG1.1 | NA | 0/14 |
| CLPG | Goat | A to G | 2 | caCLPGl.1c | NA | 3/15 |
| DGAT | Cow | K232A | 0 | btDGAT 14.2 | 19/96 | 0/12 |
| DGAT | Cow | K232A | 1 | btDGAT 14.4 | 15/96 | 0/12 |
| DGAT | Cow | K232A | 1 | btDGAT 14.5 | 16/96 | 2/12 |
| DGAT | Cow | K232A | 1 | btDGAT 14.6 | 15/96 | 3/12 |
| PRLR | Cow | Trunc461 | 0 | btPRLR 9.1 | NA | 3/11 |
| SOCS2 | Pig | Trunc | 0 | ssSocs 2.1 | 75%[b] | |
| SLC35A3 | Cow | V180Fa | 0 | SL C A3 35 8.3 | 18%[b] | | a- Repair of the missense allele that results in complex vertebral malformation (Thomsen, B; Genome Res.; 2006 January; 16(1): 97-105.)
[b]Percentage of HDR on the population level Example 19

Intentional RVD Mismatches for Introgression of SNPs

Referring to FIG. 17, panel a) A TALEN pair (caCLPG 1.1) was designed to target the caCLPG region. Oligo driven HDR was utilized to introduce the desired Adenine to Guanine SNP (the targeted Adenine is boxed). The desired SNP allowed genotyping by a loss of an AvaII restriction site. Each TALEN monomer is indicated in shading above their respective binding locations. The N- and C-termini are indicated with N and C, respectively. b) Each allele of single-cell derived colonies that were resistant to AvaII were sequenced (only AvaII resistant alleles are shown). All of the alleles that contained our SNP or interest (boxed) also contained deletions (marked with dashes in the AvaII Resistant Allele sequences) or insertions (marked with dashes in the WT sequence). c) To reduce the possibility of re-binding, and subsequently re-cutting, intentional mismatches (italicized circled text) were introduced into the RVD sequence. The mismatches were placed in the RVDs directly before and/or after the RVD that would bind to the desired SNP (boxed) in right monomer of the TALEN. d) TALEN activity was measured via a Cell assay. The percent of non-homologous end joining (% NHEJ) was equivalent for 1.1 and 1.1b (28%), but was greater than 1.1 for 1.1a and 1.1c (30% and 31% respectively). The no-RNA negative control showed no TALEN activity (0%). e) Both alleles of AvaII-resistant single-cell derived colonies produced with caCLPG 1.1c were sequenced. The desired SNP is boxed. Colony 37 and 78 were heterozygous for the desired SNP and showed no additional indels. Colony 142 was homozygous for the desired SNP, but contained a 4 bp insertion on one allele.

Example 20

Mismatch Required for SNP Introgression

Referring to FIG. 18, a mismatch was required for SNP introgression. A schematic of the bovine DGAT sequence around K323A. The grey arrows represent the TALEN monomers where they bind to the DGAT sequence. The left arm consists of 16 RVDs, the right ann consists of 15 RVDs, and the spacer is 16 base pairs long. The GC and ggagct, boxed, are the targeted base pairs. The DGAT oligo converts the GC to an AA to create the desired DGAT mutant. As a marker for HDR, the boxed GGGAGC is converted to AAGCTT that creates a novel HindIII restriction site. Since this change is in the spacer, it should not affect TALEN binding as to not interfere with the intentional mismatch results. b) DGAT TALEN RVD sequences. btDGAT 14.2 contains no intentional mismatches in the RVDs. btDGAT 14.4, 14.5, and 14.6 each contain one intentional RVD mismatch at either position 1, 3, or 5 of the left TALEN monomer (circled). c) Bovine fibroblasts were transfected with 1 ug of talen and 0.4 nmoles of oligo. Three days after transfection cells were lysed, the DGAT sequence was amplified by PCR, digested with HindIII and ran on an acrylamide gel. The percent efficiency of HDR was determined by densitometry (HR). d) Sequence analysis of colonies produce with the original 14.2 TALENs. Of twelve colonies, none that were positive for the HindIII RFLP contained the desired mutation due to indels overlapping the site. e) Colonies derived from TALENs 14.5 and 14.6 produced the correct DGAT mutation and Hind111 restriction site. These two TALEN pairs produced a total of two homozygous (HH) and three heterozygous (Hh) colonies. TALEN 14.4 did not produce any colonies with the correct DGAT mutation (data not shown).

Example 21

All-in-One TALEN-HDR/Cre-RMCE

FIG. 19 depicts a process of TALEN-HDR/RMCE. The floxed cassette is transfected along with TALENs compatible with the oligo, the loxP oligo and a source of Cre recombinase. For this process to work, TALENs must cut the target loci followed by repair with the loxP oligo prior to Cre-mediated RMCE into the repaired site. The bar graph shows the number of puromycin resistant colonies produced by this method when YFC-Cre versus mCherry was included in the transfection. To confirm targeting to the SRY locus, PCR was conducted across the predicted junction (as indicated) will result in a 370 bp product. This product is apparent only when Cre is included. For this set of experiments, the following conditions were used: 600,000 cells transfected with 1ug SRY TALENs+0.3 nMol of SSCY_LoxP oligo+CLP-YFP-Cre (0.5 ug)+Floxed PTK (2 ug). The negative control had 0.5 ug of mCherry plasmid in place of CLP-YFP-Cre. SSCY_LoxP oligo:

(SEQ ID NO: 80)
TTTTATATACATTTTACACACATATATATGAAACATAACTTCGTATAGGA
GACTTTATACGAAGTTATGGATCCAAGCTTATAACTTCGTATAATGTATG
CTATACGAAGTTATTGACAGTATTAATGGCCTGAACCTAGCCAGAACT

Further Disclosure

All patents, patent applications, references, and publications set forth herein are hereby incorporated by reference herein; in case of conflict, the instant specification is controlling. The following are examples of embodiments of inventions set forth herein.

Certain embodiments are directed to hypothermic conditions for use of targeting endonucleases. For instance; 1. a hypothermic method of template-directed repair to change a chromosomal DNA of a cell, comprising introducing into a living cell a targeted nuclease system and a nucleic acid template, wherein the targeted nuclease system and the template operate to alter the chromosomal DNA to have identity to the template sequence wherein the living cell is maintained at a hypothermic culturing temperature below a physiological temperature for a time period of more than three days measured from the time of the introduction. 2. The method of 1 with the hypothermic culturing increasing a stable incorporation of the template sequence into the chromosomal DNA. 3. The method of 1 wherein the culturing temperature is kept within a range from 20 to 34° C. 4. The method of 1 wherein the time period is more than three days. 5. The method of 1 wherein the time period ranges from more than three days to about two weeks. 6. The method of 1 further comprising testing the cell for the template sequence. 7. The method of 1 wherein targeted nuclease system comprises Cas9 and Clustered Regularly Interspaced Short Palindromic Repeats (CRISPR) or a plurality of TAL effector repeat sequences that are fused to the nuclease (TALEN). 8. The method of 6 wherein the nucleic acid guide is an ssDNA. 9. The method of 1 wherein one or more of the nuclease, the nucleic acid guide, and the nucleic acid template are introduced into the cell as an mRNA. 10. The method of 1 wherein the cell is selected from the group consisting of a primary cell, a primary somatic cell, n egg, a sperm, a zygote, a germ cell, a stem cell, an oocyte, a sperm, and an embryo. 11. The method of 1 wherein the animal is homozygous for the template sequence. 12. A cell made by the method of 1.

And, for instance, 1. A method of template-directed repair to change a chromosomal DNA of a cell, comprising introducing into a living cell a targeted nuclease system, a nucleic acid template, and a cold-factor for inhibiting cell growth, wherein the targeted nuclease system and the template operate to alter the chromosomal DNA to have identity to the template sequence. 2. The method of 1 wherein the cold-factor for inhibiting cell growth, comprises Cold-inducible RNA-binding protein (CIRP). See Nishiyama et al., J. Cell Biol., (1997):137(4):899-908. 3. The method of 1 wherein the cell-cycle inhibitor is introduced by placement into a culture that comprises the cell. 4. The method of 1 wherein the cell-cycle inhibitor is introduced as a protein, as RNA, as an mRNA, or through a vector encoding the cell-cycle inhibitor. 5. The method of 4 wherein the template is a HDR template. 6. The method of 1 wherein template is an ssDNA. 7. The method of 1 wherein one or more of the nuclease system and the nucleic acid template are introduced into the cell as an mRNA. 8. The method of 1 wherein the cell is selected from the group consisting of a primary cell, a primary somatic cell, a zygote, a germ cell, a stem cell, and an embryo. 9. A genetically modified animal prepared according to the method of any of 1-8. 10. A founder animal made by the method of any of 1-9. 11. A cell made by the method of any of 1-10.

As is plainly evident, the various allelic and genetic modifications set forth herein are contemplated Embodiments of these include, for example, 1. A nonhuman animal comprising a heritable exogenous allele that provides elevated fecundity and/or a heritable exogenous allele that provides parent-of-origin dependent muscle hypertrophy. 2. The animal of 1 being a goat. 3. The animal of 1 being a chosen from the group consisting of livestock, primate, swine, cattle, horse, sheep, goat, chicken, rabbit, fish, dog, mouse, cat, rat, and laboratory animal. 4. The animal of 1 being free of fluorescent markers, selectable markers, and expressible markers. 5. The animal of 1 wherein the elevated fecundity allele is FecB; BMPR-IB. 6. The animal of 1 wherein the muscle hypertrophy allele is Callipyge. 7. The animal of 1 wherein the animal is homozygous for the exogenous allele.

And, for example, 1. A non-human animal comprising an exogenous allele for APC. 2. The animal of 1 wherein the allele is directed to a cancerous phenotype. 3. The animal of 1 wherein the exogenous allele is a human allele. 4. The animal of 1 being a laboratory animal model. 5. The animal of 1 being selected from the group consisting of pig, miniature pig, Ossabow pig, rabbit, dog, sheep, and goat. 6. The animal of 1 being a founder. 7. The animal of 1 being free of chromosomal changes other than introgression of the exogenous allele. 8. A method of making the animal of 1 comprising an HDR templated introgression of the exogenous allele with a targeted nuclease system. 9. The method of 8 wherein the exogenous allele is chosen to be a human allele that is associated with a cancerous phenotype.

And, for example, 1. An animal comprising an exogenous allele of selected from Table 1 entitled "Frequencies for recovery of colonies with HDR alleles". 2. A method comprising introgressing an allele into an animal, the allele being chosen from the group listed on said Table 1 or as follows. 3. The animal of 1 or method of 2, wherein the allele: is LDLR, e.g., for cholesterol modeling; is DAZL, e.g., for sterility; is APC, e.g., for cancer modeling; is p53; is RAG2, e.g., knocked-out for immunosuppression; is IL-2, e.g., knocked-out for immunosuppression (not in Table); is a double knock-out of RAG2 and 11-2 for immunosuppression (not in Table); is ROSA, e.g., for a safe harbor; is SRY, e.g., for modifications to a Y chromosome, for sex selection; —is KISS OR KISSR, e.g., for maturation or prevention thereof, e.g., knockout; —is GDF8, e.g., for increasing muscling in animals; —is EIF4G, e.g., for resistance to foot and mouth diseases (FMIDV); —is p65 for resistance to African Swine Fever; —is caFecB for twinning, including interspecies introgression; —is Diglyceride acyltransferase (DGAT) knockout for increased dairy merit; —is ATP-binding cassette sub-family G member 2 (ABCG2) for increased dairy merit; is pleiomorphic adenoma gene 1 (PLAG1) for influencing age at puberty, stature and body weight; is Beta lactoglobulin for reducing allergenicity of milk, is ovomucoid, ovalbumin, ovotransferrin, or lysozyme for reducing allergenicity of avian eggs. 4. A use of the animal of 1 or 3 as indicated. 5. A pig, sheep, goat, or cow with the introgressed allele of 3. 6. A cell or animal of any of 1-5. 7. The cell or animal of 6 being vertebrate, livestock, primate, swine, cattle, horse, sheep, goat, chicken, rabbit, fish, dog, mouse, cat, rat, or laboratory animal.

And, for example, 1. A method of creating a single nucleotide polymorphism (SNP) in a chromosomal DNA of a cell, comprising introducing a targeted nuclease system and a HDR template into the cell, with the targeted nuclease system comprising a DNA-binding member for specifically binding an endogenous cognate sequence in the chromosomal DNA, wherein the targeted nuclease system and the HDR template operate to alter the chromosomal DNA to have identity to the HDR template sequence, wherein the HDR template sequence comprises a SNP. 2. The method of 1 wherein the HDR template sequence comprises a plurality of SNPs. 3. The method of 1 or 2 wherein the HDR template sequence comprises an exogenous allele that replaces an endogenous allele, with the exogenous allele comprising an SNP in a sequence alignment with the endogenous allele. 4. The method of any of 1-3 being free of SNPs outside of the exogenous allele. 5. The method of 4 with the HDR template sequence being identical to the chromosomal DNA except for one or more SNPs in the exogenous allele. 6. The method of 5 wherein there is only one SNP. 7. The method of any of 1-6 wherein the HDR template is designed to reduce specific binding of the DNA-binding member to the HDR template sequence and the HDR template sequence comprises a SNP, as aligned with the chromosomal DNA.

For example: A genetically modified animal from a first breed comprising an allele of a gene selected from another species or another breed; wherein the animal of the first breed is free of genetic changes other than the allele; methods of making the animal as set forth herein.

For example: 1. A method of homology-directed repair (HDR) to introgress an exogenous allele into chromosomal DNA of a cell, comprising introducing a targeted endonuclease system and a HDR template that comprises the exogenous allele into the cell, with the targeted nuclease system comprising a DNA-binding member for specifically binding an endogenous cognate sequence in the chromosomal DNA, wherein the targeted nuclease system and the HDR template operate to alter the chromosomal DNA to have identity to the HDR template sequence to introgress the exogenous allele into the chromosomal DNA in place of an endogenous allele, with the targeting endonuclease system and/or HDR template comprising a feature to reduce specific binding of the targeting endonuclease system to DNA. 2. The method of 1 wherein the feature to reduce specific binding comprises a mismatch in the DNA-binding member sequence relative to the endogenous cognate sequence and/or a mismatch in the DNA-binding member sequence relative to the HDR template sequence. 3. The method of 2 wherein the targeted endonuclease system comprises a plurality of TAL effector repeat sequences that are fused to a nuclease (TALEN), with the TALEN comprising a sequence of Repeat Variable Diresidues (RVDs) and the mismatch is in the sequence of RVDs relative to the endogenous cognate sequence. 4. The method of 2-3 wherein the targeted nuclease system comprises a Cas9 nuclease and a guide RNA, with the mismatch being in the gRNA sequence relative to the endogenous cognate sequence. 5. The method of 2-4 wherein the targeted endonuclease system comprises a plurality of TAL effector repeat sequences that are fused to a nuclease (TALEN), with the TALEN comprising a sequence of Repeat Variable Diresidues (RVDs) and the mismatch is in the sequence of RVDs relative to the HDR template sequence. 6. The method of 2-5 wherein the targeted nuclease system comprises a Cas9 nuclease and a guide RNA, with the mismatch being in the gRNA relative to the HDR template sequence. 7. The method of 2-6 wherein the exogenous allele is a natural allele and the HDR template comprises the mismatch, with the mismatch creating a sequence that is not found in nature. 8. The method of 2-7 wherein the exogenous allele is free of mismatches and comprises DNA expressed by the cell. 9. The method of 2-8 wherein the exogenous allele is comprises the mismatch and comprises DNA expressed by the cell. 10. The method of 2-9 comprising selecting the DNA-binding member sequence and the endogenous cognate sequence so that altering the chromosomal DNA to have identity to the HDR template sequence creates the mismatch in the DNA-binding member sequence relative to the altered chromosomal DNA sequence. 11. The method of 1-8 wherein the exogenous allele is a natural allele and the HDR template consists of the natural allele and DNA that has an identity with the chromosomal DNA sequence. 12. The method of 1-8 wherein selecting the DNA-binding member sequence and the endogenous cognate sequence further comprises placing a second mismatch in the endogenous cognate sequence that is not changed when the chromosomal DNA is altered to have identity to the HDR template. 13. The method of 2-11 comprising selecting the DNA-binding member sequence and the endogenous cognate sequence to place the mismatch in the endogenous cognate sequence relative to the DNA-binding sequence, and altering the chromosomal DNA to have identity to the HDR template sequence does not remove the mismatch. 14. The method of 2-13 wherein the mismatch comprises an insertion, a deletion, or a substitution. 15. The method of 1-12 wherein the insertion, deletion, or substitution has a length from 1 to 20 residues. 16. The method of 1-14 wherein the insertion, deletion, or substitution has a length from 1 to 20 residues. 17. The method of 2 wherein the mismatch is one SNP. 18. The method of 2 comprising a plurality of mismatches. 19. The method of 1-16 wherein the targeting endonuclease system comprises a pair of TALENs that localize to the chromosomal DNA with a spacer sequence between the pair, wherein the feature comprises selecting the HDR template to create a change in a length of the spacer sequence to block cleavage of the DNA by the TALENs pair. 20. The method of 17 wherein the spacer length is decreased by a deletion or increased by an insertion. 21. The method of 17 wherein the spacer length is increased or decreased by a number of residues in a range from 1 to 60. 22. The method of any of 1-19 wherein the cell is selected from the group consisting of a primary cell, a primary somatic cell, a zygote, a germ cell, a stem cell, an oocyte, a sperm, and an embryo. 23. The method of any of 120 wherein the HDR template is an ssDNA. 24. The method of any of 1-21 wherein the nuclease system is introduced into the cell as an mRNA. 25. The method of any of 1-22 wherein the targeted nuclease system specifically binds the endogenous cognate sequence with a binding protein. 26. The method of any of 1-23 wherein the exogenous allele comprises an APC allele. 27. The method of any of 1-24 being free of reporters, fluorescent markers, selectable markers, and expressible markers. 28. The method of any of 1-25 wherein the cell is a livestock cell. 29. The method of any of 1-25 wherein the cell is from vertebrate, livestock, primate, swine, cattle, horse, sheep, goat, chicken, rabbit, fish, dog, mouse, cat, rat, and laboratory animal. 30. The method of any of 1-28 wherein the animal is homozygous for the exogenous allele. 31. A method of making a genetically modified animal comprising cloning a cell modified by the method of any of 1-30. 32. The method of any of 1-30 wherein the animal is a founder. 33. A genetically modified animal prepared according to the method of any of 1-32. 34. A founder animal made by the method of any of 1-33. 35. A cell made by the method of any of 1-30. 36. A kit comprising the targeted nuclease system and the HDR template of any of 1-34. 37. A use of any of 1-35 comprising preparing a cell for research in vitro, or preparing a cell for use in making an animal. 38. A genetically modified animal, the animal belonging to a breed having an endogenous allele in the chromosomal DNA of the animal, the animal comprising a change at an SNP, the SNP being in the endogenous allele relative to an exogenous allele found in another species or another breed of animal. Similarly, 2 A genetically modified animal, the animal belonging to a breed having an endogenous allele in the chromosomal DNA of the animal, the animal comprising an exogenous allele found in another species or another breed of animal, with the exogenous allele having a change at an SNP relative to the endogenous allele. In other words, the modified animal has an SNP so that it now has an allele that is not normally found in its breed, with that allele being from some other breed or species. The change could be only that SNP or there could be other changes, with the SNP being necessary to mirror the desired allele. The SNP is not a result of random processes, but is an intended result. 39. The animal of 38 comprising a plurality of the SNPs. 40. The animal of 38 comprising further changes in the chromosomal DNA of the animal relative to the exogenous allele. 41. The animal of any of 38-40 being free or reporters. 42. The animal of any of 38-41 being homozygous for the SNP and/or the SNPs. 43. The animal of any of 38-42 being from vertebrate, livestock, primate, swine, cattle, horse, sheep, goat, chicken, rabbit, fish, dog, mouse, cat, rat, and laboratory animal. 44. A method of creating a landing pad in a chromosomal DNA of a cell, comprising introducing a targeted nuclease system and a HDR template into the cell, with the targeted nuclease system comprising a DNA-binding member for specifically binding an endogenous cognate sequence in the chromosomal DNA, wherein the targeted nuclease system and the HDR template operate to alter the chromosomal DNA to have identity to the HDR template sequence, wherein the HDR template sequence comprises a landing pad.

What is claimed is:

1. A method for making a non-human animal, the method comprising:
   (a) introducing into a cell isolated from a non-human animal line
      (i) a CRISPR/Cas9 endonuclease;
      (ii) a guide RNA (gRNA) comprising a spacer RNA sequence that interacts with a target sequence in the chromosomal DNA of the cell;
      (iii) a homology-directed repair (HDR) template sequence encoding an allele or a gene flanked by sequences homologous to the target sequence;
   (b) introducing the cell that results from (a) into an enucleated oocyte of the same species as the non-human animal line to produce an embryo; and
   (c) implanting the embryo in a surrogate mother to produce the non-human animal, wherein said introducing step (a) results in cleavage of the chromosomal DNA at the target sequence in the cell and insertion of the HDR template sequence into the cleavage site to cause the chromosomal DNA of the cell to have identity with the HDR template sequence at the target sequence in the chromosomal DNA, thereby introgressing the allele or the gene into the chromosomal DNA of the cell, wherein the HDR template sequence also comprises a DNA sequence encoding a mismatch in the target sequence that alters the interaction with the RNA spacer sequence of the gRNA, wherein the mismatch is introduced into the chromosomal DNA of the cell and creates a sequence in the chromosomal DNA of the animal that is not found in the non-human animal line, wherein the non-human animal has a phenotypic difference relative to the non-human animal line, wherein the non-human animal line is selected from the group consisting of a swine line, a cattle line, a sheep line, a non-human primate line, a mouse line, and a rat line.

2. The method of claim 1, wherein the mismatch creates a sequence in the chromosomal DNA of the animal that is not found in the same breed as the non-human animal line.

3. The method of claim 1, wherein the target sequence encodes at least a part of an endogenous allele, wherein the HDR template sequence encodes a natural allele that is homologous to the endogenous allele flanked by sequences homologous to the target sequence in the chromosomal DNA of the animal, and wherein the natural allele replaces the endogenous allele.

4. The method of claim 1, wherein the mismatch creates a sequence that is not found in nature.

5. The method of claim 1, wherein the cell is selected from the group consisting of a primary cell, a primary somatic cell, and a stem cell.

6. The method of claim 1 wherein said CRISPR/Cas9 endonuclease is introduced into the cell as mRNA.

7. The method of claim 1, where the cell is homozygous for the allele or the gene introgression into the chromosomal DNA of the cell.

8. The method of claim 1, wherein the target sequence encodes at least part of an endogenous allele that encodes a protein or is part of a locus associated with a trait, wherein the HDR template sequence encodes a different allele that is homologous to the endogenous allele and encodes or is part of a locus associated with an enhancement of the trait flanked by sequences homologous to the target sequence in the chromosomal DNA of the cell, wherein the different allele replaces the endogenous allele, and wherein the locus is selected from the group consisting of P65/RELA and APC.

9. The method of claim 1, wherein the target sequence encodes at least part of an endogenous allele, wherein the HDR template sequence encodes an allele that is homologous to the endogenous allele flanked by sequences homologous to the target sequence in the chromosomal DNA of the cell, and wherein the allele that is homologous to the allele replaces the endogenous allele, and wherein the allele that is homologous to the endogenous allele is from the same species of animal as the non-human animal line.

10. The method of claim 1, wherein the target sequence encodes at least part of an endogenous allele, wherein the HDR template sequence encodes an allele that is homologous to the endogenous allele flanked by sequences homologous to the target sequence in the chromosomal DNA of the cell, and wherein the allele that is homologous to the endogenous allele replaces the endogenous allele, and wherein the allele that is homologous to the endogenous allele is not from the same breed of animal as the non-human animal line.

11. The method of claim 1, wherein the mismatch comprises substitution of a DNA base for a base that does not promote binding to the gRNA.

12. The method of claim 11, wherein said substitution comprises a 1 to 5 base pair substitution.

13. The method of claim 1, wherein the mismatch comprises an insertion or a deletion of a DNA base.

14. The method of claim 13, wherein the mismatch comprises an insertion of 1-5 DNA bases.

15. The method of claim 13, wherein the mismatch comprises a deletion of 1-5 DNA bases.

16. The method of claim 1, wherein the target sequence encodes at least part of an endogenous allele, wherein the HDR template sequence encodes an allele that is homologous to the endogenous allele flanked by sequences homologous to the target sequence in the chromosomal DNA of the cell, wherein the allele that is homologous to the endogenous allele replaces the endogenous allele, and wherein the mismatch comprises a single nucleotide polymorphism (SNP) that is located within the allele that is homologous to the endogenous allele.

17. The method of claim 1, wherein the target sequence encodes at least part of an endogenous allele, wherein the HDR template sequence encodes an allele that is homologous to the endogenous allele flanked by sequences homologous to the target sequence in the chromosomal DNA of the cell, wherein the allele that is homologous to the endogenous allele replaces the endogenous allele, and wherein the mismatch consists of a SNP, that is located within the allele that is homologous to the endogenous allele.

18. The of claim 1, wherein the target sequence encodes at least part of an endogenous allele, wherein the HDR template sequence encodes an allele that is homologous to the endogenous allele flanked by sequences homologous to the target sequence in the chromosomal DNA of the cell, wherein the allele that is homologous to the endogenous allele replaces the endogenous allele, and wherein the mismatch comprises a plurality of SNPs that is located within the allele that is homologous to the endogenous allele.

19. The method of claim 1, wherein the target sequence encodes at least part of an endogenous allele, wherein the HDR template sequence encodes an allele that is homologous to the endogenous allele flanked by sequences homologous to the target sequence in the chromosomal DNA of the cell, wherein the allele that is homologous to the endogenous allele replaces the endogenous allele, and wherein the mismatch consists of a plurality of SNPs that is located within the allele that is homologous to the endogenous allele.

20. The method of claim 1, wherein the allele is a SNP.

* * * * *

SEQUENCE LISTING

```
<160> NUMBER OF SEQ ID NOS: 106

<210> SEQ ID NO 1
<211> LENGTH: 90
<212> TYPE: DNA
<213> ORGANISM: sus scrofa

<400> SEQUENCE: 1
tgccgagacg ggaaatgaat ctcctacaag tggatttgtg atgggaacac cgagtgcaag      60
gacgggtccg atgagtccct ggagacgtgc                                     90

<210> SEQ ID NO 2
<211> LENGTH: 46
<212> TYPE: DNA
<213> ORGANISM: Artificial Sequence
<220> FEATURE:
<223> OTHER INFORMATION: HDR template

<400> SEQUENCE: 2
cctacaagtg gatttgtggg atccacaccg agtgtaagga cgggtc                    46

<210> SEQ ID NO 3
<211> LENGTH: 60
<212> TYPE: DNA
<213> ORGANISM: Artificial Sequence
<220> FEATURE:
<223> OTHER INFORMATION: HDR template

<400> SEQUENCE: 3
tgcacctcct acaagtggat ttgtgggatc cacaccgagt gcaaggacgg gtccgctgag      60

<210> SEQ ID NO 4
<211> LENGTH: 90
<212> TYPE: DNA
<213> ORGANISM: Artificial Sequence
<220> FEATURE:
<223> OTHER INFORMATION: HDR template
```

-continued

<400> SEQUENCE: 4
tgccgagacg ggaaatgcat ctcctacaag tggatttgtg ggatccacac cgagtgcaag    60
gacgggtccg atgagtccct ggagacgtgc                                    90

<210> SEQ ID NO 5
<211> LENGTH: 89
<212> TYPE: DNA
<213> ORGANISM: Artificial Sequence
<220> FEATURE:
<223> OTHER INFORMATION: HDR template

<400> SEQUENCE: 5
ccgagacggg aaatgcacct cctacaagtg gatttgtgat ggatccgaac accgagtgca    60
aggacgggtc cgctgagtcc ctggagacg                                     89

<210> SEQ ID NO 6
<211> LENGTH: 86
<212> TYPE: DNA
<213> ORGANISM: Artificial Sequence
<220> FEATURE:
<223> OTHER INFORMATION: HDR template

<400> SEQUENCE: 6
tgccgagacg ggaaatgcac ctcctacaag tggatttggg atccaccgag tgcaaggacg    60
ggtccgctga gtccctggag acgtgc                                        86

<210> SEQ ID NO 7
<211> LENGTH: 23
<212> TYPE: DNA
<213> ORGANISM: Artificial Sequence
<220> FEATURE:
<223> OTHER INFORMATION: Guide sequence

<400> SEQUENCE: 7
gctcaccaac ggtctcctct cgg                                           23

<210> SEQ ID NO 8
<211> LENGTH: 22
<212> TYPE: DNA
<213> ORGANISM: Artificial Sequence
<220> FEATURE:
<223> OTHER INFORMATION: Guide Sequence

<400> SEQUENCE: 8
gttgccagag gagagccccc tg                                            22

<210> SEQ ID NO 9
<211> LENGTH: 92
<212> TYPE: DNA
<213> ORGANISM: sus scrofa

<400> SEQUENCE: 9
gggcctctgg gctcaccaac ggtctcctct cggggacga agacttctcc tccattgcgg    60
acatggactt ctcagccctt ctgagtcaga tc                                 92

<210> SEQ ID NO 10
<211> LENGTH: 90
<212> TYPE: DNA
<213> ORGANISM: Artificial Sequence
<220> FEATURE:
<223> OTHER INFORMATION: HDR template

<400> SEQUENCE: 10
gggcctctgg gctcaccaac ggtctcctcc cggggacga agacttctcc tccattgcgg  60
acatggactt ctcagccctt ctgagtcaga  90

<210> SEQ ID NO 11
<211> LENGTH: 15
<212> TYPE: DNA
<213> ORGANISM: Artificial sequence
<220> FEATURE:
<223> OTHER INFORMATION: TALENs

<400> SEQUENCE: 11
ctcctccatt gcgga  15

<210> SEQ ID NO 12
<211> LENGTH: 15
<212> TYPE: DNA
<213> ORGANISM: Artificial Sequence
<220> FEATURE:
<223> OTHER INFORMATION: TALENs

<400> SEQUENCE: 12
cttctgagtc agatc  15

<210> SEQ ID NO 13
<211> LENGTH: 18
<212> TYPE: DNA
<213> ORGANISM: Artificial Sequence
<220> FEATURE:
<223> OTHER INFORMATION: TALENs

<400> SEQUENCE: 13
ggaagaagta tcagccat  18

<210> SEQ ID NO 14
<211> LENGTH: 15
<212> TYPE: DNA
<213> ORGANISM: Artificial Sequence
<220> FEATURE:
<223> OTHER INFORMATION: TALENs

<400> SEQUENCE: 14
acagaaattc tgggt  15

<210> SEQ ID NO 15
<211> LENGTH: 23
<212> TYPE: DNA
<213> ORGANISM: Artificial Sequence
<220> FEATURE:
<223> OTHER INFORMATION: guide sequence

<400> SEQUENCE: 15
gggagggtcc ttctgtcttt aag  23

<210> SEQ ID NO 16
<211> LENGTH: 86
<212> TYPE: DNA
<213> ORGANISM: sus scrofa

<400> SEQUENCE: 16
ccagatcgcc aaatgcatgg aagaagtatc agccattcat ccctcccagg aagacagaaa  60
ttctgggtca accacggagt tgcact  86

```
<210> SEQ ID NO 17
<211> LENGTH: 89
<212> TYPE: DNA
<213> ORGANISM: Artificial Sequence
<220> FEATURE:
<223> OTHER INFORMATION: HDR template

<400> SEQUENCE: 17
ccagatcgcc aaagtcacgg aagaagtatc agccattcat ccctcccagt gaacttacag     60
aaattctggg tcgaccacgg agttgcact                                       89

<210> SEQ ID NO 18
<211> LENGTH: 58
<212> TYPE: DNA
<213> ORGANISM: Artificial Sequence
<220> FEATURE:
<223> OTHER INFORMATION: HDR template

<400> SEQUENCE: 18
aaggccaatt actgctctgg agaatatgaa ttcgtatttt tgcaaaagta tcctcata       58

<210> SEQ ID NO 19
<211> LENGTH: 14
<212> TYPE: DNA
<213> ORGANISM: Artificial Sequence
<220> FEATURE:
<223> OTHER INFORMATION: HDR template

<400> SEQUENCE: 19
gctctggaga atgt                                                       14

<210> SEQ ID NO 20
<211> LENGTH: 58
<212> TYPE: DNA
<213> ORGANISM: sus scrofa

<400> SEQUENCE: 20
aaggccaatt actgctctgg agaatgtgaa tttgtatttt tgcaaaagta tcctcata       58

<210> SEQ ID NO 21
<211> LENGTH: 14
<212> TYPE: DNA
<213> ORGANISM: Artificial Sequence
<220> FEATURE:
<223> OTHER INFORMATION: TALEN

<400> SEQUENCE: 21
gctctggaga atat                                                       14

<210> SEQ ID NO 22
<211> LENGTH: 14
<212> TYPE: DNA
<213> ORGANISM: Artificial Sequence
<220> FEATURE:
<223> OTHER INFORMATION: TALEN

<400> SEQUENCE: 22
aaaagtatcc tcat                                                       14

<210> SEQ ID NO 23
<211> LENGTH: 53
<212> TYPE: DNA
<213> ORGANISM: Bos taurus
```

<400> SEQUENCE: 23 tccgtcctttt gccaaccttg gccgaccagc ccttagcaac cgtgggcccc caa                53

<210> SEQ ID NO 24
<211> LENGTH: 18
<212> TYPE: DNA
<213> ORGANISM: Artificial Sequence
<220> FEATURE:
<223> OTHER INFORMATION: TALENs

<400> SEQUENCE: 24
ccgtcctttg ccaacctt                18

<210> SEQ ID NO 25
<211> LENGTH: 18
<212> TYPE: DNA
<213> ORGANISM: Artificial Sequence
<220> FEATURE:
<223> OTHER INFORMATION: TALENs

<400> SEQUENCE: 25
agcaaccgtg ggcccca                18

<210> SEQ ID NO 26
<211> LENGTH: 53
<212> TYPE: DNA
<213> ORGANISM: Artificial Sequence
<220> FEATURE:
<223> OTHER INFORMATION: TALENs

<400> SEQUENCE: 26 tccgtcctttt gccgacttcg gccgaccagc ccttagcaac cgtgggcccc caa                53

<210> SEQ ID NO 27
<211> LENGTH: 22
<212> TYPE: DNA
<213> ORGANISM: Ovis aries

<400> SEQUENCE: 27
gctgagagcg caggaatcca gg                22

<210> SEQ ID NO 28
<211> LENGTH: 22
<212> TYPE: DNA
<213> ORGANISM: Ovis aries

<400> SEQUENCE: 28
cgactctcgc gtccttaggt cc                22

<210> SEQ ID NO 29
<211> LENGTH: 21
<212> TYPE: DNA
<213> ORGANISM: Ovis aries

<400> SEQUENCE: 29
gctgggacca cctgtcagat c                21

<210> SEQ ID NO 30
<211> LENGTH: 21
<212> TYPE: DNA
<213> ORGANISM: Ovis aries

<400> SEQUENCE: 30
cgaccctggt ggacagtcta g                21

<210> SEQ ID NO 31
<211> LENGTH: 58
<212> TYPE: DNA
<213> ORGANISM: Ovies aries

<400> SEQUENCE: 31
gctgagagcg caggaatcca ggcgcagggg cccgagggct gggaccacct gtcagatc        58

<210> SEQ ID NO 32
<211> LENGTH: 30
<212> TYPE: DNA
<213> ORGANISM: Artificial Sequence
<220> FEATURE:
<223> OTHER INFORMATION: Artificial allele of caCLPG

<400> SEQUENCE: 32
gctgagagcg ctggggccac ctgtcaggtc        30

<210> SEQ ID NO 33
<211> LENGTH: 50
<212> TYPE: DNA
<213> ORGANISM: Artificial Sequence
<220> FEATURE:
<223> OTHER INFORMATION: Artificial allele of caCLPG

<400> SEQUENCE: 33
gctgagagcg caggaatcca ggcgcgaggg ctggggccac ctgtcagatc        50

<210> SEQ ID NO 34
<211> LENGTH: 39
<212> TYPE: DNA
<213> ORGANISM: Artificial Sequence
<220> FEATURE:
<223> OTHER INFORMATION: Artificial allele of caCLPG

<400> SEQUENCE: 34
gctgagagcg caggaatcct gcgggccacc tgtcagatc        39

<210> SEQ ID NO 35
<211> LENGTH: 32
<212> TYPE: DNA
<213> ORGANISM: Artificial Sequence
<220> FEATURE:
<223> OTHER INFORMATION: Artificial allele of caCLPG

<400> SEQUENCE: 35
gctgaccgag ggctggggcc acctgtcaga tc        32

<210> SEQ ID NO 36
<211> LENGTH: 54
<212> TYPE: DNA
<213> ORGANISM: Artificial Sequence
<220> FEATURE:
<223> OTHER INFORMATION: Artificial allele of caCLPG

<400> SEQUENCE: 36
ctgagagcgc aggaatccag gcgcagggcg agggctgggg ccacctgtca gatc        54

<210> SEQ ID NO 37
<211> LENGTH: 59
<212> TYPE: DNA
<213> ORGANISM: Artificial Sequence
<220> FEATURE:
<223> OTHER INFORMATION: Artificial allele of caCLPG

```
<400> SEQUENCE: 37
gctgagagcg ctggaatcca ggcgcagggg ccccgagggc tggggccacc agtcagatc     59

<210> SEQ ID NO 38
<211> LENGTH: 61
<212> TYPE: DNA
<213> ORGANISM: Artificial Sequence
<220> FEATURE:
<223> OTHER INFORMATION: Artificial allele of caCLPG

<400> SEQUENCE: 38
gctgagagcg caggaatcca ggcgcagggg gggcccgagg ctgggggcca cctgtcagat    60
c                                                                    61

<210> SEQ ID NO 39
<211> LENGTH: 55
<212> TYPE: DNA
<213> ORGANISM: Artificial Sequence
<220> FEATURE:
<223> OTHER INFORMATION: Artificial allele of caCLPG

<400> SEQUENCE: 39
gctgagagcg caggaatcca ggcgcagggc gagggctggg gccacctgtc agatc          55

<210> SEQ ID NO 40
<211> LENGTH: 54
<212> TYPE: DNA
<213> ORGANISM: Artificial Sequence
<220> FEATURE:
<223> OTHER INFORMATION: Artificial allele of caCLPG

<400> SEQUENCE: 40
ctgagagcgc aggaatccag gcgcgatccg agggctgggg ccacctgtca gatc           54

<210> SEQ ID NO 41
<211> LENGTH: 50
<212> TYPE: DNA
<213> ORGANISM: Artificial Sequence
<220> FEATURE:
<223> OTHER INFORMATION: Artificial allele of caCLPG

<400> SEQUENCE: 41
gctgagagcg caggaatcca ggcgcgaggg ctggggccac ccgtcagatc                50

<210> SEQ ID NO 42
<211> LENGTH: 55
<212> TYPE: DNA
<213> ORGANISM: Artificial Sequence
<220> FEATURE:
<223> OTHER INFORMATION: Artificial allele of caCLPG

<400> SEQUENCE: 42
gctgagagcg caggaatcca ggcgcgatcc gagggctggg gccacctgtc agatc           55

<210> SEQ ID NO 43
<211> LENGTH: 45
<212> TYPE: DNA
<213> ORGANISM: Artificial Sequence
<220> FEATURE:
<223> OTHER INFORMATION: Artificial allele of caCLPG

<400> SEQUENCE: 43
gctgagagcg caggaatcca ggcgcagggg cccacctgtc agatc                     45
```

```
<210> SEQ ID NO 44
<211> LENGTH: 30
<212> TYPE: DNA
<213> ORGANISM: Artificial Sequence
<220> FEATURE:
<223> OTHER INFORMATION: Artificial allele of caCLPG

<400> SEQUENCE: 44
gctgagagcg ctggggccac ctgtcagatc                               30

<210> SEQ ID NO 45
<211> LENGTH: 55
<212> TYPE: DNA
<213> ORGANISM: Artificial Sequence
<220> FEATURE:
<223> OTHER INFORMATION: Artificial allele of caCLPG

<400> SEQUENCE: 45
gctgagagcg caggaatcca cgcgcagggc gagggctggg gccacctgtc agatc    55

<210> SEQ ID NO 46
<211> LENGTH: 38
<212> TYPE: PRT
<213> ORGANISM: Artificial Sequence
<220> FEATURE:
<223> OTHER INFORMATION: TALENs repeat variable di-residues

<400> SEQUENCE: 46

Asn Asn Asn Ile Asn Asn Asn Ile Asn Asn His Asp Asn Asn His Asp
1               5                   10                  15

Asn Ile Asn Asn Asn Asn Asn Ile Asn Ile Asn Gly His Asp His Asp
            20                  25                  30

Asn Ile Asn Asn Asn Asn
        35

<210> SEQ ID NO 47
<211> LENGTH: 38
<212> TYPE: PRT
<213> ORGANISM: Artificial Sequence
<220> FEATURE:
<223> OTHER INFORMATION: TALENs reapeat variable di-residues

<400> SEQUENCE: 47

Asn Asn Asn Ile Asn Asn Asn Ile Asn Asn His Asp Asn Asn His Asp
1               5                   10                  15

Asn Ile Asn Asn Asn Asn Asn Ile Asn Ile Asn Gly His Asp His Asp
            20                  25                  30

Asn Ile Asn Asn Asn Asn
        35

<210> SEQ ID NO 48
<211> LENGTH: 38
<212> TYPE: PRT
<213> ORGANISM: Artificial Sequence
<220> FEATURE:
<223> OTHER INFORMATION: TALENs repeat variable di-residues

<400> SEQUENCE: 48

Asn Asn Asn Ile Asn Asn Asn Ile Asn Asn His Asp Asn Asn His Asp
1               5                   10                  15

Asn Ile Asn Asn Asn Asn Asn Ile Asn Ile Asn Gly His Asp His Asp
            20                  25                  30

Asn Ile Asn Asn Asn Asn
        35
```

```
<210> SEQ ID NO 49
<211> LENGTH: 38
<212> TYPE: PRT
<213> ORGANISM: Artificial Sequence
<220> FEATURE:
<223> OTHER INFORMATION: TALENs repeat variable di-residues

<400> SEQUENCE: 49

Asn Asn Asn Ile Asn Asn Asn Ile Asn Asn His Asp Asn Asn His Asp
1               5                   10                  15

Asn Ile Asn Asn Asn Asn Asn Ile Asn Ile Asn Gly His Asp His Asp
            20                  25                  30

Asn Ile Asn Asn Asn Asn
        35

<210> SEQ ID NO 50
<211> LENGTH: 36
<212> TYPE: PRT
<213> ORGANISM: Artificial Sequence
<220> FEATURE:
<223> OTHER INFORMATION: TALENs repeat variable di-residues

<400> SEQUENCE: 50

His Asp Asn Gly Asn Asn Asn Ile His Asp Asn Ile Asn Asn Asn Asn
1               5                   10                  15

Asn Gly Asn Asn Asn Asn Asn Gly His Asp His Asp His Asp Asn Ile
            20                  25                  30

Asn Asn His Asp
        35

<210> SEQ ID NO 51
<211> LENGTH: 36
<212> TYPE: PRT
<213> ORGANISM: Artificial Sequence
<220> FEATURE:
<223> OTHER INFORMATION: TALENs repeat variable di-residues

<400> SEQUENCE: 51

His Asp Asn Gly Asn Asn Asn Ile His Asp Asn Ile Asn Asn Asn Asn
1               5                   10                  15

Asn Gly Asn Asn Asn Asn Asn Gly Asn Ile His Asp His Asp Asn Ile
            20                  25                  30

Asn Asn His Asp
        35

<210> SEQ ID NO 52
<211> LENGTH: 36
<212> TYPE: PRT
<213> ORGANISM: Artificial Sequence
<220> FEATURE:
<223> OTHER INFORMATION: TALENs repeat variable di-residues

<400> SEQUENCE: 52

His Asp Asn Gly Asn Asn Asn Ile His Asp Asn Ile Asn Asn Asn Asn
1               5                   10                  15

Asn Gly Asn Asn Asn Ile Asn Gly His Asp His Asp His Asp Asn Ile
            20                  25                  30

Asn Asn His Asp
        35
```

```
<210> SEQ ID NO 53
<211> LENGTH: 36
<212> TYPE: PRT
<213> ORGANISM: Artificial Sequence
<220> FEATURE:
<223> OTHER INFORMATION: TALENs repeat variable di-residues

<400> SEQUENCE: 53

His Asp Asn Gly Asn Asn Asn Ile His Asp Asn Ile Asn Asn Asn Asn
1               5                   10                  15

Asn Gly Asn Asn Asn Ile Asn Gly Asn Ile His Asp His Asp Asn Ile
            20                  25                  30

Asn Asn His Asp
        35

<210> SEQ ID NO 54
<211> LENGTH: 58
<212> TYPE: DNA
<213> ORGANISM: Artificial Sequence
<220> FEATURE:
<223> OTHER INFORMATION: Artificial allele

<400> SEQUENCE: 54
gctgagagcg caggaatcca ggcgcagggg cccgagggct ggaccaccct gtcagatc         58

<210> SEQ ID NO 55
<211> LENGTH: 58
<212> TYPE: DNA
<213> ORGANISM: Artificial Sequence
<220> FEATURE:
<223> OTHER INFORMATION: Artificial Allele

<400> SEQUENCE: 55
gctgagagcg caggaatcca ggcgcagggg cccgagggct ggggccacct gtcagatc         58

<210> SEQ ID NO 56
<211> LENGTH: 58
<212> TYPE: DNA
<213> ORGANISM: Artificial Sequence
<220> FEATURE:
<223> OTHER INFORMATION: Artifical Allele

<400> SEQUENCE: 56
gctgagagcg caggaatccg ggcgcagggg cccgagggct ggaccaccct gtcagatc         58

<210> SEQ ID NO 57
<211> LENGTH: 58
<212> TYPE: DNA
<213> ORGANISM: Artificial Sequence
<220> FEATURE:
<223> OTHER INFORMATION: Artificial Allele

<400> SEQUENCE: 57
gctgagagcg caggaatcca ggcgcagggg cccgagggct ggggccacct gtcagatc         58

<210> SEQ ID NO 58
<211> LENGTH: 58
<212> TYPE: DNA
<213> ORGANISM: Artificial Sequence
<220> FEATURE:
<223> OTHER INFORMATION: Artificial Allele

<400> SEQUENCE: 58
gctgagagcg caggaatcca ggcgcagggg cccgagggct gggaccacct gtcagatc         58
```

```
<210> SEQ ID NO 59
<211> LENGTH: 58
<212> TYPE: DNA
<213> ORGANISM: Artificial Sequence
<220> FEATURE:
<223> OTHER INFORMATION: Artificial Allele

<400> SEQUENCE: 59
gctgagagcg caggaatcca ggcgcagggg cccgagggct ggggccacct gtcagatc      58

<210> SEQ ID NO 60
<211> LENGTH: 62
<212> TYPE: DNA
<213> ORGANISM: Ovis aries

<400> SEQUENCE: 60
gctgagagcg caggaatcca ggcgcagggg cgggcccgag ggctggggcc acctgtcaga    60
tc                                                                  62

<210> SEQ ID NO 61
<211> LENGTH: 48
<212> TYPE: DNA
<213> ORGANISM: Bos taurus

<400> SEQUENCE: 61
tggcaggtaa ggcggccaac gggggagctg cccagcgcac cgtgagct                 48

<210> SEQ ID NO 62
<211> LENGTH: 48
<212> TYPE: DNA
<213> ORGANISM: Bos taurus

<400> SEQUENCE: 62
accgtccatt ccgccggttg ccccctcgac gggtcgcgtg gcactcga                 48

<210> SEQ ID NO 63
<211> LENGTH: 32
<212> TYPE: PRT
<213> ORGANISM: Artificial Sequence
<220> FEATURE:
<223> OTHER INFORMATION: TALENs repeat variable di-residues

<400> SEQUENCE: 63

Asn Asn Asn Asn His Asp Asn Ile Asn Asn Asn Asn Gly Asn Ile
1               5                   10                  15

Asn Ile Asn Asn Asn Asn His Asp Asn Asn Asn Asn His Asp His Asp
            20                  25                  30

<210> SEQ ID NO 64
<211> LENGTH: 30
<212> TYPE: PRT
<213> ORGANISM: Artificial Sequence
<220> FEATURE:
<223> OTHER INFORMATION: TALENs repeat variable di-residues

<400> SEQUENCE: 64

Asn Ile Asn Asn His Asp Asn Gly His Asp Asn Ile His Asp Asn Asn
1               5                   10                  15

Asn Asn Asn Gly Asn Asn His Asp Asn Asn His Asp Asn Gly
            20                  25                  30
```

```
<210> SEQ ID NO 65
<211> LENGTH: 32
<212> TYPE: PRT
<213> ORGANISM: Artificial Sequence
<220> FEATURE:
<223> OTHER INFORMATION: TALENs repeat variable di-residues

<400> SEQUENCE: 65

His Asp Asn Asn His Asp Asn Ile Asn Asn Asn Asn Gly Asn Ile
1               5                   10                  15

Asn Ile Asn Asn Asn Asn His Asp Asn Asn Asn His Asp His Asp
            20                  25                  30

<210> SEQ ID NO 66
<211> LENGTH: 30
<212> TYPE: PRT
<213> ORGANISM: Artificial Sequence
<220> FEATURE:
<223> OTHER INFORMATION: TALENs repeat variable di-residue

<400> SEQUENCE: 66

Asn Ile Asn Asn His Asp Asn Gly His Asp Asn Ile His Asp Asn Asn
1               5                   10                  15

Asn Asn Asn Gly Asn Asn His Asp Asn Asn His Asp Asn Gly
            20                  25                  30

<210> SEQ ID NO 67
<211> LENGTH: 32
<212> TYPE: PRT
<213> ORGANISM: Artificial Sequence
<220> FEATURE:
<223> OTHER INFORMATION: TALENs repeate variable di-residue

<400> SEQUENCE: 67

Asn Asn Asn Asn Asn Ile Asn Ile Asn Asn Asn Asn Gly Asn Ile
1               5                   10                  15

Asn Ile Asn Asn Asn Asn His Asp Asn Asn Asn Asn His Asp His Asp
            20                  25                  30

<210> SEQ ID NO 68
<211> LENGTH: 30
<212> TYPE: PRT
<213> ORGANISM: Artificial Sequence
<220> FEATURE:
<223> OTHER INFORMATION: TALENs repeat variable di-residue

<400> SEQUENCE: 68

Asn Ile Asn Asn His Asp Asn Gly His Asp Asn Ile His Asp Asn Asn
1               5                   10                  15

Asn Asn Asn Gly Asn Asn His Asp Asn Asn His Asp Asn Gly
            20                  25                  30

<210> SEQ ID NO 69
<211> LENGTH: 32
<212> TYPE: PRT
<213> ORGANISM: Artificial Sequence
<220> FEATURE:
<223> OTHER INFORMATION: TALENs repeat variable di-residue

<400> SEQUENCE: 69

Asn Asn Asn Asn His Asp Asn Ile His Asp Asn Asn Asn Gly Asn Ile
1               5                   10                  15

Asn Ile Asn Asn Asn Asn His Asp Asn Asn Asn Asn His Asp His Asp
            20                  25                  30
```

<210> SEQ ID NO 70
<211> LENGTH: 30
<212> TYPE: PRT
<213> ORGANISM: Artificial Sequence
<220> FEATURE:
<223> OTHER INFORMATION: TALENs repeat variable di-residue

<400> SEQUENCE: 70

Asn Ile Asn Asn His Asp Asn Gly His Asp Asn Ile His Asp Asn Asn
1               5                   10                  15

Asn Asn Asn Gly Asn Asn His Asp Asn Asn His Asp Asn Gly
            20                  25                  30

<210> SEQ ID NO 71
<211> LENGTH: 47
<212> TYPE: DNA
<213> ORGANISM: Artificial Sequence
<220> FEATURE:
<223> OTHER INFORMATION: Artificial Allele

<400> SEQUENCE: 71
gcaggtaaga aggccaacgg aagctttgcc cagcgcaccg tgagcta                    47

<210> SEQ ID NO 72
<211> LENGTH: 44
<212> TYPE: DNA
<213> ORGANISM: Artificial Sequence
<220> FEATURE:
<223> OTHER INFORMATION: Artificial Allele

<400> SEQUENCE: 72
gcaggttagg cagccaaccg agctgtacac cgcccctga gctt                        44

<210> SEQ ID NO 73
<211> LENGTH: 42
<212> TYPE: DNA
<213> ORGANISM: Artificial Sequence
<220> FEATURE:
<223> OTHER INFORMATION: Artificial Allele

<400> SEQUENCE: 73
gcaggtaagg cggccaacgc taccccaccc acccggggct ta                         42

<210> SEQ ID NO 74
<211> LENGTH: 44
<212> TYPE: DNA
<213> ORGANISM: Artificial Sequence
<220> FEATURE:
<223> OTHER INFORMATION: Artificial Allele

<400> SEQUENCE: 74
gcaggtaagg cggccaacgg gacttcccat tggaccgtga gcta                       44

<210> SEQ ID NO 75
<211> LENGTH: 45
<212> TYPE: DNA
<213> ORGANISM: Artificial Sequence
<220> FEATURE:
<223> OTHER INFORMATION: Artificial Allele

<400> SEQUENCE: 75
gcaggtaagg cggccaacgg ggtctgccca gcacaacggg agcta                      45

```
<210> SEQ ID NO 76
<211> LENGTH: 43
<212> TYPE: DNA
<213> ORGANISM: Artificial Sequence
<220> FEATURE:
<223> OTHER INFORMATION: Artificial Allele

<400> SEQUENCE: 76
gcaggtaagg cggccaacct gctccccaca ccacgagcta cta          43

<210> SEQ ID NO 77
<211> LENGTH: 43
<212> TYPE: DNA
<213> ORGANISM: Artificial Sequence
<220> FEATURE:
<223> OTHER INFORMATION: Artificial Allele

<400> SEQUENCE: 77
gcaggtaagg cggccaacga ggtgcccccg ggagctaccc cta          43

<210> SEQ ID NO 78
<211> LENGTH: 42
<212> TYPE: DNA
<213> ORGANISM: Artificial Sequence
<220> FEATURE:
<223> OTHER INFORMATION: Artificial Allele

<400> SEQUENCE: 78
gcaggtaagg cggccaactg ccgcccacac caccagctac cc           42

<210> SEQ ID NO 79
<211> LENGTH: 35
<212> TYPE: DNA
<213> ORGANISM: Artificial Sequence
<220> FEATURE:
<223> OTHER INFORMATION: Artificial Allele

<400> SEQUENCE: 79
gcaggtaagg cggccgccca gctgcccgtg agcta                   35

<210> SEQ ID NO 80
<211> LENGTH: 148
<212> TYPE: DNA
<213> ORGANISM: Artificial Sequence
<220> FEATURE:
<223> OTHER INFORMATION: HDR template

<400> SEQUENCE: 80
ttttatatac attttacaca catatatatg aaacataact tcgtatagga gactttatac    60
gaagttatgg atccaagctt ataacttcgt ataatgtatg ctatacgaag ttattgacag   120
tattaatggc ctgaacctag ccagaact                                      148

<210> SEQ ID NO 81
<211> LENGTH: 47
<212> TYPE: DNA
<213> ORGANISM: Artificial Sequence
<220> FEATURE:
<223> OTHER INFORMATION: Artificial Allele

<400> SEQUENCE: 81
gcaggtaagg gggacaggtt acaaggaacc catggcaccg tgagcta               47
```

```
<210> SEQ ID NO 82
<211> LENGTH: 34
<212> TYPE: DNA
<213> ORGANISM: Artificial Sequence
<220> FEATURE:
<223> OTHER INFORMATION: Artificial Allele

<400> SEQUENCE: 82
caggtaagaa ggccaacgga agctttgccc agcg                              34

<210> SEQ ID NO 83
<211> LENGTH: 34
<212> TYPE: DNA
<213> ORGANISM: Artificial Sequence
<220> FEATURE:
<223> OTHER INFORMATION: Artificial Allele

<400> SEQUENCE: 83
caggtaagaa ggccaacgga agctttgccc agcg                              34

<210> SEQ ID NO 84
<211> LENGTH: 34
<212> TYPE: DNA
<213> ORGANISM: Artificial Sequence
<220> FEATURE:
<223> OTHER INFORMATION: Artificial Allele

<400> SEQUENCE: 84
caggtaagaa ggccaacgga agctttgccc agcg                              34

<210> SEQ ID NO 85
<211> LENGTH: 34
<212> TYPE: DNA
<213> ORGANISM: Artificial Sequence
<220> FEATURE:
<223> OTHER INFORMATION: Artificial Allele

<400> SEQUENCE: 85
caggtaagaa ggccaacgga agctttgccc agcg                              34

<210> SEQ ID NO 86
<211> LENGTH: 34
<212> TYPE: DNA
<213> ORGANISM: Artificial Sequence
<220> FEATURE:
<223> OTHER INFORMATION: Artificial Allele

<400> SEQUENCE: 86
caggtaagaa ggccaacgga agctttgccc agcg                              34

<210> SEQ ID NO 87
<211> LENGTH: 34
<212> TYPE: DNA
<213> ORGANISM: Artificial Sequence
<220> FEATURE:
<223> OTHER INFORMATION: Artificial Allele

<400> SEQUENCE: 87
caggtaagaa ggccaacgga agctttgccc agcg                              34

<210> SEQ ID NO 88
<211> LENGTH: 25
<212> TYPE: DNA
<213> ORGANISM: Bos taurus
```

<400> SEQUENCE: 88
caaagttggt gacgtgacag aggtc        25

<210> SEQ ID NO 89
<211> LENGTH: 24
<212> TYPE: DNA
<213> ORGANISM: Bos taurus

<400> SEQUENCE: 89
gtgtgccatc cctactttgt ggaa        24

<210> SEQ ID NO 90
<211> LENGTH: 22
<212> TYPE: DNA
<213> ORGANISM: Artificial Sequence
<220> FEATURE:
<223> OTHER INFORMATION: PCR primer

<400> SEQUENCE: 90
gatgtattcc tcagactttt cc        22

<210> SEQ ID NO 91
<211> LENGTH: 20
<212> TYPE: DNA
<213> ORGANISM: Artificial Sequence
<220> FEATURE:
<223> OTHER INFORMATION: PCR primer

<400> SEQUENCE: 91
gtggaatctc atcttaccaa        20

<210> SEQ ID NO 92
<211> LENGTH: 23
<212> TYPE: DNA
<213> ORGANISM: Artificial Sequence
<220> FEATURE:
<223> OTHER INFORMATION: PCR Primer

<400> SEQUENCE: 92
ggcaagttgc tcagctgttt ttg        23

<210> SEQ ID NO 93
<211> LENGTH: 22
<212> TYPE: DNA
<213> ORGANISM: Artificial Sequence
<220> FEATURE:
<223> OTHER INFORMATION: PCR primer

<400> SEQUENCE: 93
tccgcatggt ttagcaggat tc        22

<210> SEQ ID NO 94
<211> LENGTH: 24
<212> TYPE: DNA
<213> ORGANISM: Artificial Sequence
<220> FEATURE:
<223> OTHER INFORMATION: PCR Primer

<400> SEQUENCE: 94
atcgaacctg ggtcttctgc attg        24

<210> SEQ ID NO 95
<211> LENGTH: 23
<212> TYPE: DNA
<213> ORGANISM: Artificial Sequence

```
<220> FEATURE:
<223> OTHER INFORMATION: PCR Primer

<400> SEQUENCE: 95
tccgcatggt ttagcaggat tca                                            23

<210> SEQ ID NO 96
<211> LENGTH: 25
<212> TYPE: DNA
<213> ORGANISM: Artificial Sequence
<220> FEATURE:
<223> OTHER INFORMATION: PCR primer

<400> SEQUENCE: 96
ccttgaggta ggagagtgtt ttggg                                          25

<210> SEQ ID NO 97
<211> LENGTH: 25
<212> TYPE: DNA
<213> ORGANISM: Artificial Sequence
<220> FEATURE:
<223> OTHER INFORMATION: PCR primer

<400> SEQUENCE: 97
ttcaccagaa gacaaggaga attgc                                          25

<210> SEQ ID NO 98
<211> LENGTH: 27
<212> TYPE: DNA
<213> ORGANISM: Artificial Sequence
<220> FEATURE:
<223> OTHER INFORMATION: PCR primer

<400> SEQUENCE: 98
taaggccaat tactgctctg gagacta                                        27

<210> SEQ ID NO 99
<211> LENGTH: 28
<212> TYPE: DNA
<213> ORGANISM: Artificial Sequence
<220> FEATURE:
<223> OTHER INFORMATION: PCR primer

<400> SEQUENCE: 99 ccttttttaga agtcaaggta acagacac                                      28

<210> SEQ ID NO 100
<211> LENGTH: 24
<212> TYPE: DNA
<213> ORGANISM: Artificial Sequence
<220> FEATURE:
<223> OTHER INFORMATION: PCR Primer

<400> SEQUENCE: 100
tgattggaga catctttgtg ggag                                           24

<210> SEQ ID NO 101
<211> LENGTH: 27
<212> TYPE: DNA
<213> ORGANISM: Artificial Sequence
<220> FEATURE:
<223> OTHER INFORMATION: PCR primer

<400> SEQUENCE: 101
taaggccaat tactgctctg gagatta                                        27
```

```
<210> SEQ ID NO 102
<211> LENGTH: 24
<212> TYPE: DNA
<213> ORGANISM: Artificial Sequence
<220> FEATURE:
<223> OTHER INFORMATION: PCR primer

<400> SEQUENCE: 102
gcatcgagat tctgtcacaa tcaa                                        24

<210> SEQ ID NO 103
<211> LENGTH: 25
<212> TYPE: DNA
<213> ORGANISM: Artificial Sequence
<220> FEATURE:
<223> OTHER INFORMATION: PCR primer

<400> SEQUENCE: 103
acgtactctt catttcacag cctac                                       25

<210> SEQ ID NO 104
<211> LENGTH: 25
<212> TYPE: DNA
<213> ORGANISM: Artificial Sequence
<220> FEATURE:
<223> OTHER INFORMATION: PCR Primer

<400> SEQUENCE: 104
gtctggggtg agatagtttt cttgg                                       25

<210> SEQ ID NO 105
<211> LENGTH: 24
<212> TYPE: DNA
<213> ORGANISM: Artificial Sequence
<220> FEATURE:
<223> OTHER INFORMATION: PCR Primer

<400> SEQUENCE: 105
ggcagagatg ttggtcttgg gtgt                                        24

<210> SEQ ID NO 106
<211> LENGTH: 46
<212> TYPE: DNA
<213> ORGANISM: Artificial Sequence
<220> FEATURE:
<223> OTHER INFORMATION: TALENs

<400> SEQUENCE: 106
ctcctccatt gcggacatgg acttctcagc ccttctgagt cagatc                46
```